United States Patent
Heo et al.

(10) Patent No.: US 11,081,655 B2
(45) Date of Patent: Aug. 3, 2021

(54) HETEROCYCLIC COMPOUND AND ORGANIC LIGHT EMITTING DEVICE USING THE SAME

(71) Applicant: LG CHEM, LTD., Seoul (KR)

(72) Inventors: Dong Uk Heo, Daejeon (KR); Dong Hoon Lee, Daejeon (KR); Jung Oh Huh, Daejeon (KR); Boon Jae Jang, Daejeon (KR); Mi Yeon Han, Daejeon (KR); Min Woo Jung, Daejeon (KR); Jung Hoon Yang, Daejeon (KR)

(73) Assignee: LG CHEM, LTD., Seoul (KR)

( * ) Notice: Subject to any disclaimer, the term of this patent is extended or adjusted under 35 U.S.C. 154(b) by 72 days.

(21) Appl. No.: 16/486,129

(22) PCT Filed: Mar. 6, 2018

(86) PCT No.: PCT/KR2018/002657
§ 371 (c)(1),
(2) Date: Aug. 14, 2019

(87) PCT Pub. No.: WO2018/190516
PCT Pub. Date: Oct. 18, 2018

(65) Prior Publication Data
US 2019/0372024 A1 Dec. 5, 2019

(30) Foreign Application Priority Data

Apr. 13, 2017 (KR) .................. 10-2017-0048045

(51) Int. Cl.
*H01L 51/50* (2006.01)
*H01L 51/00* (2006.01)
(Continued)

(52) U.S. Cl.
CPC ........ *H01L 51/0073* (2013.01); *C07D 405/14* (2013.01); *C07D 409/14* (2013.01);
(Continued)

(58) Field of Classification Search
None
See application file for complete search history.

(56) References Cited

U.S. PATENT DOCUMENTS

2014/0138652 A1 5/2014 Song et al.
2016/0028021 A1* 1/2016 Zeng .................... C07D 409/10
257/40
(Continued)

FOREIGN PATENT DOCUMENTS

EP 2966706 A2 1/2016
JP 2011-084531 A 4/2011
(Continued)

*Primary Examiner* — Gregory D Clark
(74) *Attorney, Agent, or Firm* — Dentons US LLP

(57) ABSTRACT

The present disclosure relates to a novel cyclic compound represented by Chemical Formula 1 and an organic light emitting device using the same. The compound is used as a material of an organic material layer of the organic light emitting device.

[Chemical Formula 1]

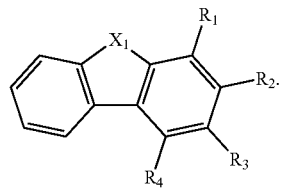

7 Claims, 1 Drawing Sheet

(51) Int. Cl.
  *C07D 405/14*     (2006.01)
  *C07D 409/14*     (2006.01)
  *C09K 11/06*      (2006.01)

(52) U.S. Cl.
  CPC .......... *C09K 11/06* (2013.01); *H01L 51/0052* (2013.01); *H01L 51/0058* (2013.01); *H01L 51/0067* (2013.01); *H01L 51/0074* (2013.01); *C09K 2211/1018* (2013.01); *H01L 51/5072* (2013.01)

(56) References Cited

U.S. PATENT DOCUMENTS

| | | |
|---|---|---|
| 2016/0093808 A1 | 3/2016 | Adamovich et al. |
| 2016/0099422 A1 | 4/2016 | Zeng et al. |
| 2017/0018723 A1 | 1/2017 | Cha et al. |
| 2017/0033296 A1 | 2/2017 | Parham et al. |
| 2017/0213988 A1 | 7/2017 | Park et al. |
| 2018/0037546 A1 | 2/2018 | Sugino et al. |
| 2018/0062088 A1 | 3/2018 | Cho et al. |
| 2018/0123055 A1 | 5/2018 | Park et al. |
| 2018/0233669 A1 | 8/2018 | Lee et al. |

FOREIGN PATENT DOCUMENTS

| | | | |
|---|---|---|---|
| JP | 2014-017494 A | 1/2014 | |
| JP | 2015-125845 A | 7/2015 | |
| JP | 2015-137269 A | 7/2015 | |
| JP | 2016-019002 A | 2/2016 | |
| JP | 2016-149473 A | 8/2016 | |
| JP | 2019-532951 A | 11/2019 | |
| JP | 2019-535679 A | 12/2019 | |
| KR | 10-2000-0051826 A | 8/2000 | |
| KR | 10-2014-0014959 A | 2/2014 | |
| KR | 10-2014-0065863 A | 5/2014 | |
| KR | 10-2015-0012974 A | 2/2015 | |
| KR | 2015012974 * | 2/2015 | ............. C09K 11/06 |
| KR | 10-2016-0004513 A | 1/2016 | |
| KR | 10-2016-0006633 A | 1/2016 | |
| KR | 10-2017-0013152 A | 2/2017 | |
| KR | 10-2017-0013153 A | 2/2017 | |
| KR | 10-2017-0057660 A | 5/2017 | |
| KR | 10-2018-0031224 A | 3/2018 | |
| WO | 2003/012890 A2 | 2/2003 | |
| WO | 2013/168534 A1 | 11/2013 | |
| WO | 2016/003225 A2 | 1/2016 | |
| WO | 2016/129672 A1 | 8/2016 | |
| WO | 2016/171429 A2 | 10/2016 | |
| WO | 2017/018795 A2 | 2/2017 | |
| WO | 2017/023021 A1 | 2/2017 | |
| WO | 2018/060307 A1 | 4/2018 | |
| WO | 2018/135798 A1 | 7/2018 | |

* cited by examiner

[FIG. 1]
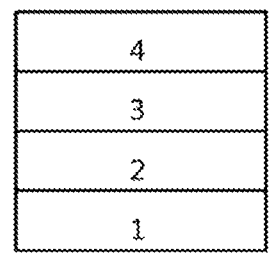
[FIG. 2]
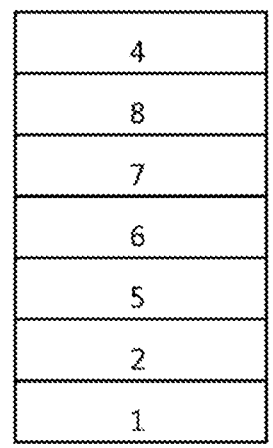

HETEROCYCLIC COMPOUND AND ORGANIC LIGHT EMITTING DEVICE USING THE SAME

CROSS-REFERENCE TO RELATED APPLICATION(S)

This application is a National Phase entry pursuant to 35 U.S.C. § 371 of PCT/KR2018/002657 filed on Mar. 6, 2018, and claims the benefit of priority from Korean Patent Application No. 10-2017-0048045 filed on Apr. 13, 2017, the full disclosure of which is incorporated herein by reference.

TECHNICAL FIELD

The present disclosure relates to a novel heterocyclic compound and an organic light emitting device comprising the same.

BACKGROUND ART

In general, an organic light emitting phenomenon refers to a phenomenon where electric energy is converted into light energy by using an organic material. The organic light emitting device using the organic light emitting phenomenon has characteristics such as a wide viewing angle, an excellent contrast, a fast response time, an excellent luminance, driving voltage and response speed, and thus many studies have proceeded.

The organic light emitting device generally has a structure which comprises an anode, a cathode, and an organic material layer interposed between the anode and the cathode. The organic material layer frequently have a multilayered structure that comprises different materials in order to enhance efficiency and stability of the organic light emitting device, and for example, the organic material layer may be formed of a hole injection layer, a hole transport layer, a light emitting layer, an electron transport layer, an electron injection layer and the like. In the structure of the organic light emitting device, if a voltage is applied between two electrodes, the holes are injected from an anode into the organic material layer and the electrons are injected from the cathode into the organic material layer, and when the injected holes and the electrons meet each other, an exciton is formed, and light is emitted when the exciton falls to a ground state again.

There is a continuing need for the development of new materials for the organic materials used in such organic light emitting devices.

PRIOR ART LITERATURE

Patent Literature (Patent Literature 0001) Korean Patent Laid-open Publication No. 10-2000-0051826

DETAILED DESCRIPTION OF THE DISCLOSURE

Technical Problem

It is an object of the present disclosure to provide a novel heterocyclic compound and an organic light emitting device comprising the same.

Technical Solution

In order to achieve the above object, the present disclosure provides a compound represented by Chemical Formula 1:

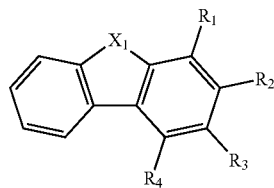

[Formula 1]

wherein, in Chemical Formula 1,
$X_1$ is O or S,
two of $R_1$ to $R_4$ are hydrogen, and the rest are $Ar_n$ which differ from each other,
$Ar_1$ is each independently $-L-Ar_2$,
L is each independently a direct bond, or substituted or unsubstituted $C_{6-60}$ arylene,
$Ar_2$ is each independently represented by Chemical Formula 2,

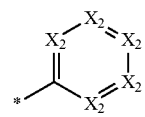

[Formula 2]

in Chemical Formula 2,
$X_2$ is each independently N, or $CR_5$, and
$R_5$ is each independently hydrogen, deuterium, substituted or unsubstituted $C_{1-60}$ alkyl, substituted or unsubstituted $C_{6-60}$ aryl, or substituted or unsubstituted $C_{5-60}$ heteroaryl containing at least one heteroatom selected from the group consisting of N, O and S.

The present disclosure also provides an organic light emitting device comprising a first electrode; a second electrode provided at a side opposite to the first electrode; and at least one layer of the organic material layers provided between the first electrode and the second electrode, wherein the at least one layer of the organic material layers includes a compound represented by the Chemical Formula 1.

Advantageous Effects

The compound represented by the Chemical Formula 1 described above can be used as a material of an organic material layer of an organic light emitting device, and can allow improvement of the efficiency, low driving voltage and/or improvement of the lifetime characteristic when applied to the organic light emitting device. In particular, the compound represented by the Chemical Formula 1 can be used as hole injection, hole transport, hole injection and transport, light emission, electron transport, or electron injection materials.

BRIEF DESCRIPTION OF DRAWINGS

FIG. 1 shows an example of an organic light emitting device comprising a substrate 1, an anode 2, a light emitting layer 3, and a cathode 4.

FIG. 2 shows an example of an organic light emitting device comprising a substrate 1, an anode 2, a hole injection layer 5, a hole transport layer 6, a light emitting layer 7, an electron transport layer 8, and a cathode 4.

DETAILED DESCRIPTION OF THE EMBODIMENTS

Hereinafter, the present disclosure will be described in more detail to help understanding of the present disclosure.

The present disclosure provides a compound represented by the Chemical Formula 1.

In the present specification,

or ⁀ mean a bond connected to another substituent group.

As used herein, the term "substituted or unsubstituted" means that substitution is performed by one or more substituent groups selected from the group consisting of deuterium; a halogen group; a nitrile group; a nitro group; a hydroxyl group; a carbonyl group; an ester group; an imide group; an amino group; a phosphine oxide group; an alkoxy group; an aryloxy group; an alkylthioxy group; an arylthioxy group; an alkylsulfoxy group; an arylsulfoxy group; a silyl group; a boron group; an alkyl group; a cycloalkyl group; an alkenyl group; an aryl group; an aralkyl group; an aralkenyl group; an alkylaryl group; an alkylamine group; an aralkylamine group; a heteroarylamine group; an arylamine group; an arylphosphine group; or a heterocyclic group containing at least one of N, O, and S atoms, or there is no substituent group, or substitution is performed by a substituent group where two or more substituent groups of the exemplified substituent groups are linked or there is no substituent group. For example, the term "substituent group where two or more substituent groups are linked" may be a biphenyl group. That is, the biphenyl group may be an aryl group, or may be interpreted as a substituent group where two phenyl groups are connected.

In the present specification, the number of carbon atoms in a carbonyl group is not particularly limited, but is preferably 1 to 40. Specifically, the carbonyl group may be compounds having the following structures, but is not limited thereto.

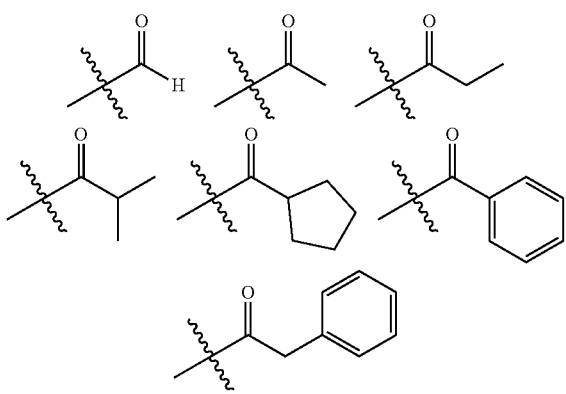

In the present specification, the ester group may have a structure in which oxygen of the ester group may be substituted by a straight-chain, branched-chain, or cyclic alkyl group having 1 to 25 carbon atoms, or an aryl group having 6 to 25 carbon atoms. Specifically, the ester group may be compounds having the following structures, but is not limited thereto.

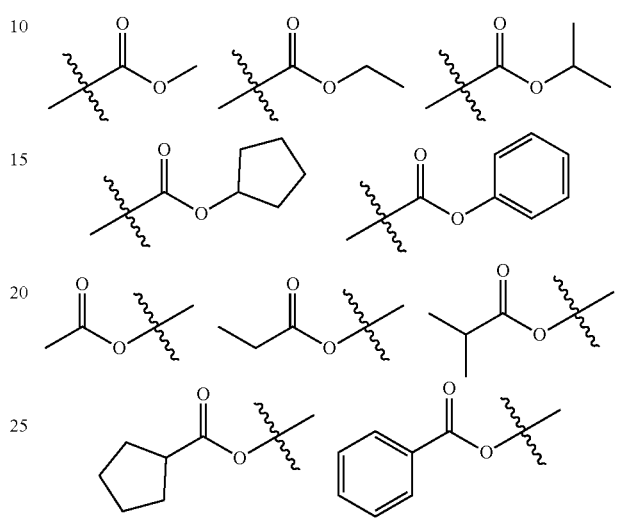

In the present specification, the number of carbon atoms in an imide group is not particularly limited, but is preferably 1 to 25. Specifically, the imide group may be compounds having the following structures, but is not limited thereto.

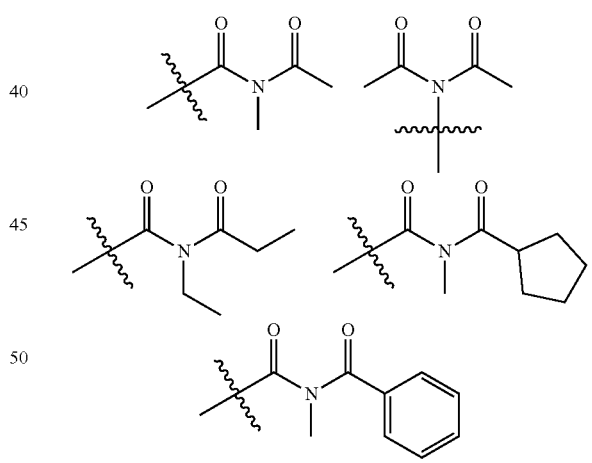

In the present specification, the silyl group specifically includes a trimethylsilyl group, a triethylsilyl group, a t-butyldimethylsilyl group, a vinyldimethylsilyl group, a propyldimethylsilyl group, a triphenylsilyl group, a diphenylsilyl group, a phenylsilyl group, and the like, but is not limited thereto.

In the present specification, the boron group specifically includes a trimethylboron group, a triethylboron group, a t-butyldimethylboron group, a triphenylboron group, a phenylboron group, and the like, but is not limited thereto.

In the present specification, examples of a halogen group include fluorine, chlorine, bromine, or iodine.

In the present specification, the alkyl group may be a straight chain or a branched chain, and the number of carbon atoms thereof is not particularly limited, but is preferably 1 to 40. According to one embodiment, the alkyl group has 1 to 20 carbon atoms. According to another embodiment, the alkyl group has 1 to 10 carbon atoms. According to still another embodiment, the alkyl group has 1 to 6 carbon atoms. Specific examples of the alkyl group include methyl, ethyl, propyl, n-propyl, isopropyl, butyl, n-butyl, isobutyl, tert-butyl, sec-butyl, 1-methyl-butyl, 1-ethyl-butyl, pentyl, n-pentyl, isopentyl, neopentyl, tert-pentyl, hexyl, n-hexyl, 1-methylpentyl, 2-methylpentyl, 4-methyl-2-pentyl, 3,3-dimethylbutyl, 2-ethylbutyl, heptyl, n-heptyl, 1-methylhexyl, cyclopentylmethyl, cyclohexylmethyl, octyl, n-octyl, tert-octyl, 1-methylheptyl, 2-ethylhexyl, 2-propylpentyl, n-nonyl, 2,2-dimethylheptyl, 1-ethyl-propyl, 1,1-dimethyl-propyl, isohexyl, 2-methylpentyl, 4-methylhexyl, 5-methylhexyl, and the like, but are not limited thereto.

In the present specification, the alkenyl group may be a straight chain or a branched chain, and the number of carbon atoms thereof is not particularly limited, but is preferably 2 to 40. According to one embodiment, the alkenyl group has 2 to 20 carbon atoms. According to another embodiment, the alkenyl group has 2 to 10 carbon atoms. According to still another embodiment, the alkenyl group has 2 to 6 carbon atoms. Specific examples thereof include vinyl, 1-propenyl, isopropenyl, 1-butenyl, 2-butenyl, 3-butenyl, 1-pentenyl, 2-pentenyl, 3-pentenyl, 3-methyl-1-butenyl, 1,3-butadienyl, allyl, 1-phenylvinyl-1-yl, 2-phenylvinyl-1-yl, 2,2-diphenyl-vinyl-1-yl, 2-phenyl-2-(naphthyl-1-yl)vinyl-1-yl, 2,2-bis(diphenyl-1-yl)vinyl-1-yl, a stilbenyl group, a styrenyl group, and the like, but are not limited thereto.

In the present specification, the cycloalkyl group is not particularly limited, but the number of carbon atoms thereof is preferably 3 to 60. According to one embodiment, the cycloalkyl group has 3 to 30 carbon atoms. According to another embodiment, the cycloalkyl group has 3 to 20 carbon atoms. According to another embodiment, the cycloalkyl group has 3 to 6 carbon atoms. Specific examples thereof include cyclopropyl, cyclobutyl, cyclopentyl, 3-methylcyclopentyl, 2,3-dimethylcyclopentyl, cyclohexyl, 3-methylcyclohexyl, 4-methylcyclohexyl, 2,3-dimethylcyclohexyl, 3,4,5-trimethylcyclohexyl, 4-tert-butylcyclohexyl, cycloheptyl, cyclooctyl, and the like, but are not limited thereto.

In the present specification, the aryl group is not particularly limited, but preferably has 6 to 60 carbon atoms, and may be a monocyclic aryl group or a polycyclic aryl group. According to one embodiment, the aryl group has 6 to 30 carbon atoms. According to one embodiment, the aryl group has 6 to 20 carbon atoms. The aryl group may be a phenyl group, a biphenyl group, a terphenyl group or the like as the monocyclic aryl group, but is not limited thereto. Examples of the polycyclic aryl group include a naphthyl group, an anthracenyl group, a phenanthryl group, a pyrenyl group, a perylenyl group, a chrycenyl group, a fluorenyl group or the like, but is not limited thereto.

In the present specification, a fluorenyl group may be substituted, and two substituent groups may be linked with each other to form a spiro structure. In the case where the fluorenyl group is substituted,

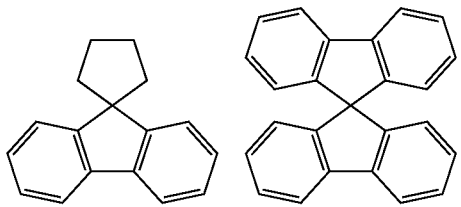

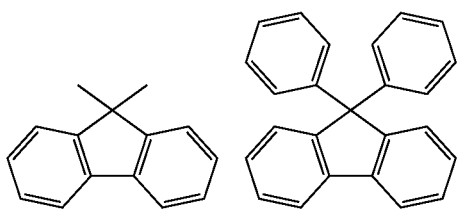

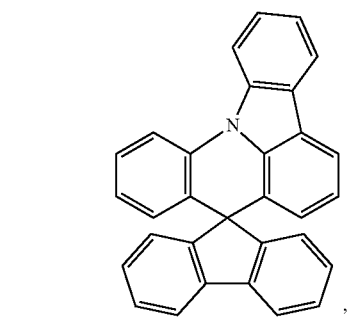

and the like can be formed. However, the structure is not limited thereto.

In the present specification, the heterocyclic group is a heterocyclic group containing at least one of O, N, Si and S as a heteroatom, and the number of carbon atoms thereof is not particularly limited, but is preferably 2 to 60. Examples of the heterocyclic group include a thiophene group, a furan group, a pyrrole group, an imidazole group, a thiazole group, an oxazole group, an oxadiazole group, a triazole group, a pyridyl group, a bipyridyl group, a pyrimidyl group, a triazine group, an acridyl group, a pyridazine group, a pyrazinyl group, a quinolinyl group, a quinazoline group, a quinoxalinyl group, a phthalazinyl group, a pyridopyrimidinyl group, a pyridopyrazinyl group, a pyrazinopyrazinyl group, an isoquinoline group, an indole group, a carbazole group, a benzoxazole group, a benzimidazole group, a benzothiazole group, a benzocarbazole group, a benzothiophene group, a dibenzothiophene group, a benzofuranyl group, a phenanthroline group, an isoxazolyl group, a thiadiazolyl group, a phenothiazinyl group, a dibenzofuranyl group, and the like, but are not limited thereto.

In the present specification, the aryl group in the aralkyl group, the aralkenyl group, the alkylaryl group, and the arylamine group is the same as the aforementioned examples of the aryl group. In the present specification, the alkyl group in the aralkyl group, the alkylaryl group and the alkylamine group is the same as the aforementioned examples of the alkyl group. In the present specification, the heteroaryl in the heteroarylamine can be applied to the aforementioned description of the heterocyclic group. In the present specification, the alkenyl group in the aralkenyl group is the same as the aforementioned examples of the alkenyl group. In the present specification, the aforementioned description of the aryl group may be applied except that the arylene is a divalent group. In the present specification, the aforementioned description of the heterocyclic group can be applied except that the heteroarylene is a divalent group. In the present specification, the aforementioned description of the aryl group or cycloalkyl group can be applied except that the hydrocarbon ring is not a monovalent group but formed by combining two substituent groups. In the present specification, the aforementioned description of the heterocyclic group can be applied, except that the heterocycle is not a monovalent group but formed by combining two substituent groups.

In the Chemical Formula 1, two of $R_1$ to $R_4$ are hydrogen, and the rest are $Ar_1$ which differ from each other. Here, the "$Ar_1$ which differ from each other" means that the overall structure of two $Ar_1$ is different, For example, it includes those having different types of substituent groups and different substitution positions.

Preferably, L is each independently a direct bond, phenylene, or naphthylene.

Preferably, in the Chemical Formula 2, one, two, or three of $X_2$ are N, and the rest are $CR_5$.

Preferably, the Chemical Formula 2 is any one selected from the group consisting of the following:

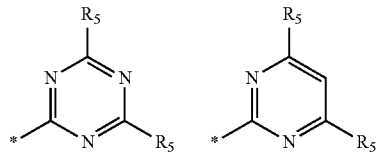

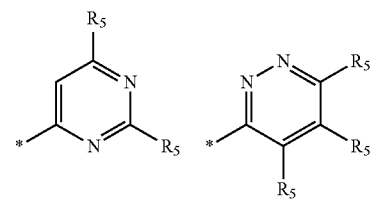

Preferably, in the Chemical Formula 2, at least one of $R_5$ is each independently substituted or unsubstituted $C_{6-60}$ aryl, or substituted or unsubstituted $C_{5-60}$ heteroaryl containing at least one heteroatom selected from the group consisting of N, O and S.

Preferably, $R_5$ is each independently hydrogen, phenyl, biphenylyl, naphthyl, or dibenzofuranyl.

Representative examples of the compound represented by the Chemical Formula 1 are as follows:

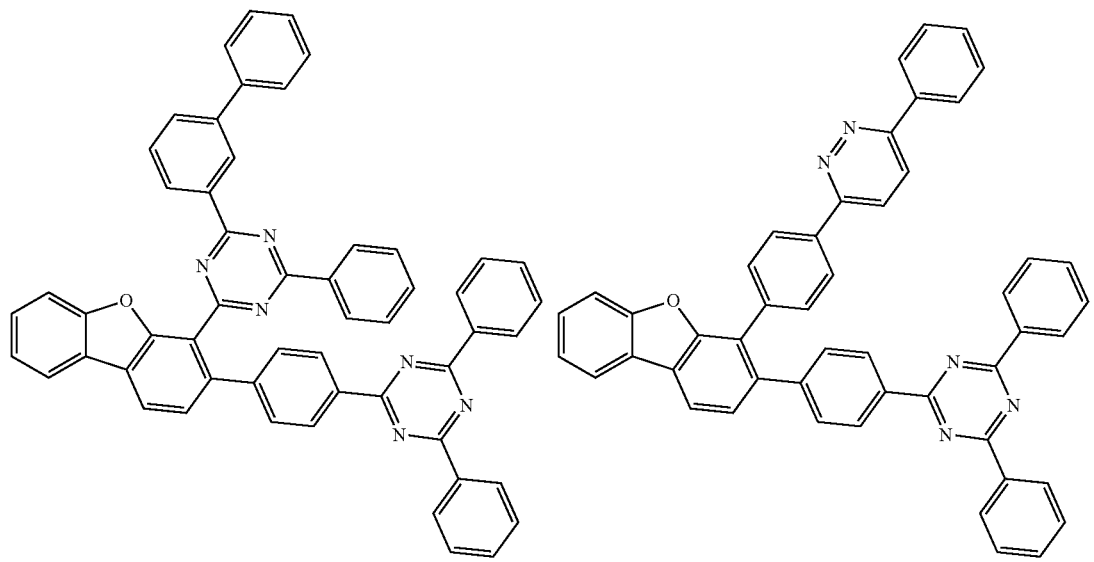

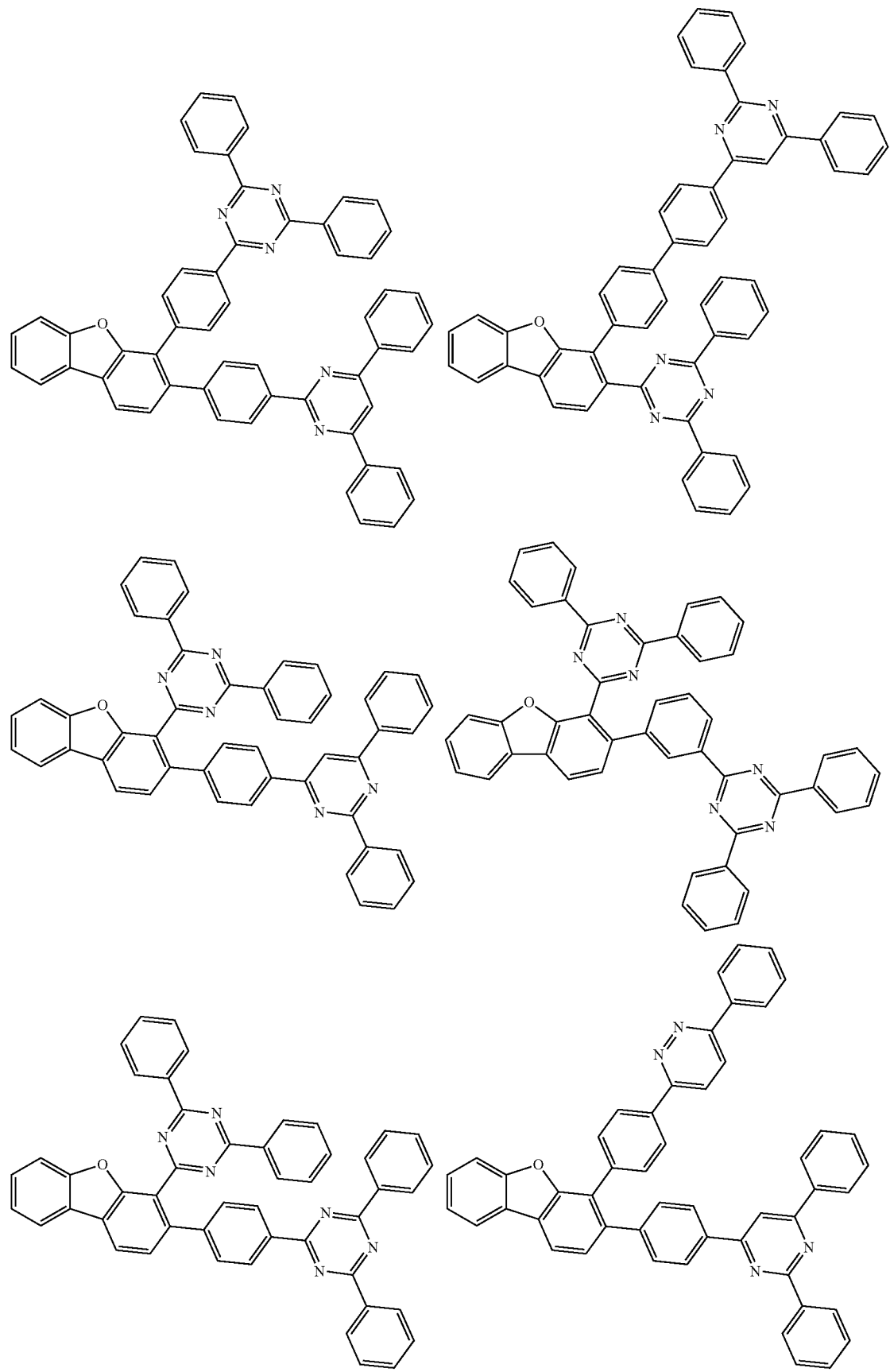

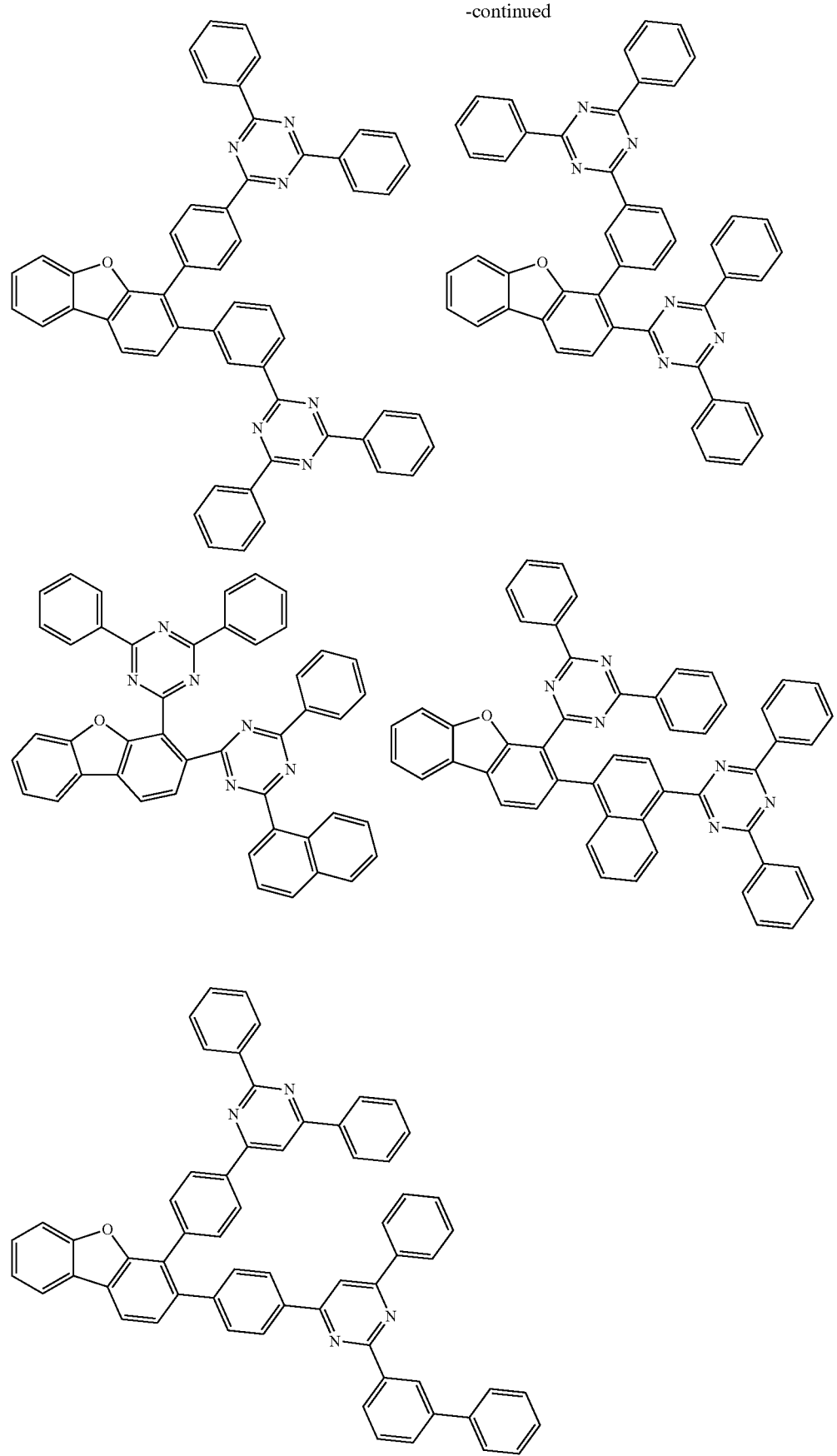

-continued
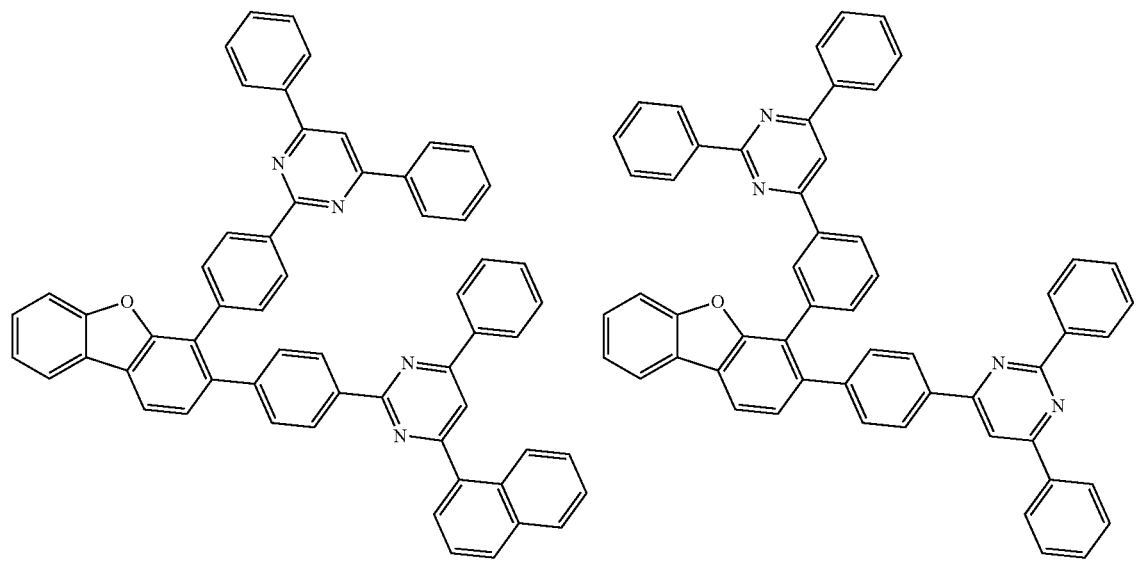
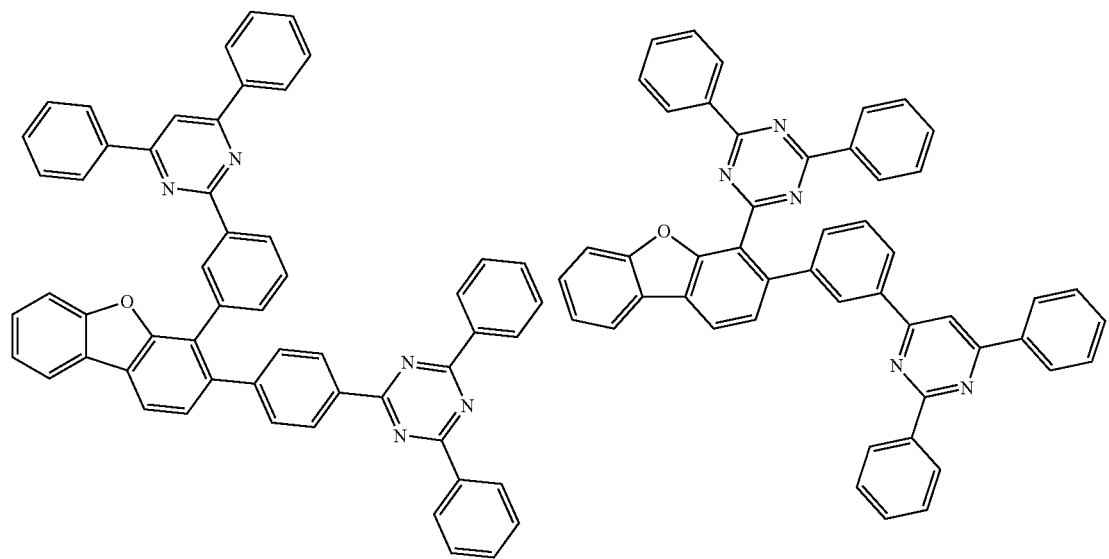

15
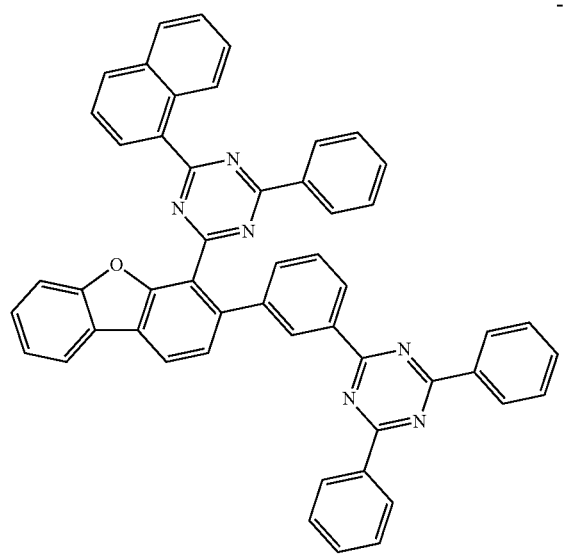
-continued
16
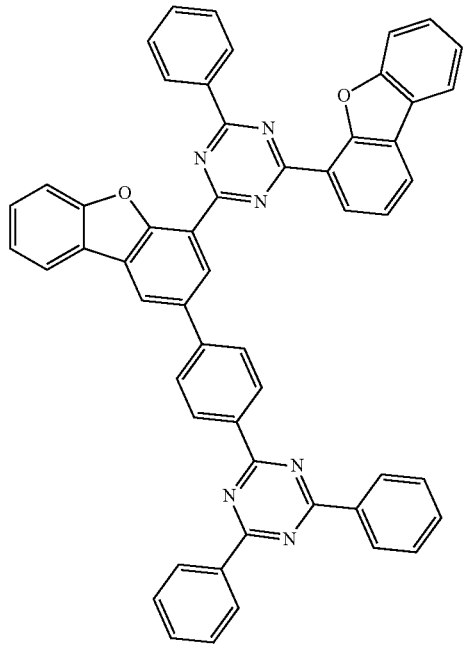
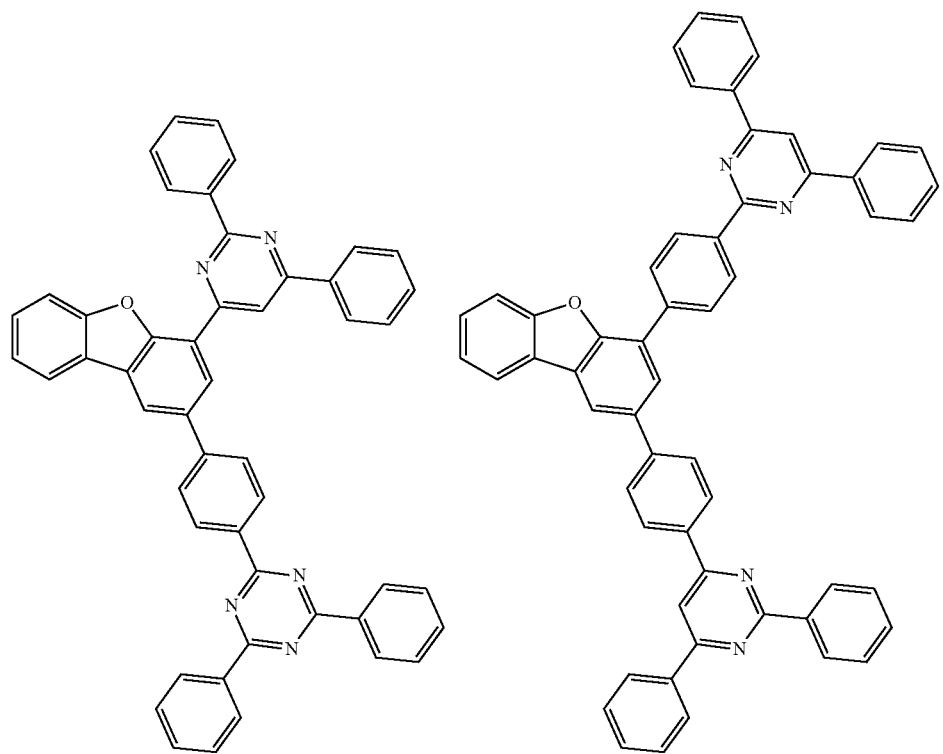

-continued
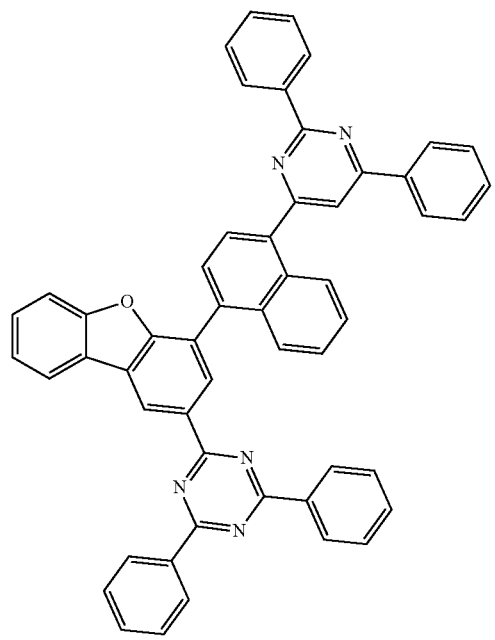 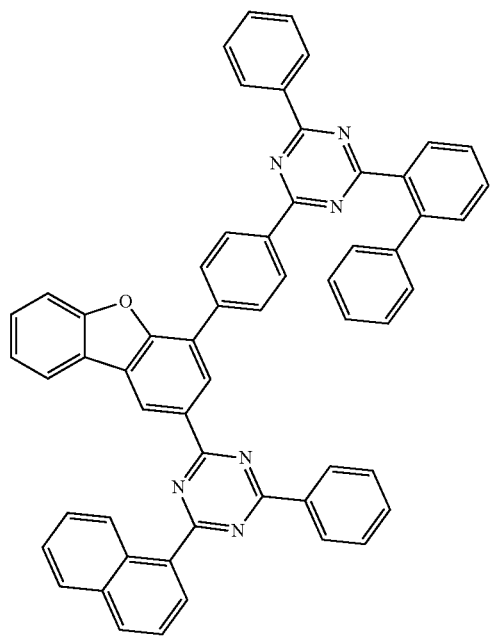
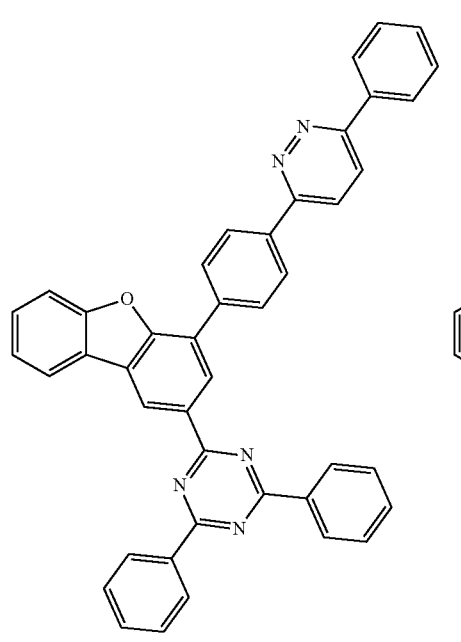 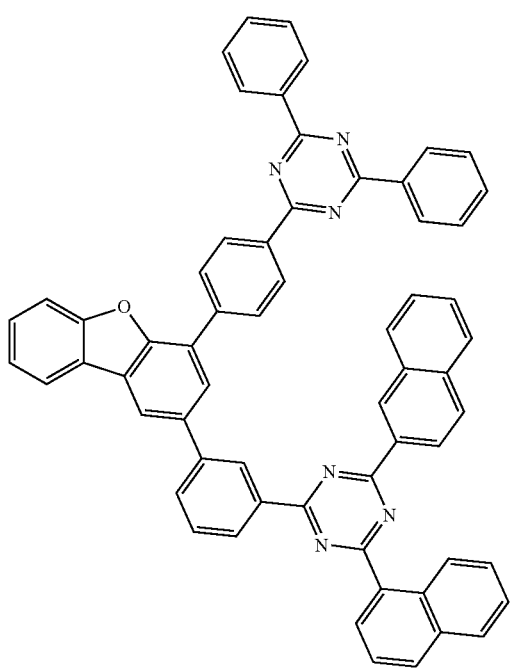

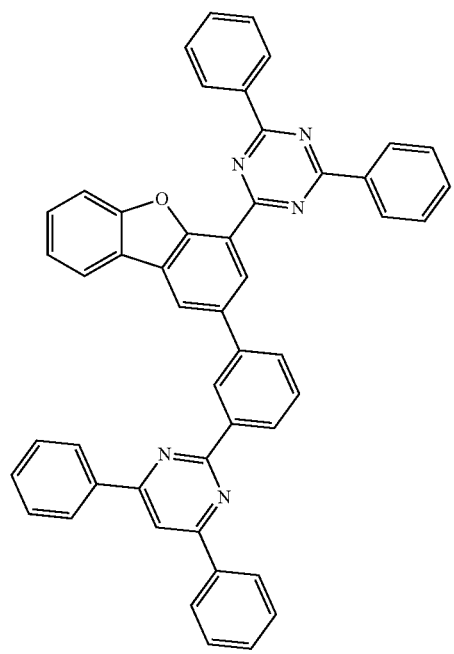
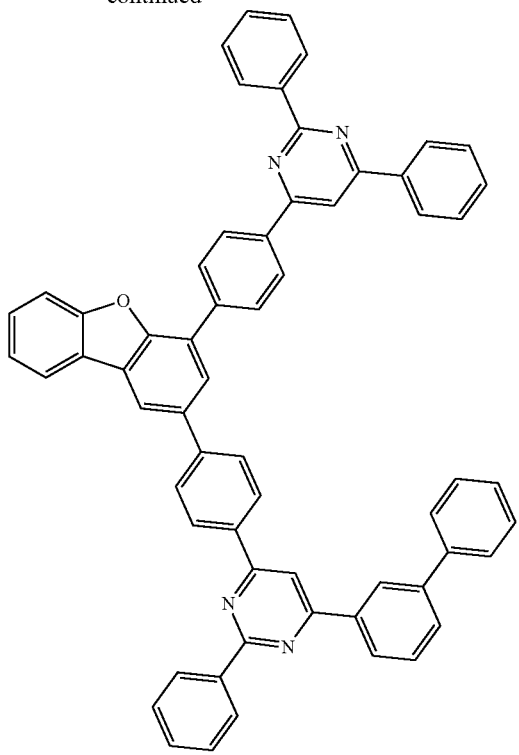
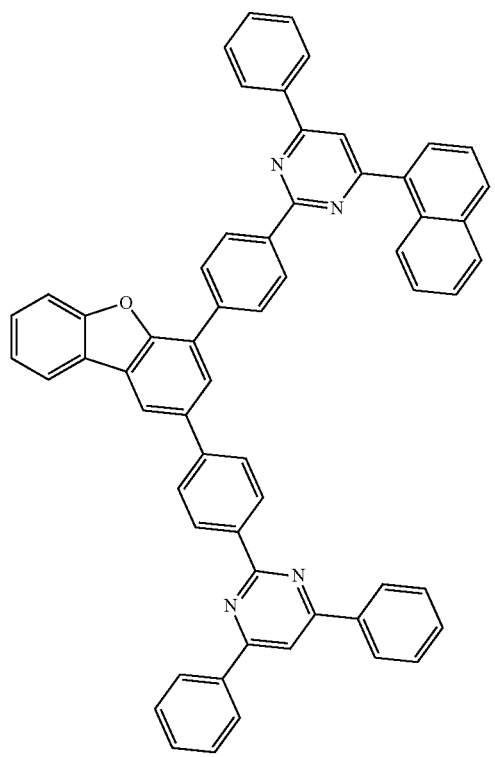 [SMILES: c1ccc(-c2cc(-c3ccccc3)nc(-c3ccc(-c4cc(-c5ccc(-c6nc(-c7ccccc7)cc(-c7cccc8ccccc78)n6)cc5)c5oc6ccccc6c5c4)cc3)n2)cc1]

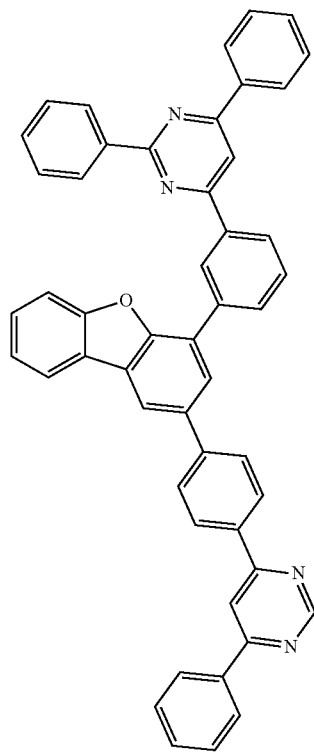
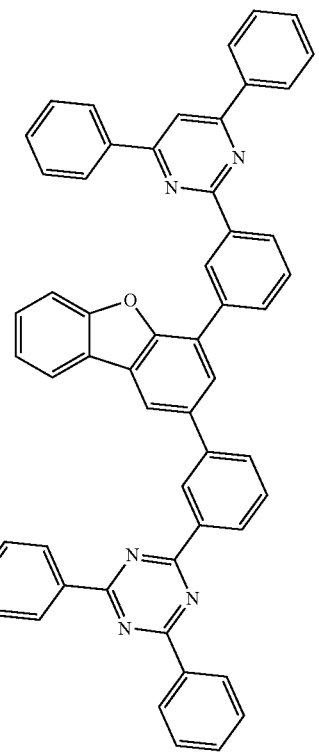
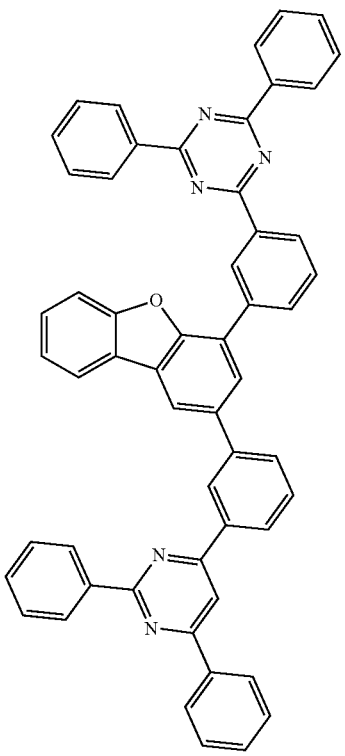
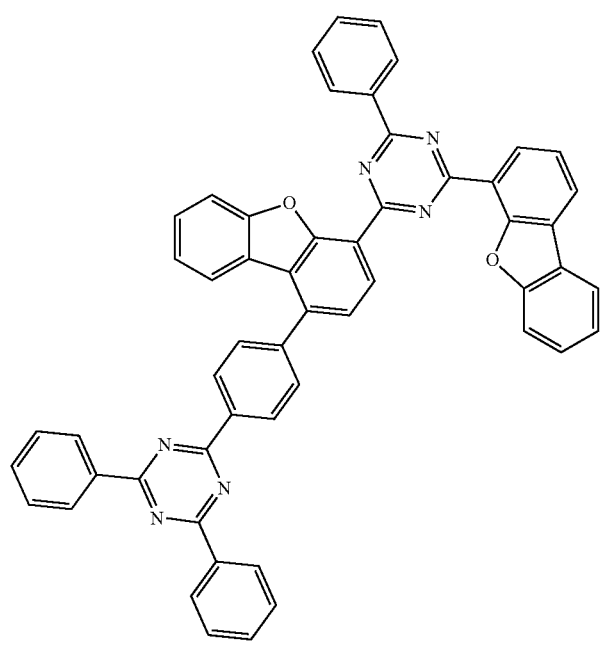
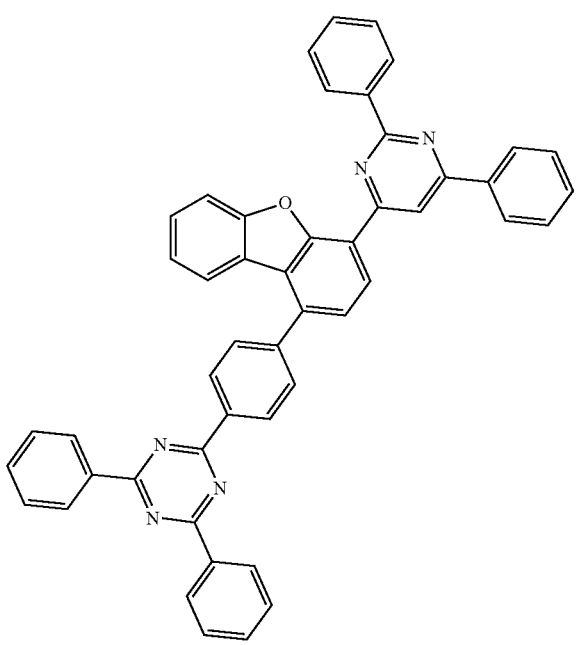

-continued
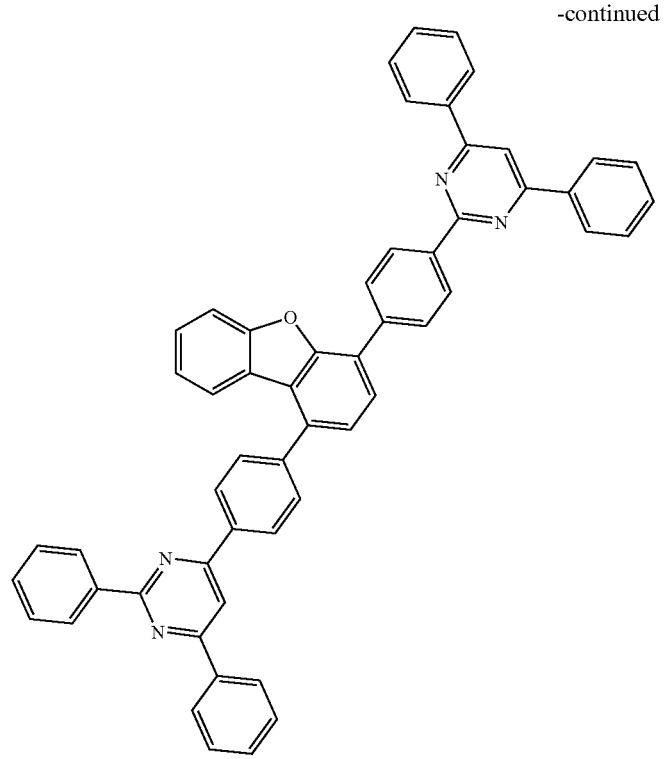
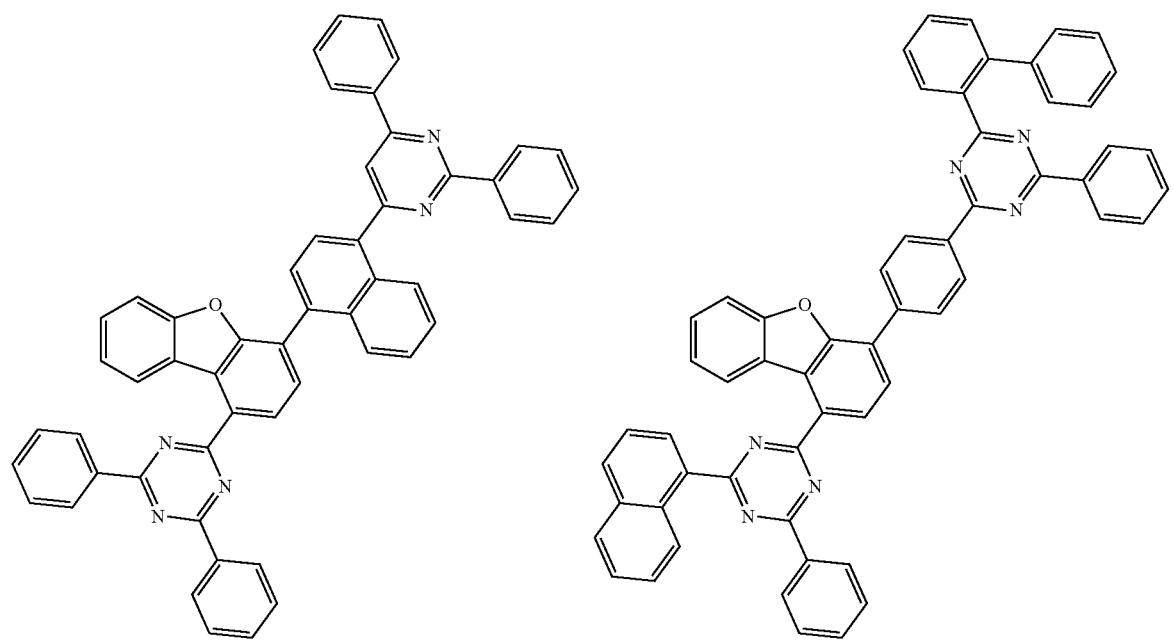

-continued
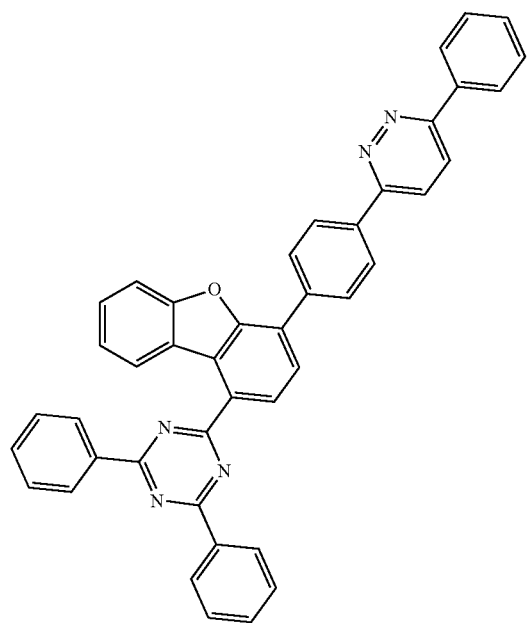
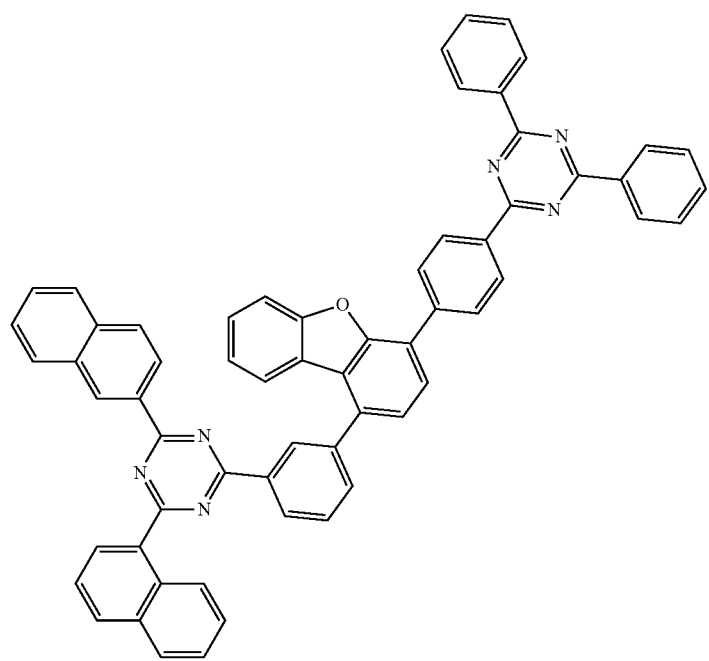

-continued
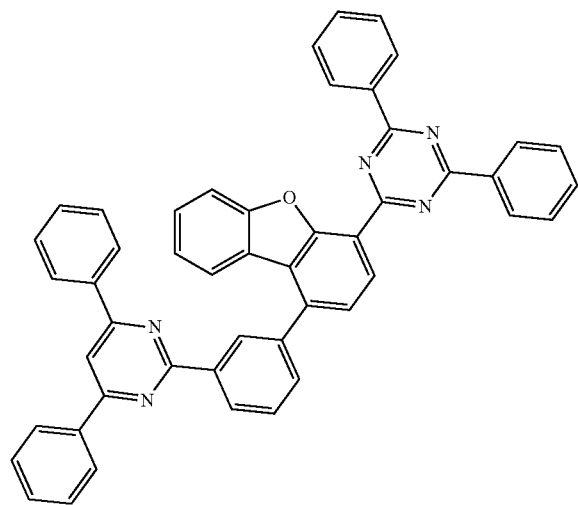

-continued
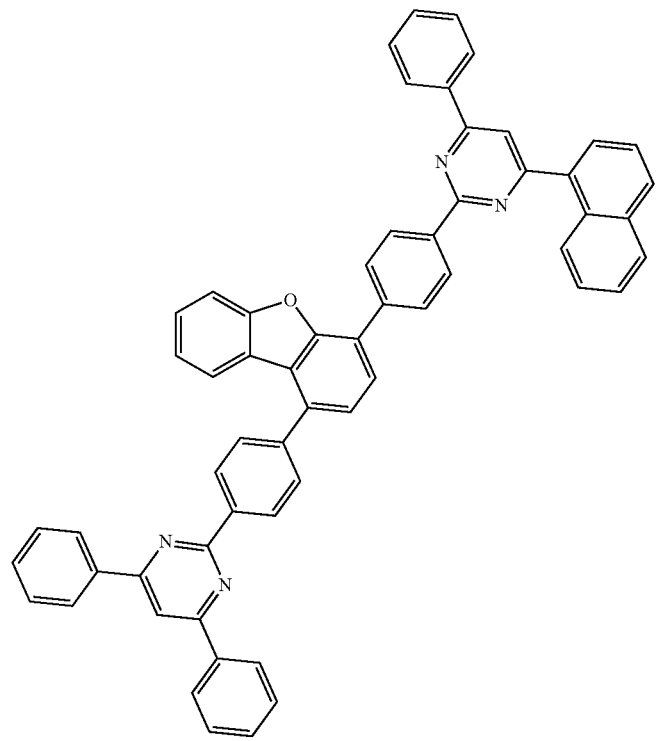
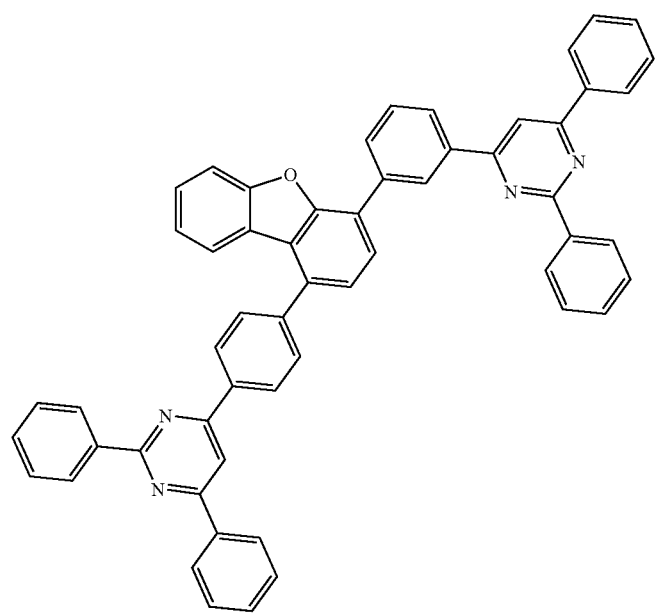

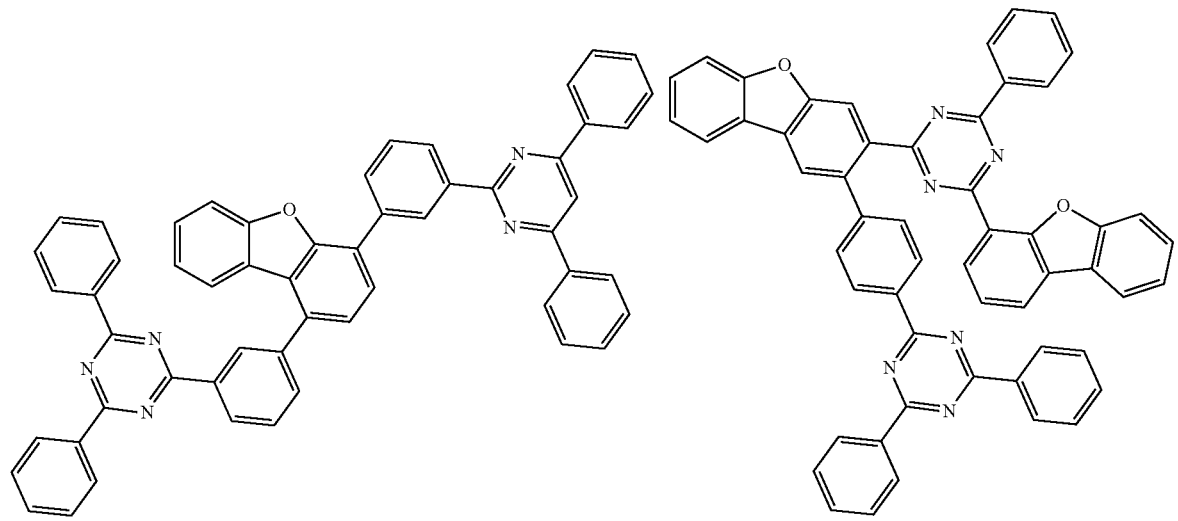
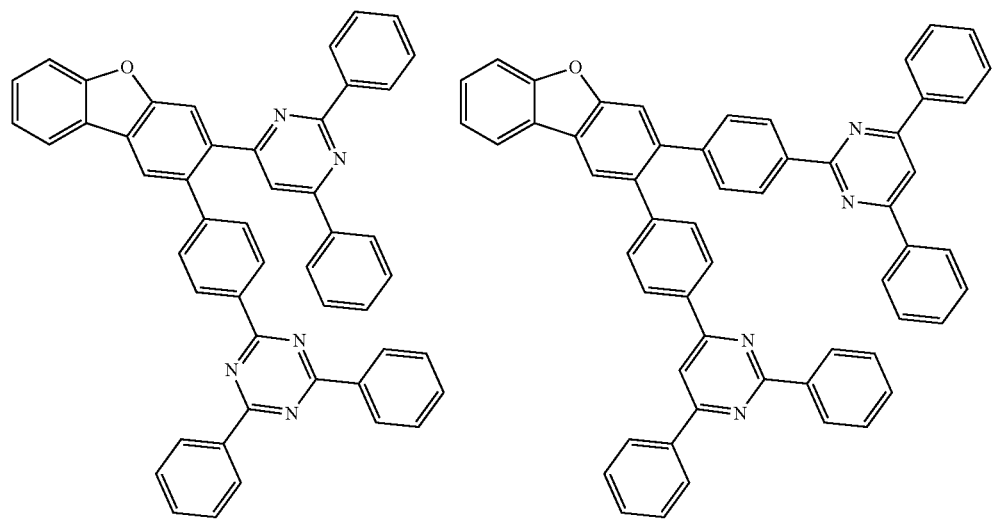
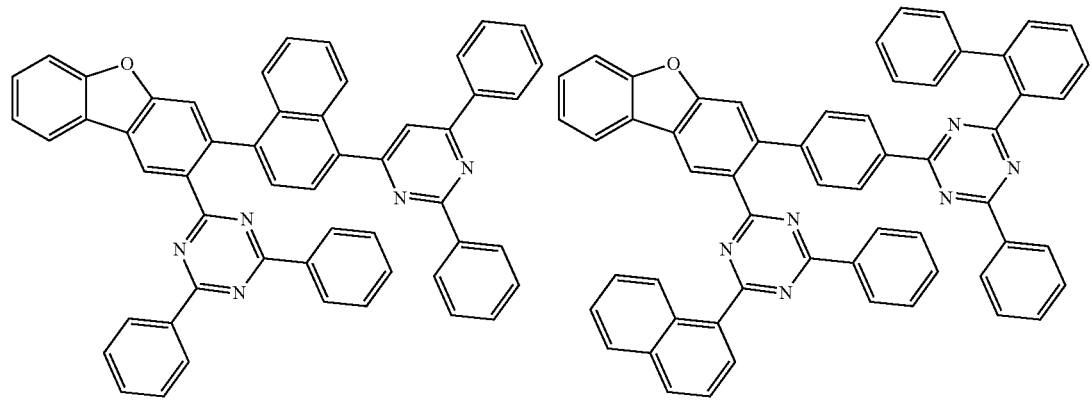

-continued
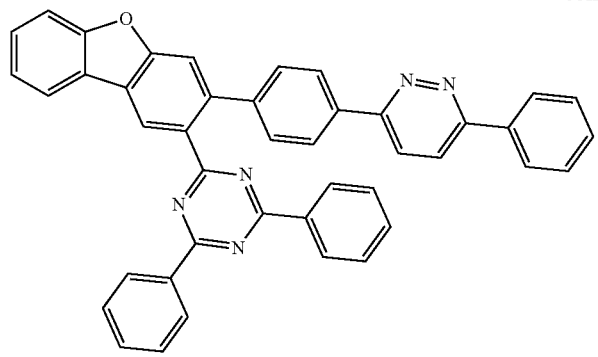
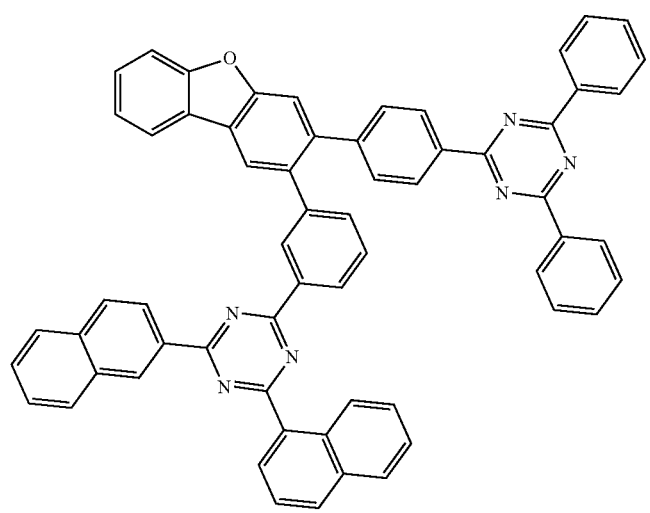
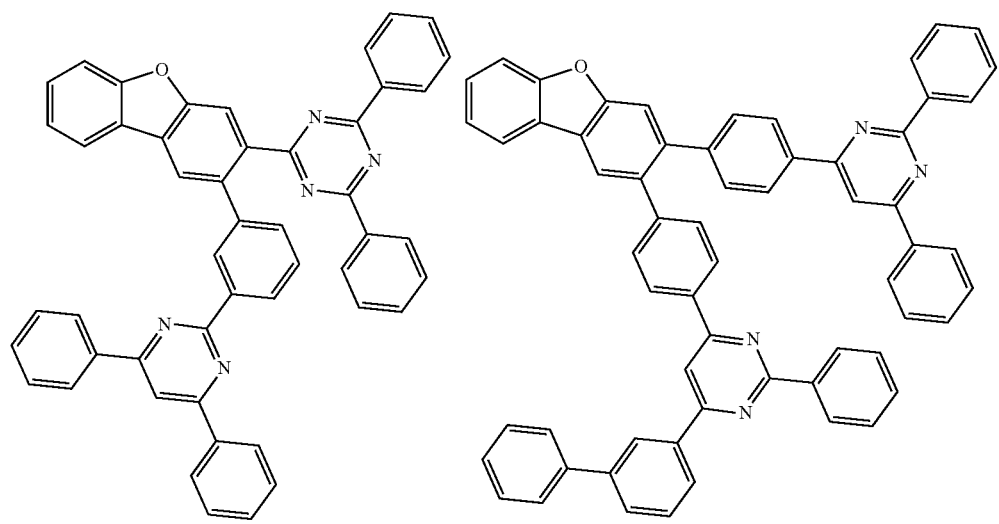

-continued
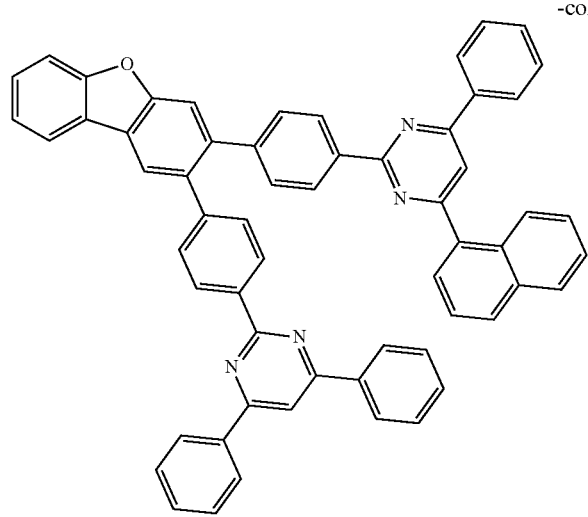
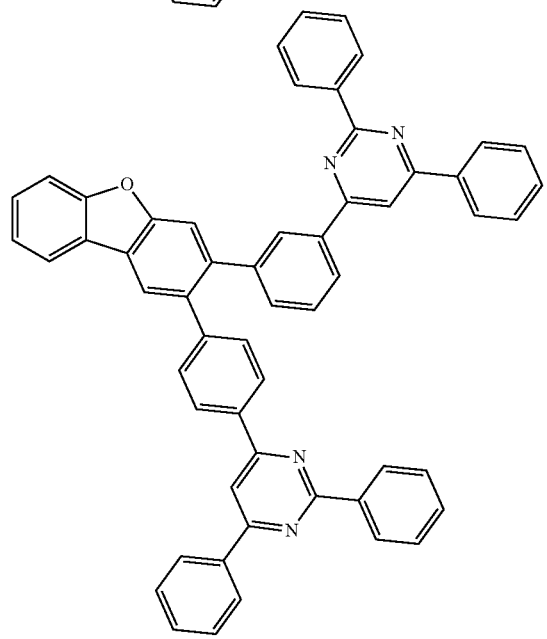
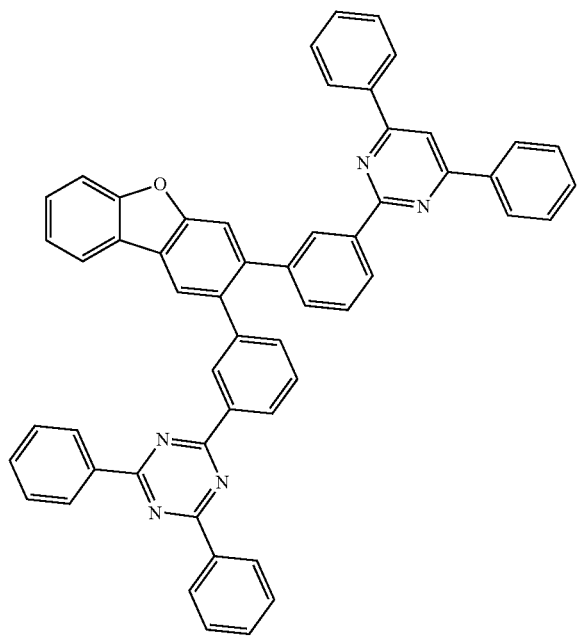
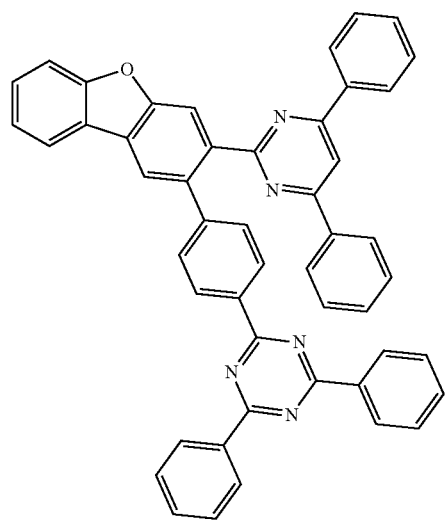
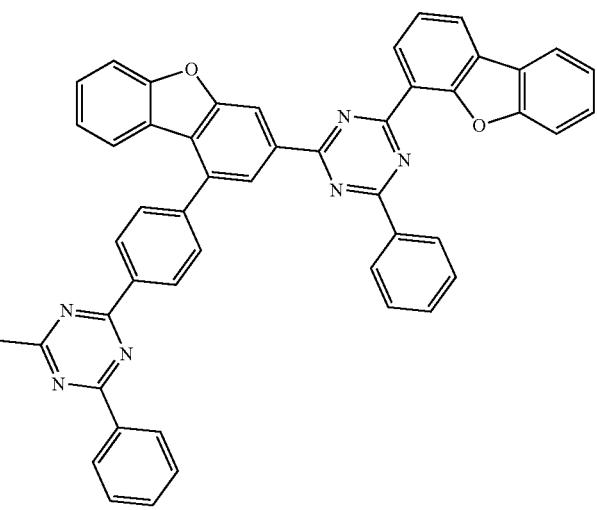

-continued
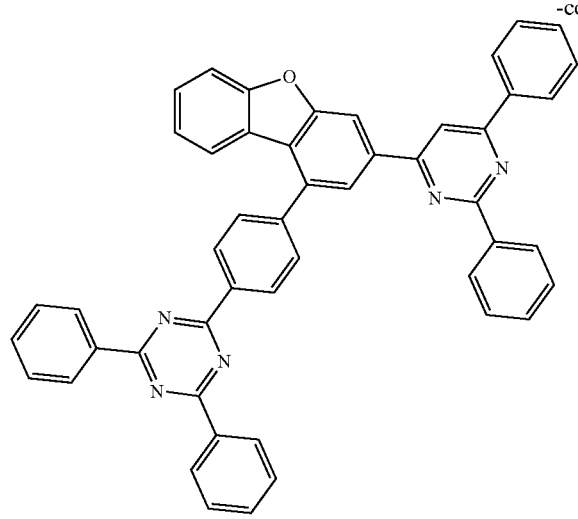
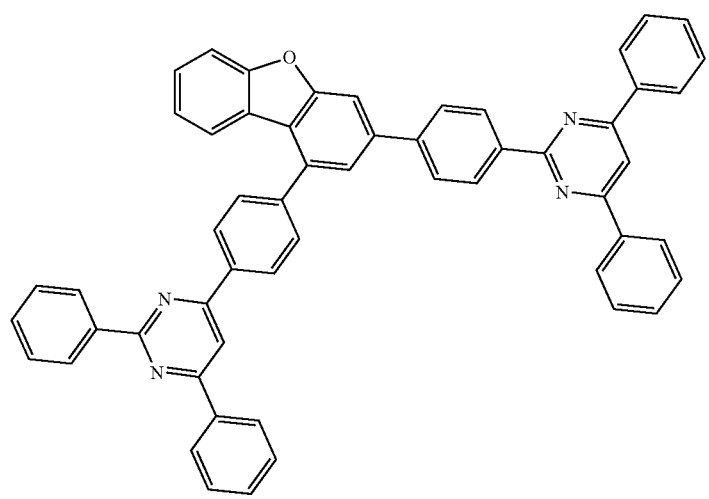
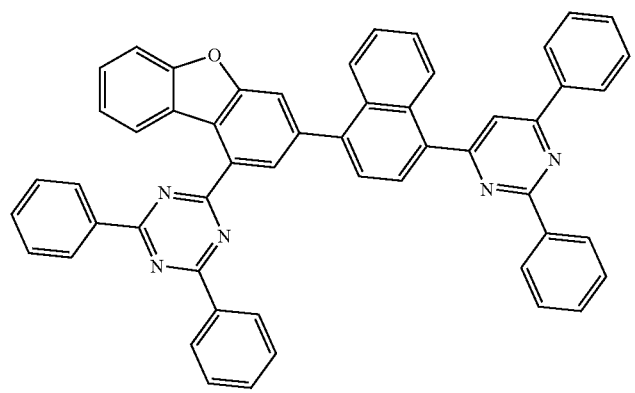

-continued
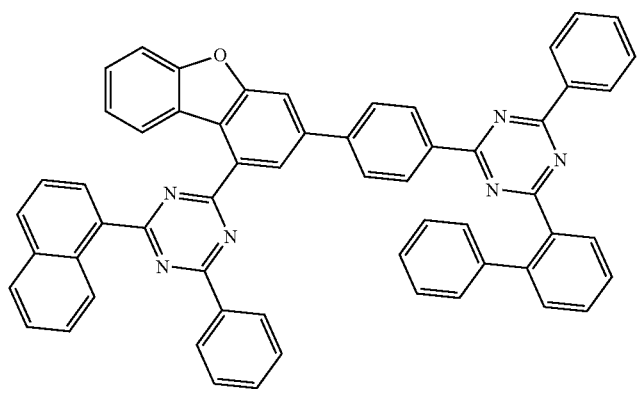
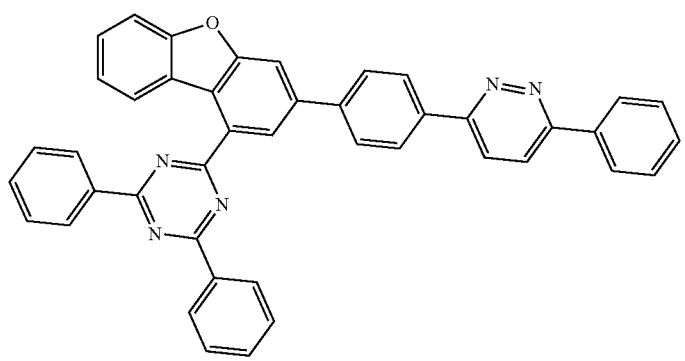
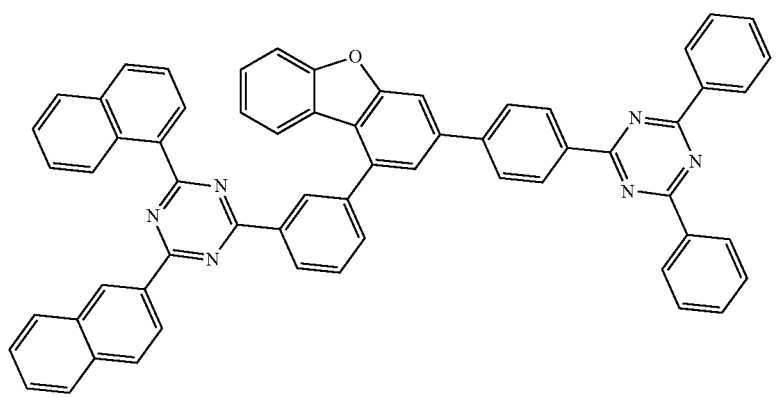
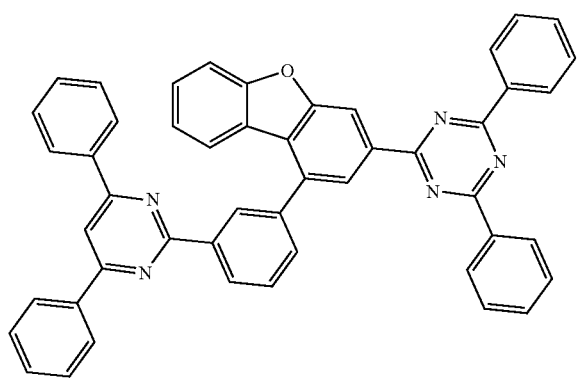

-continued
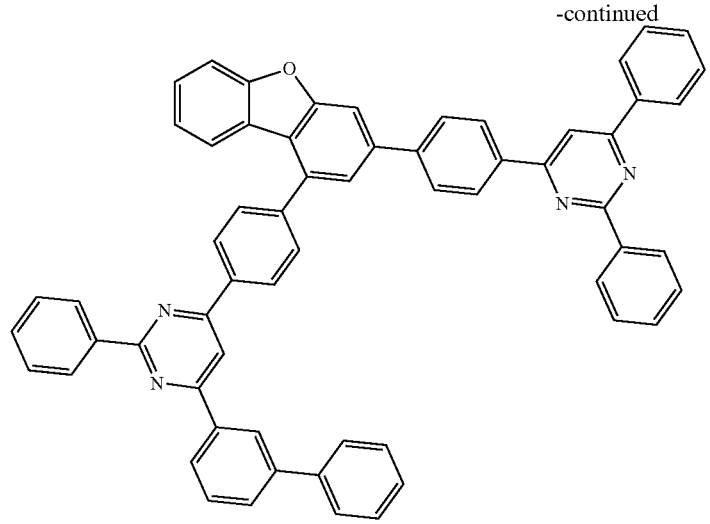
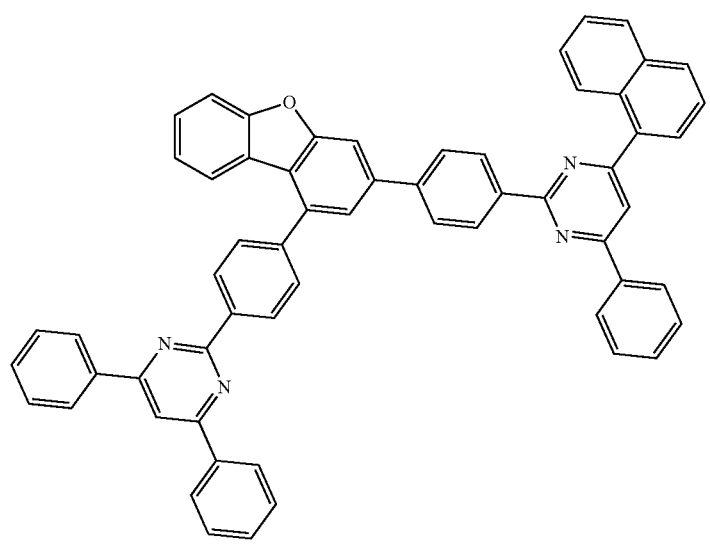
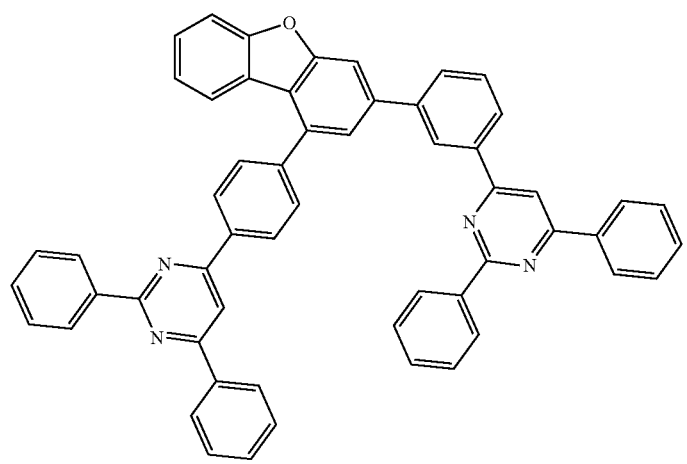

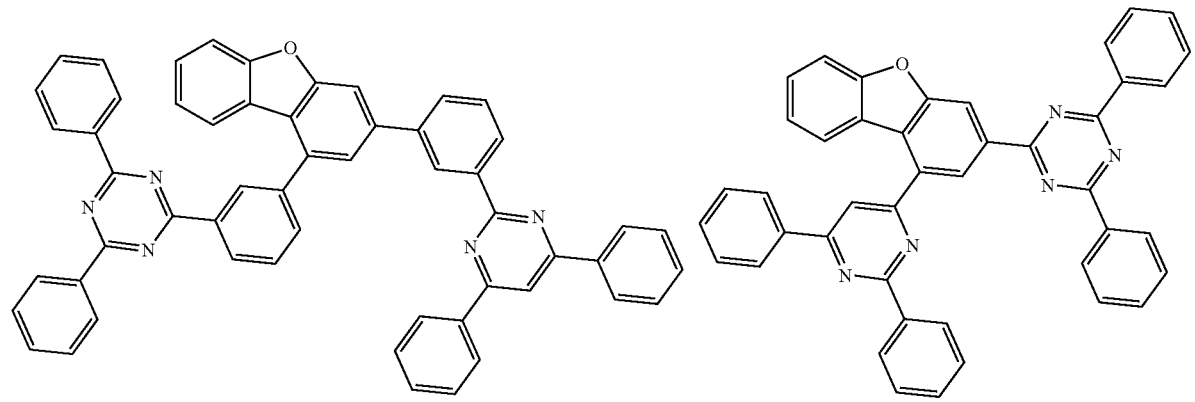
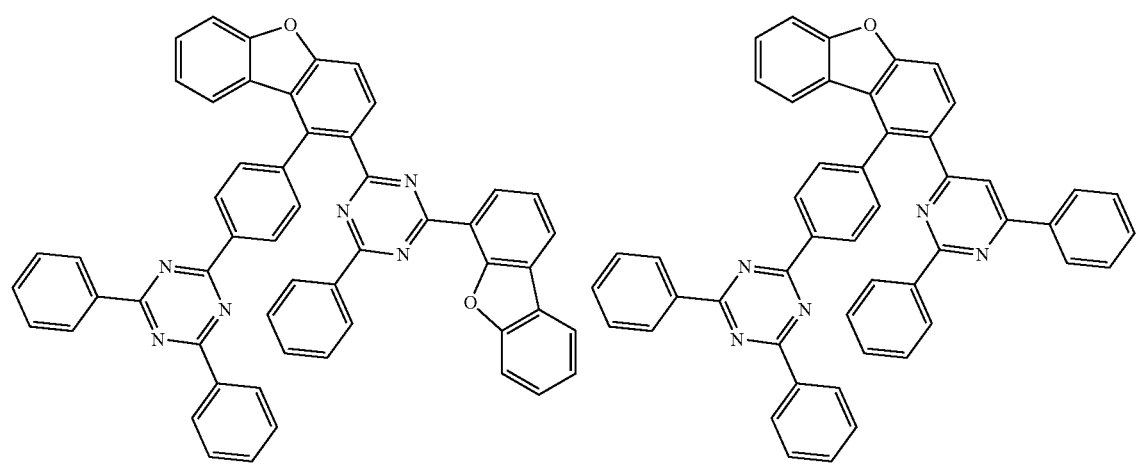
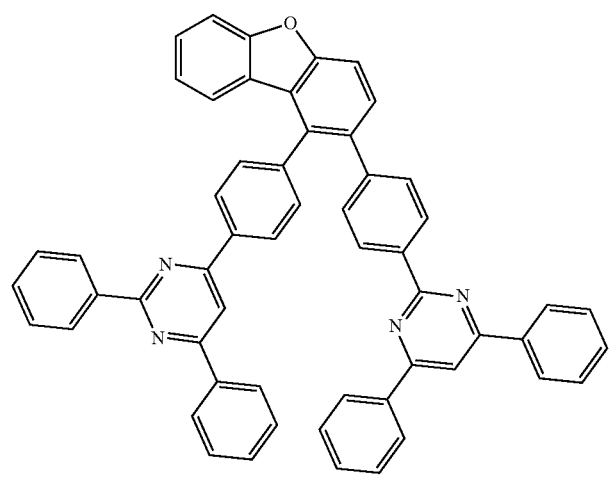 [SMILES: c1ccc(-c2cc(-c3ccc(-c4c(-c5ccc(-c6nc(-c7ccccc7)cc(-c7ccccc7)n6)cc5)ccc5oc6ccccc6c45)cc3)nc(-c3ccccc3)n2)cc1]

45
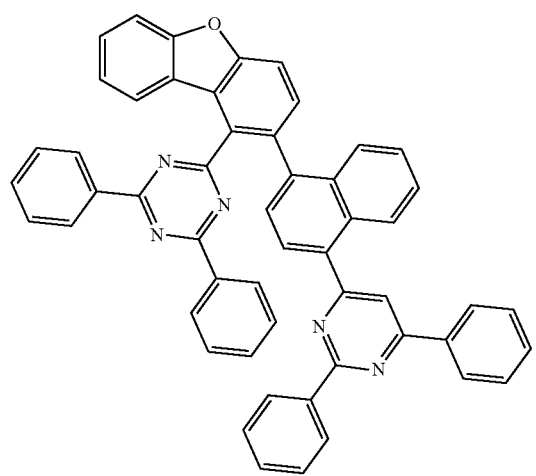
46
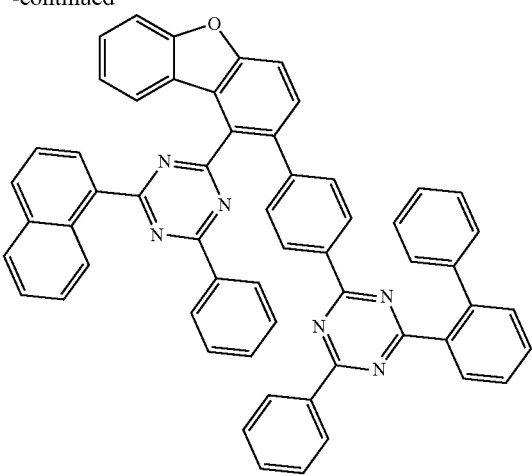
-continued
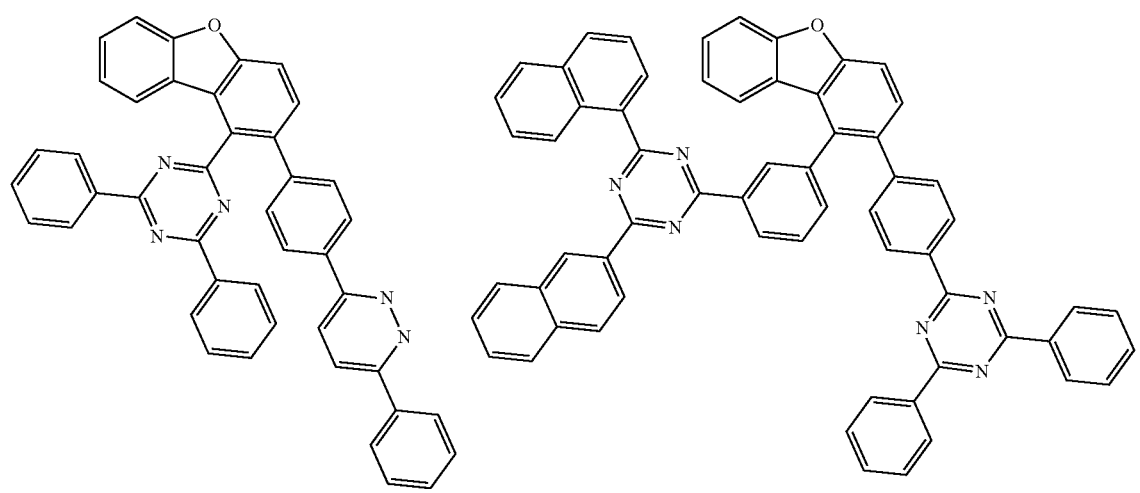
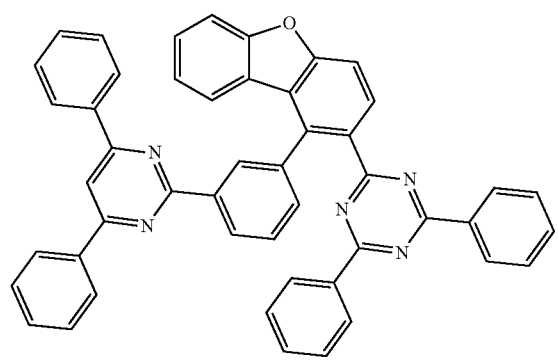

-continued
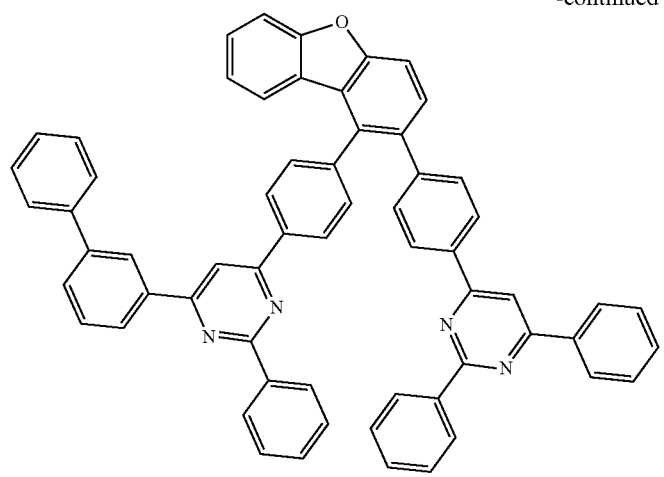
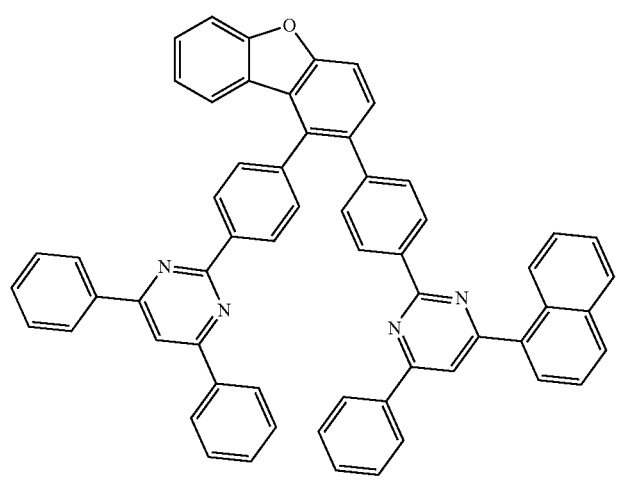
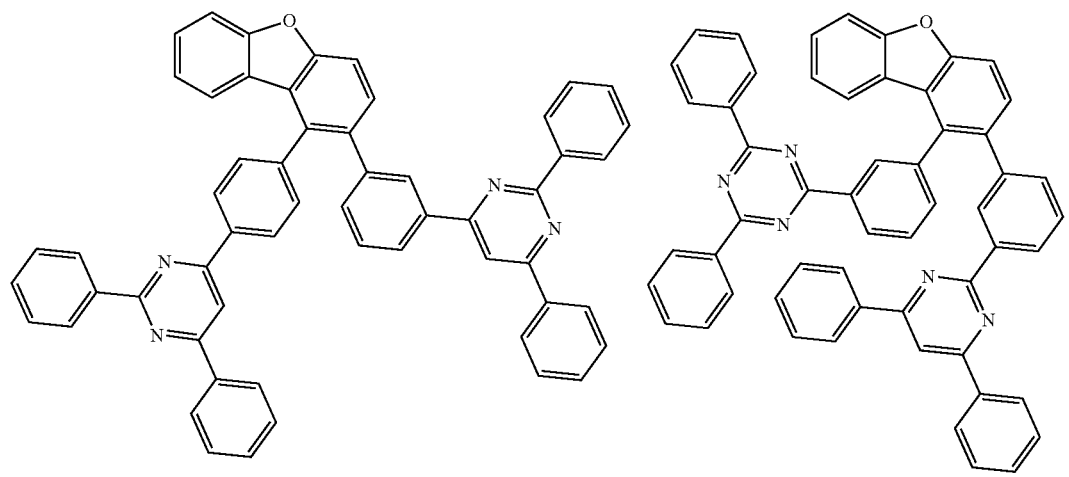

-continued
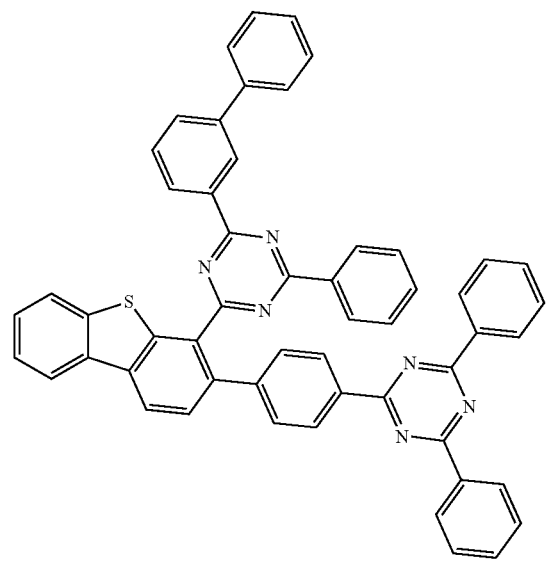
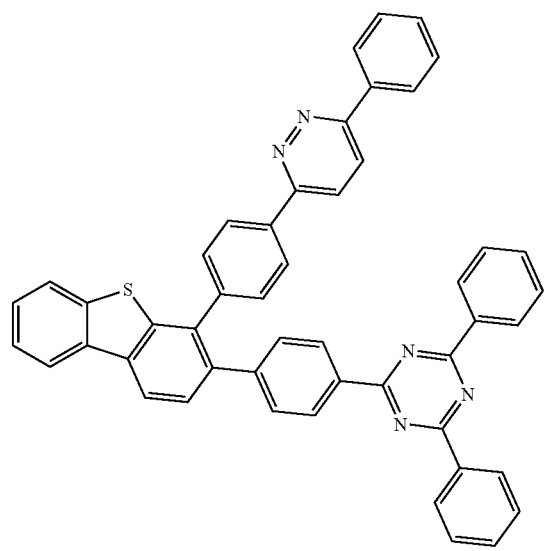
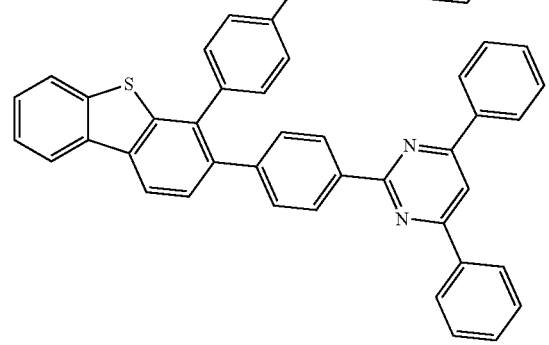
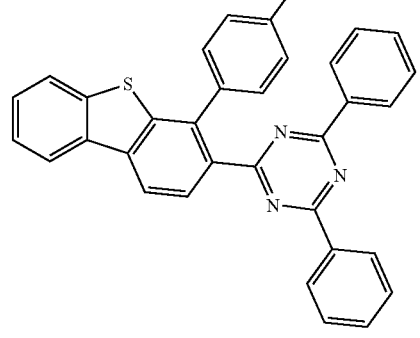
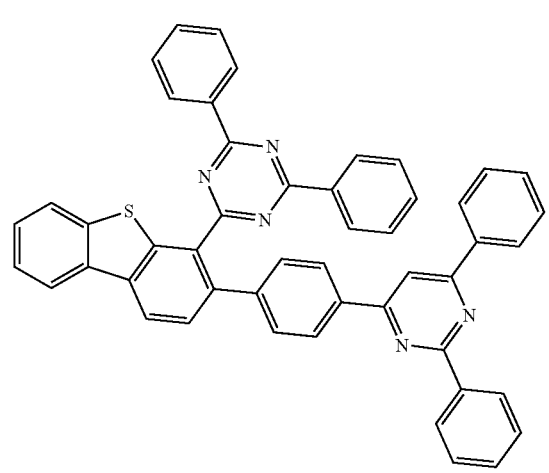
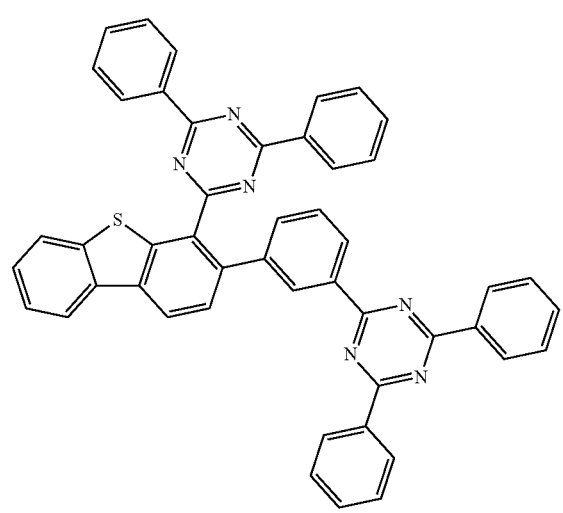

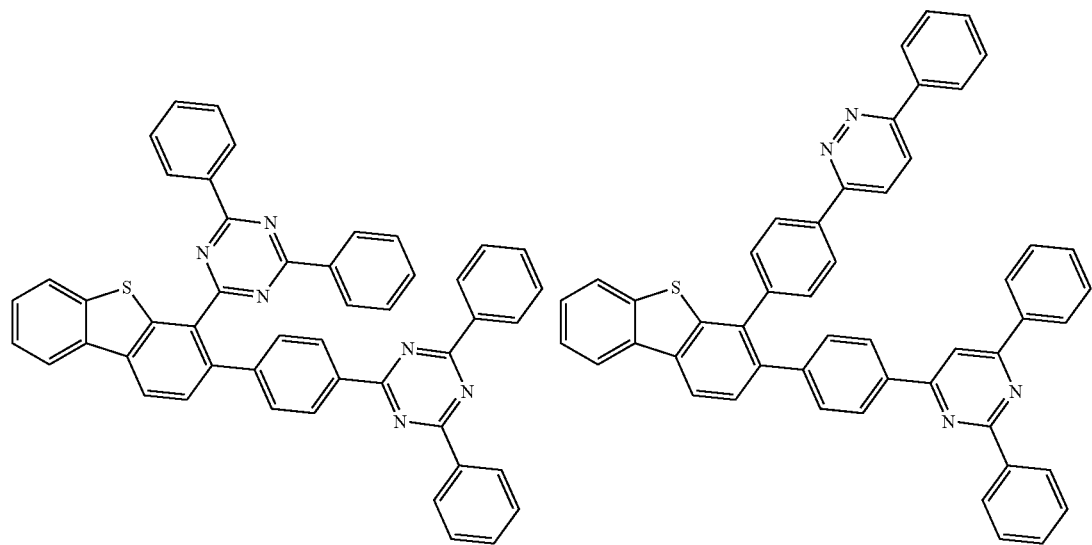
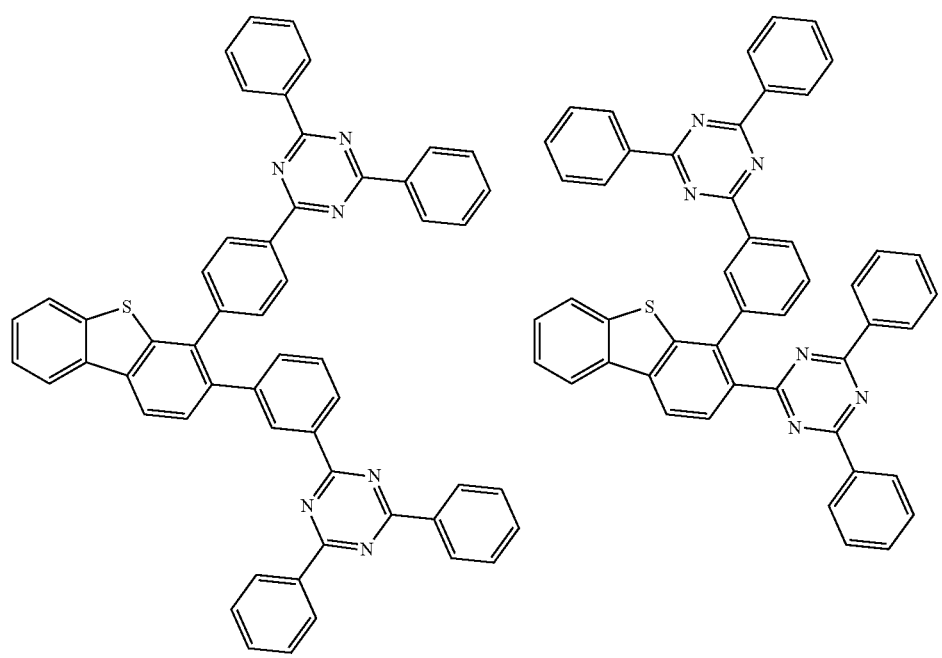
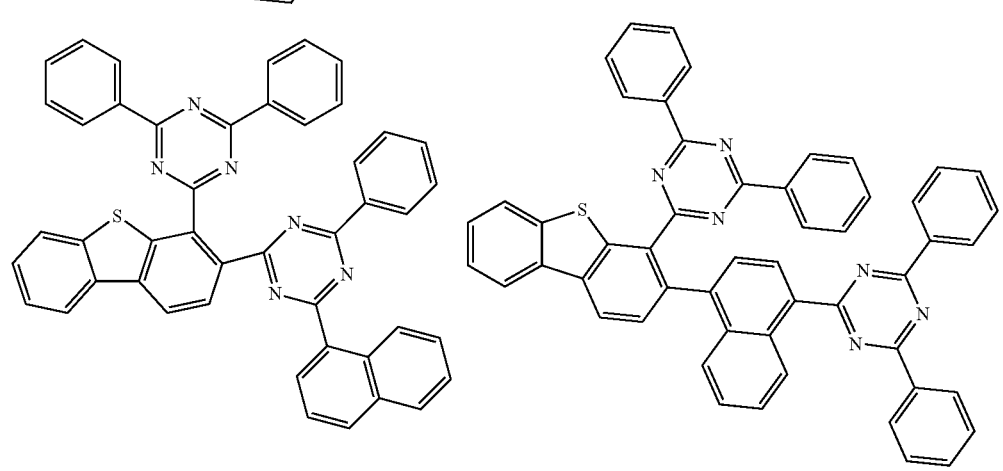

-continued
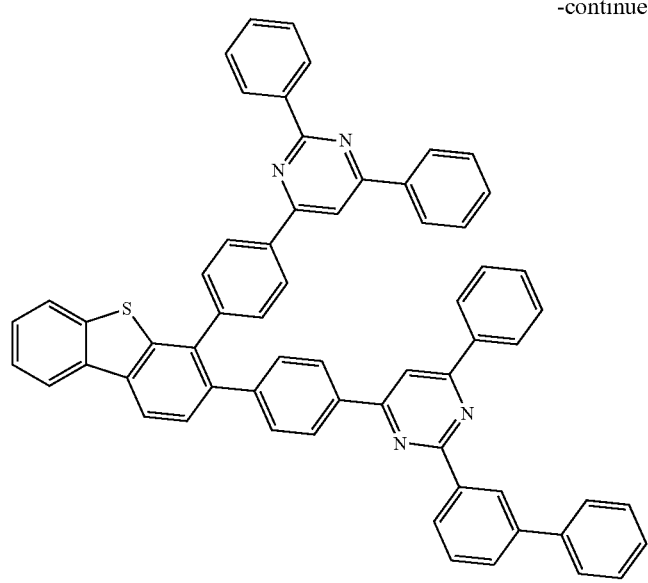
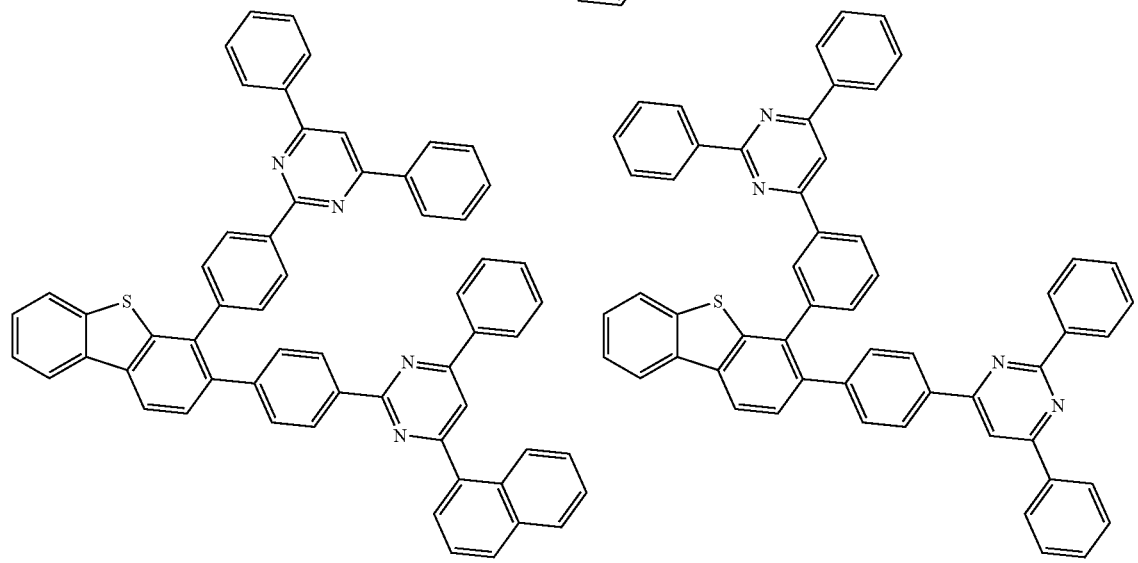
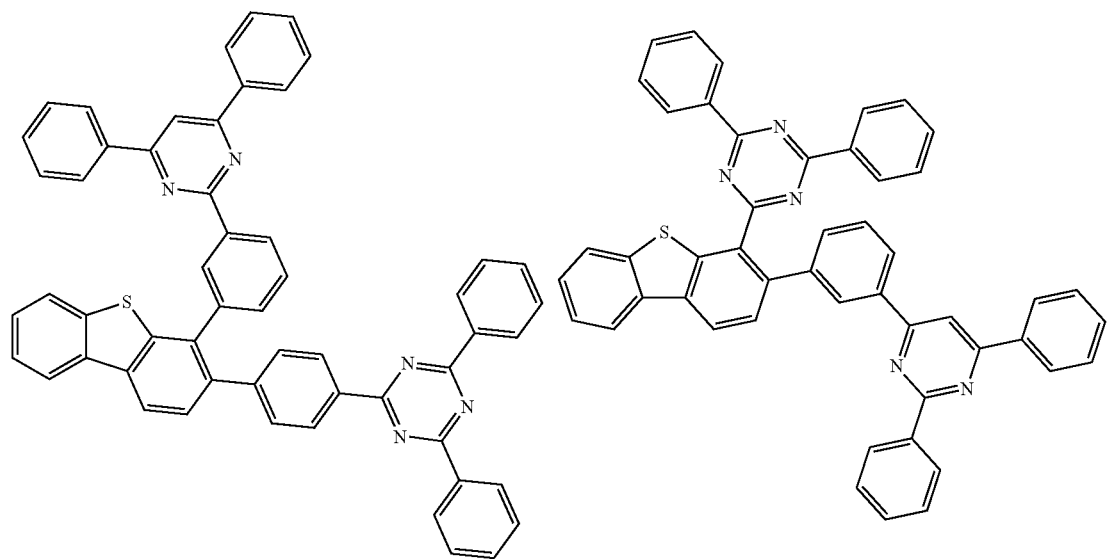

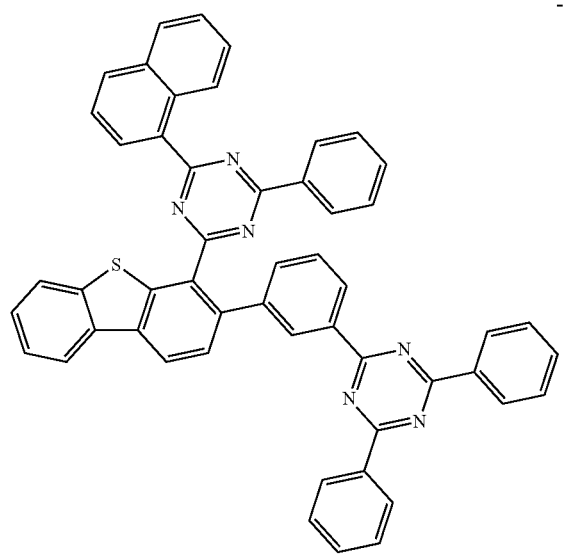
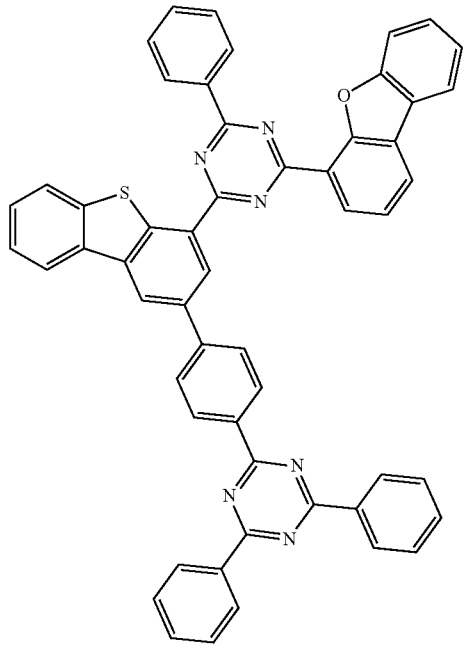
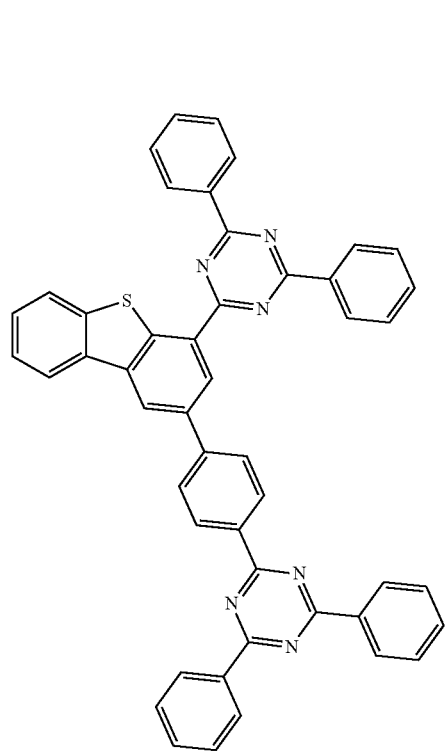
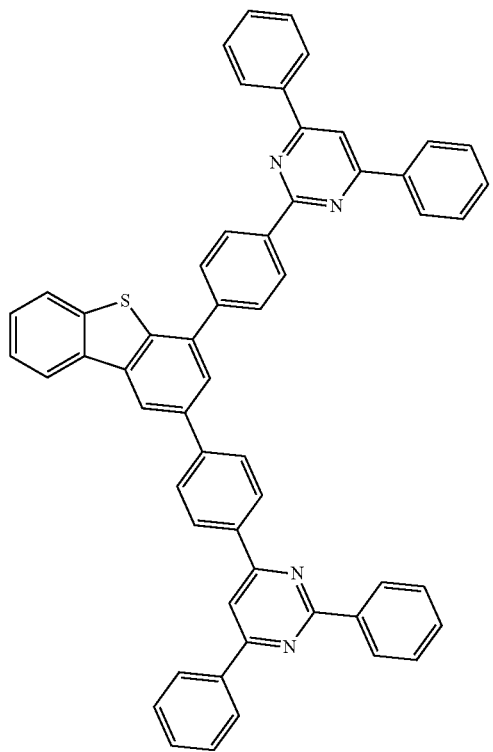

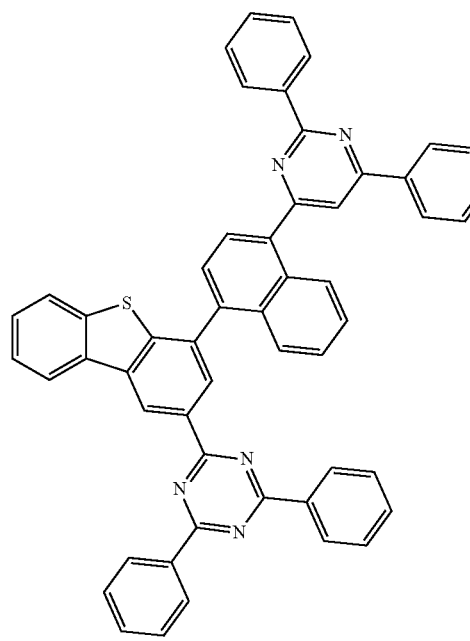
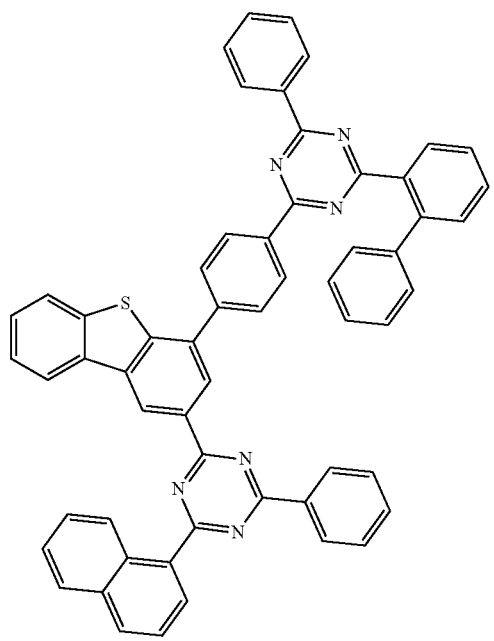
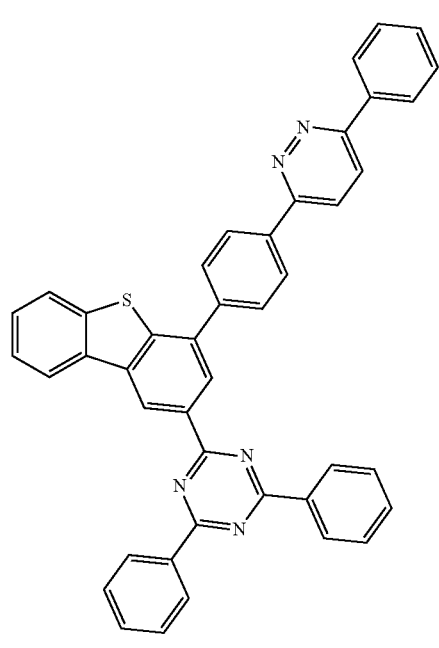
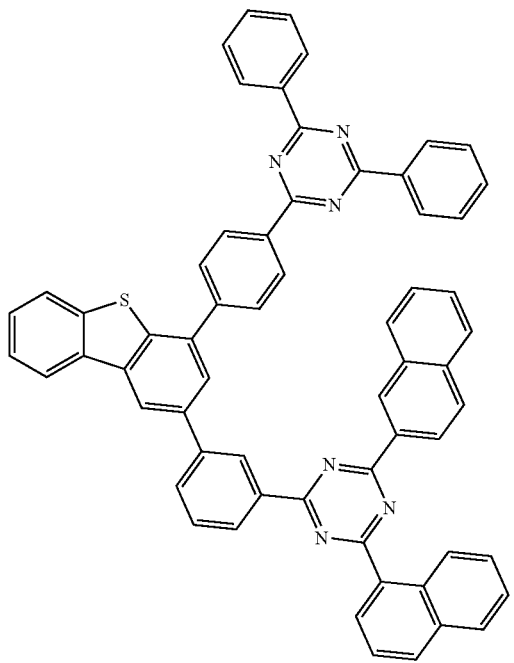

-continued
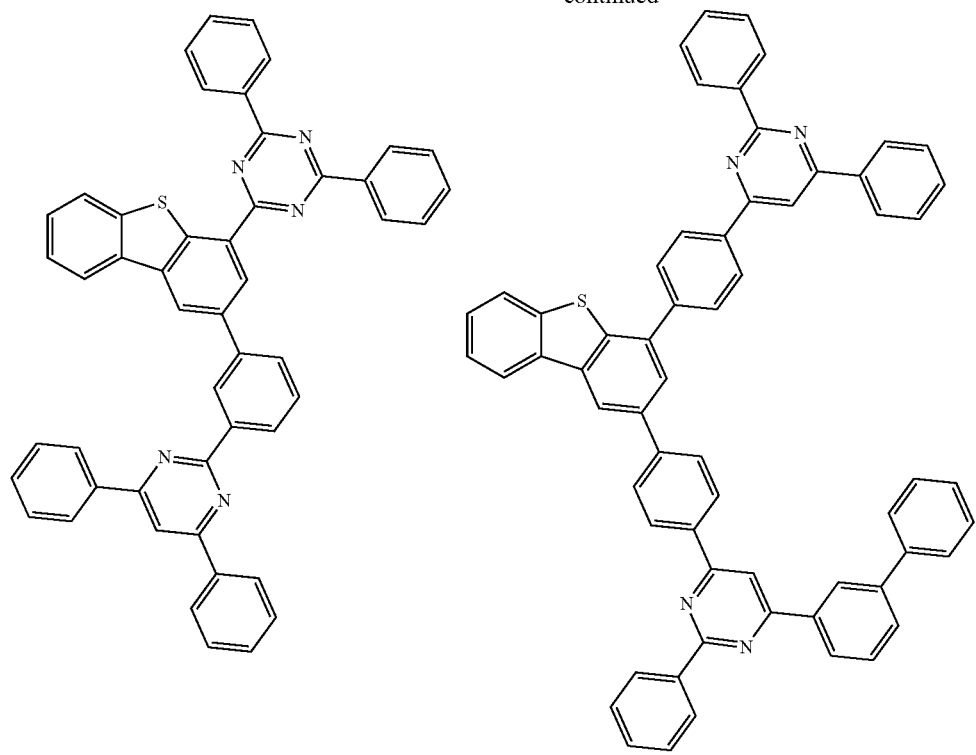
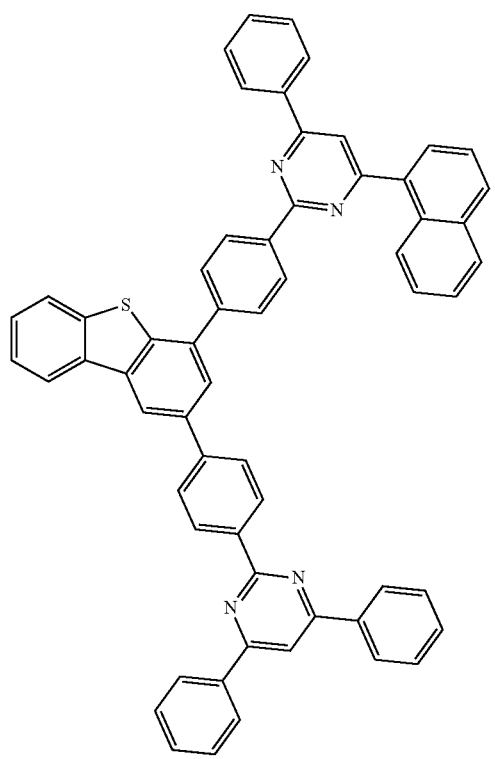

61
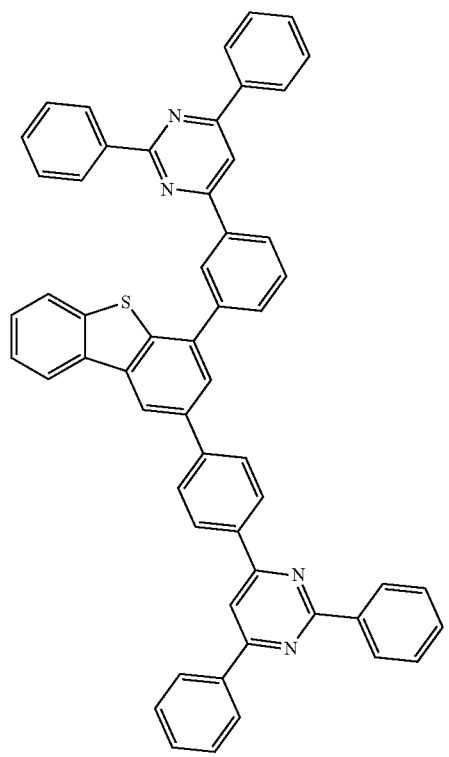
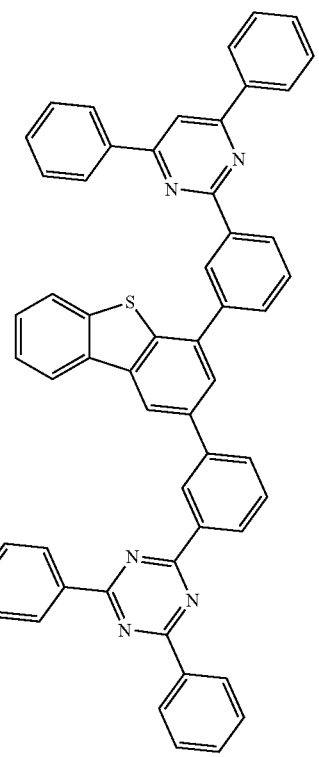
62
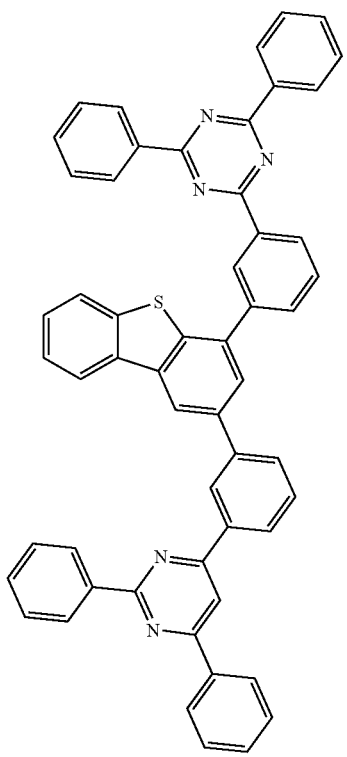
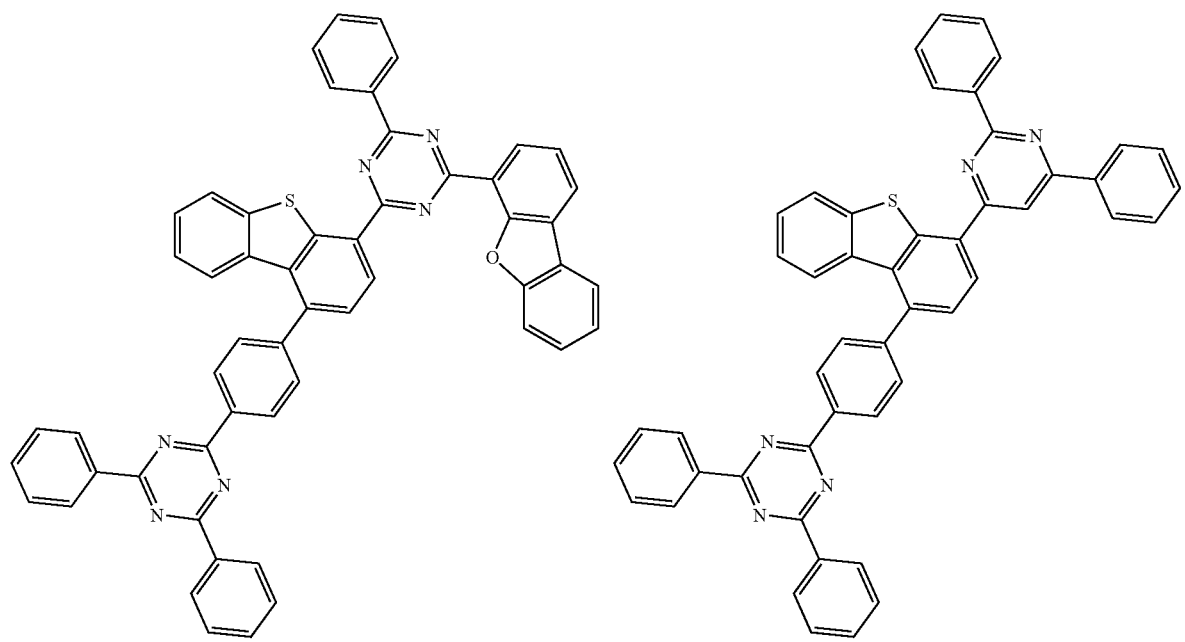

-continued
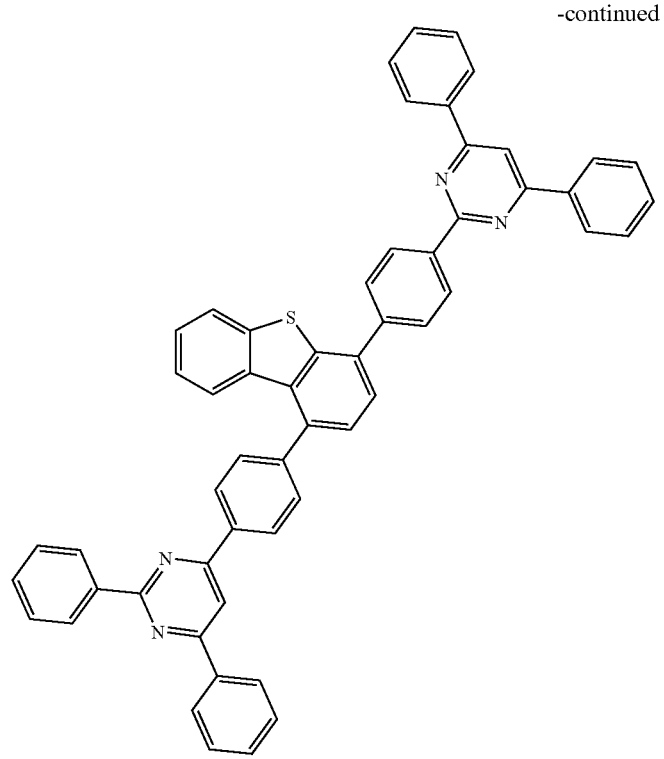
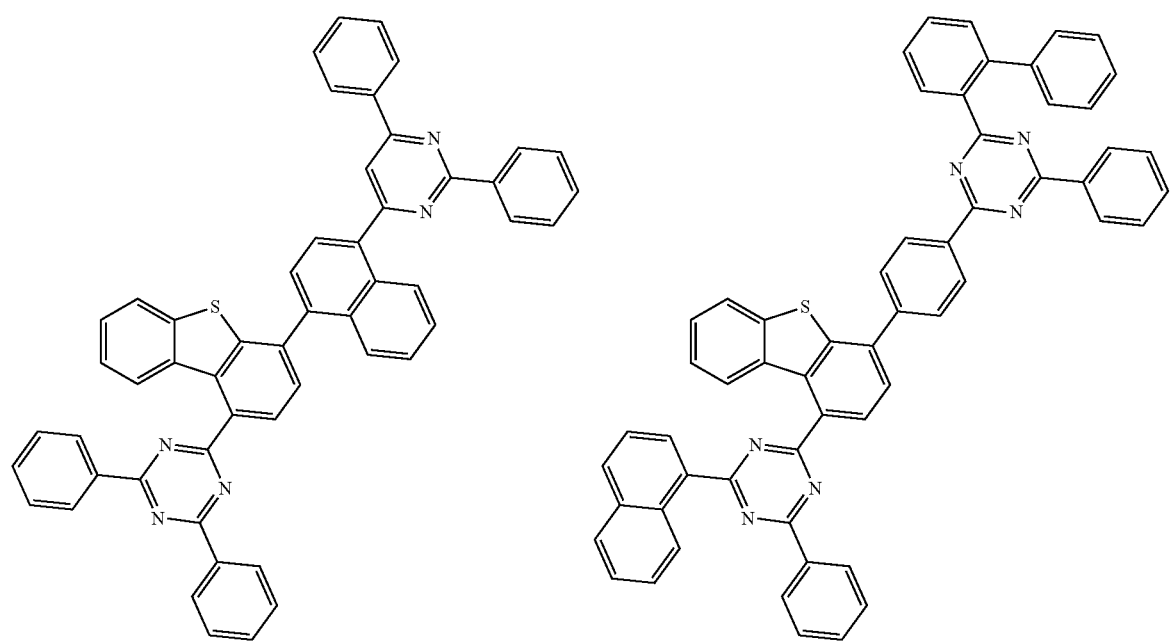

-continued
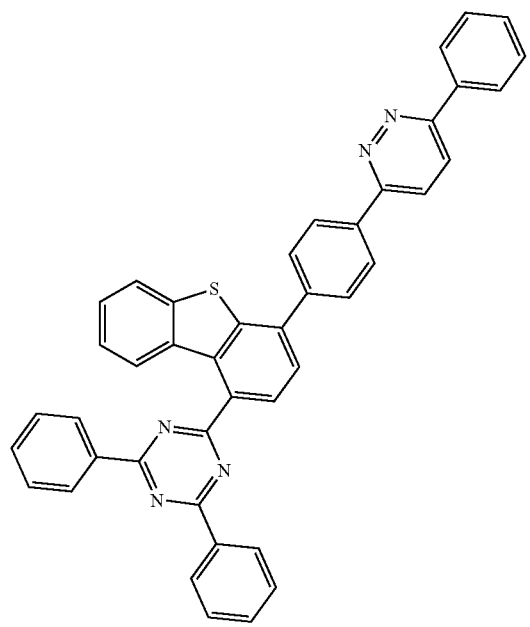
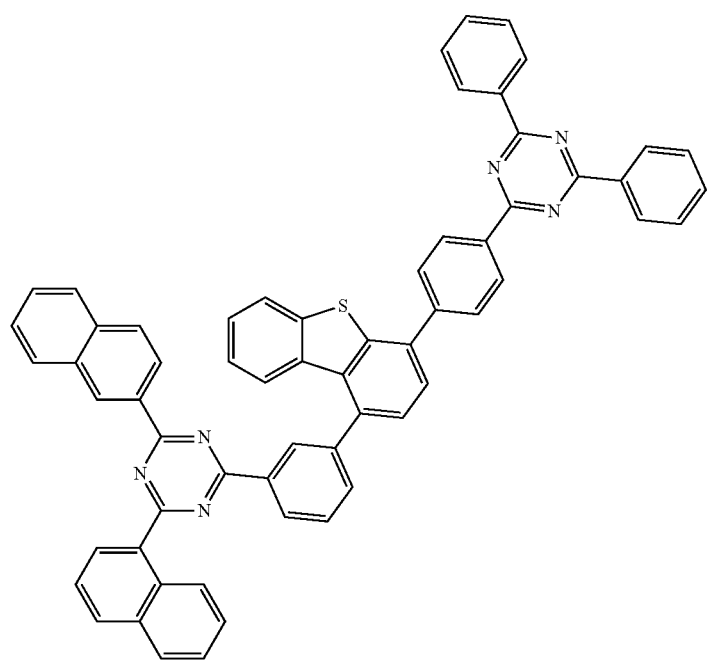

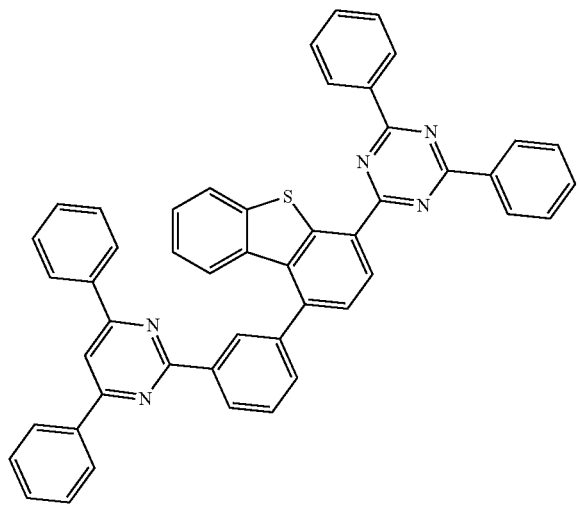
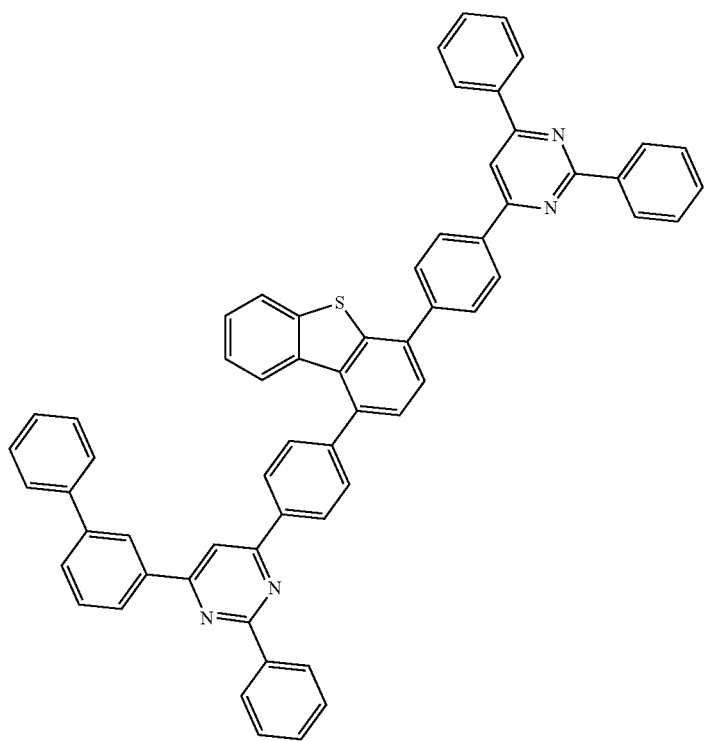

-continued
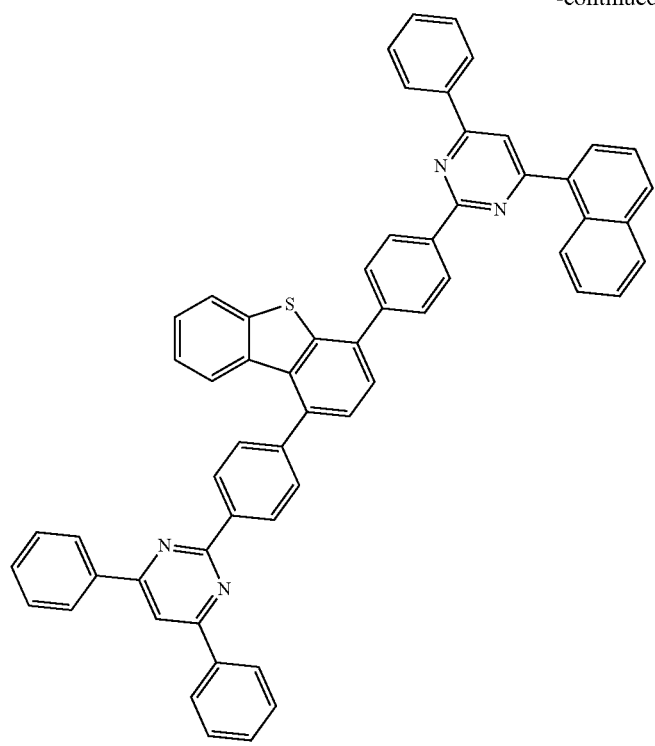
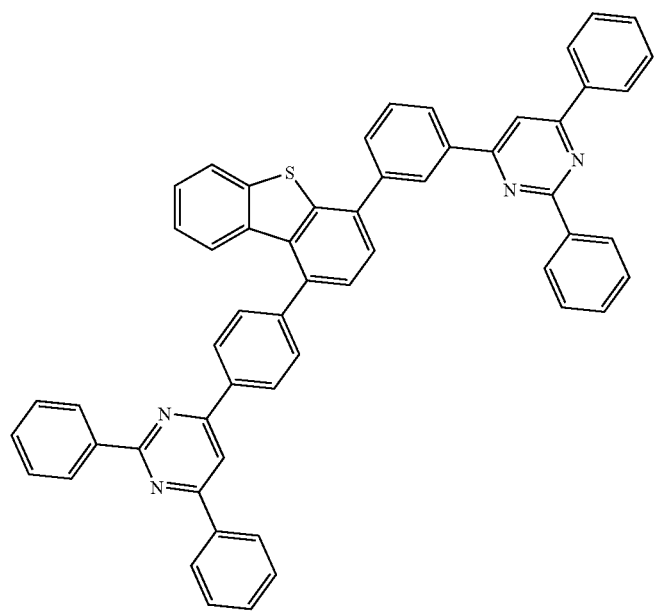

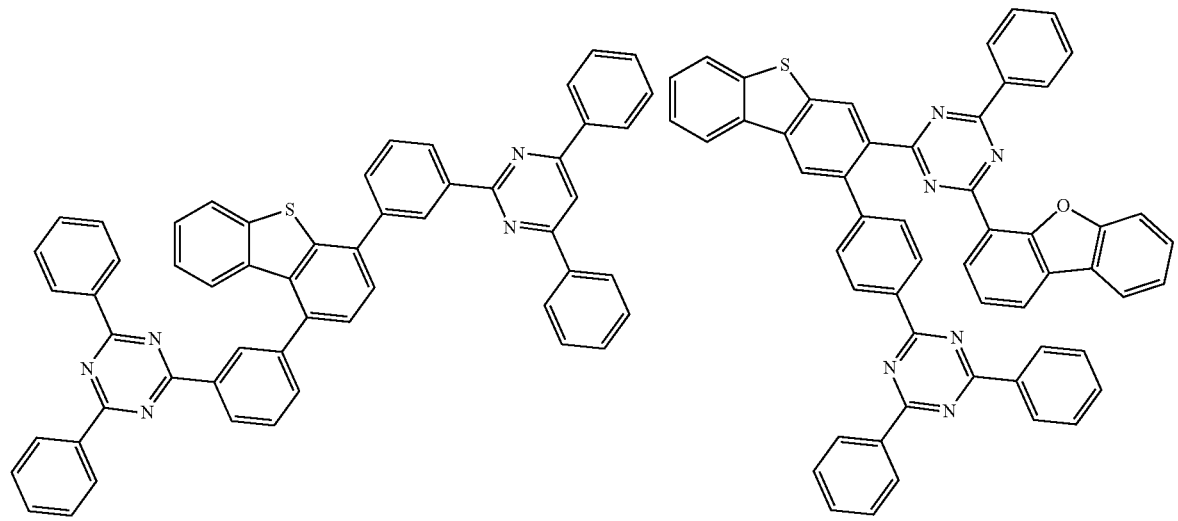
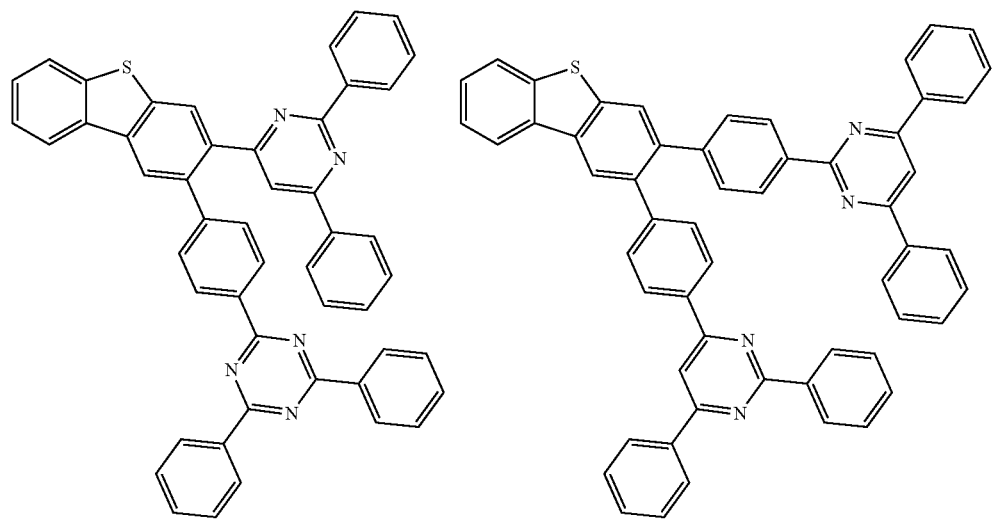
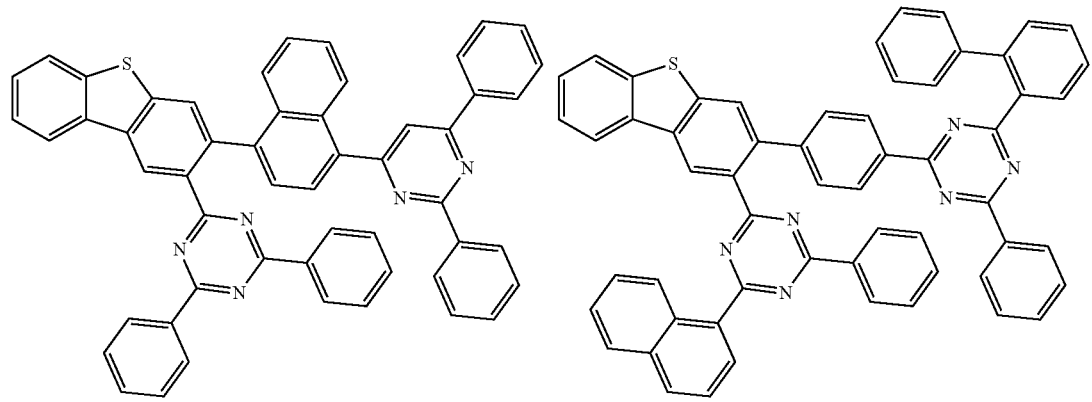

-continued
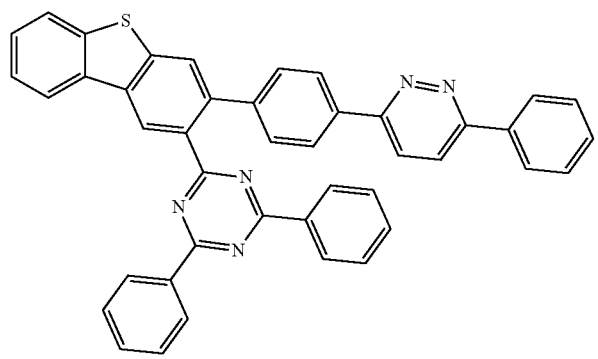
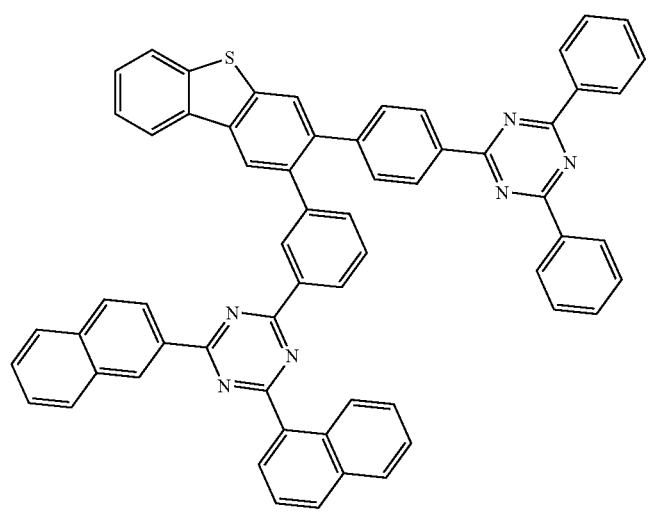
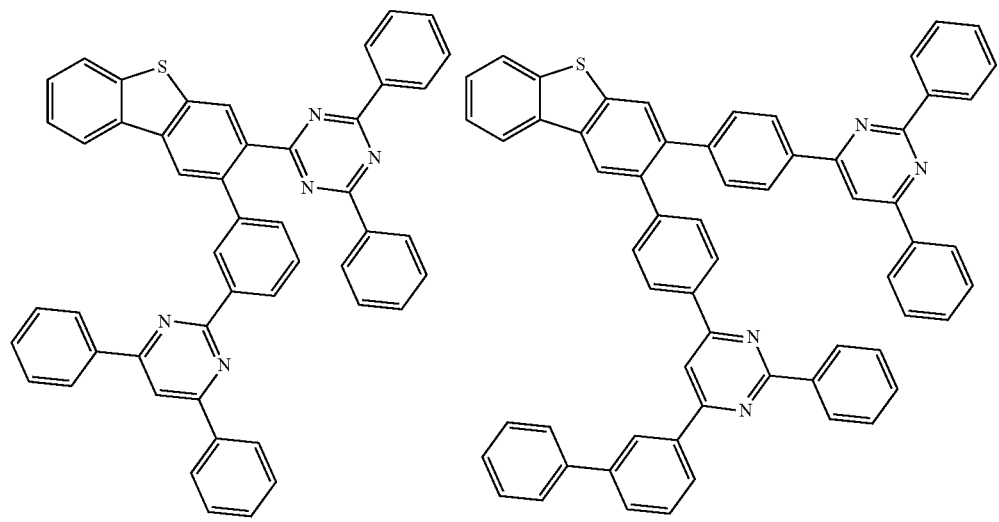

-continued
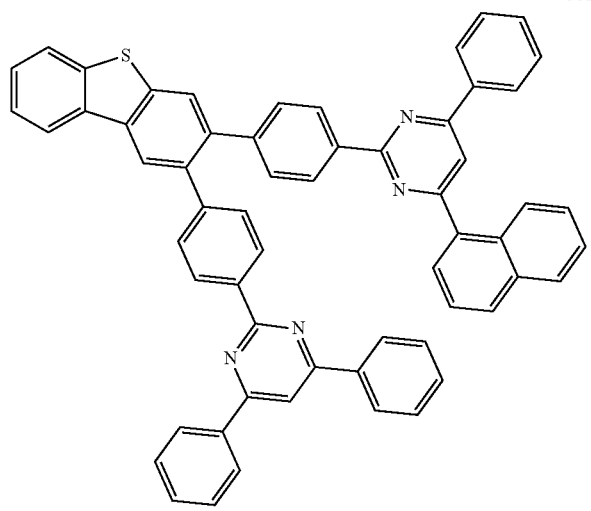
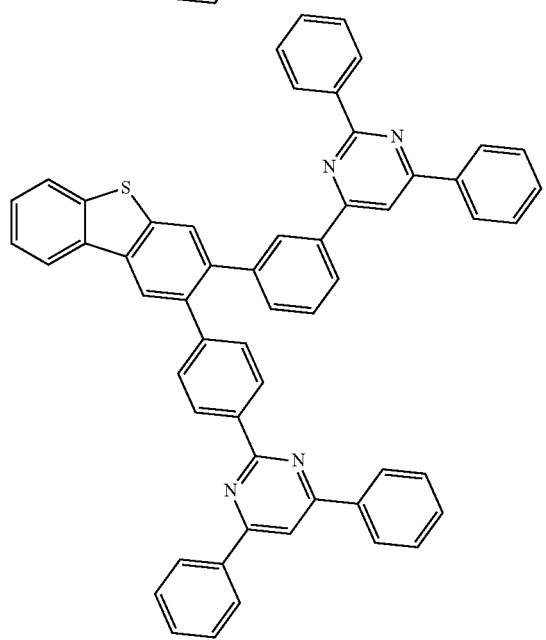
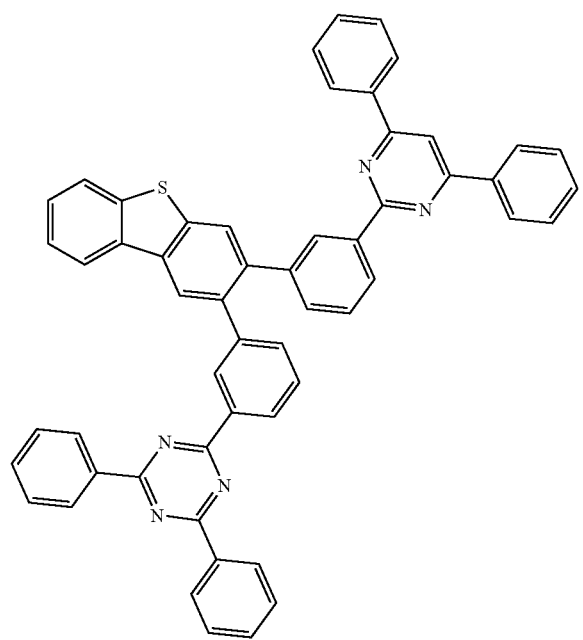
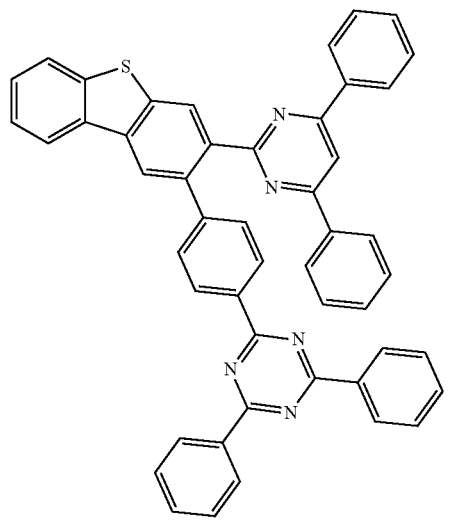
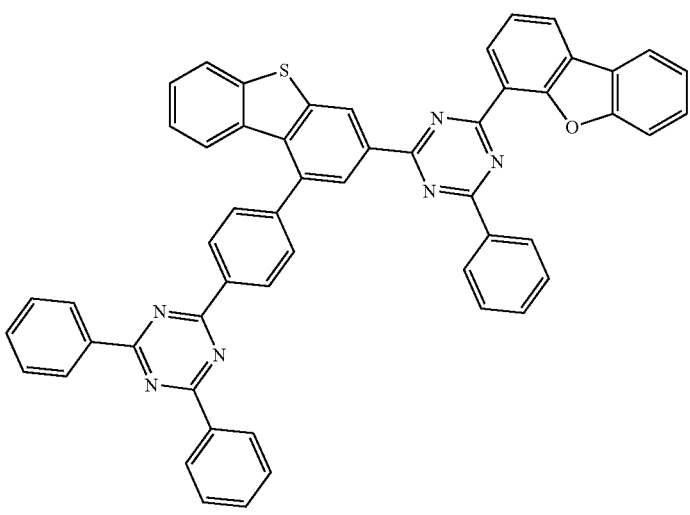

-continued
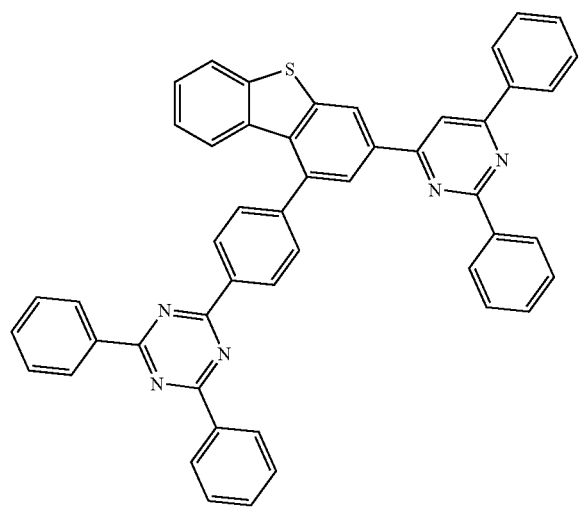
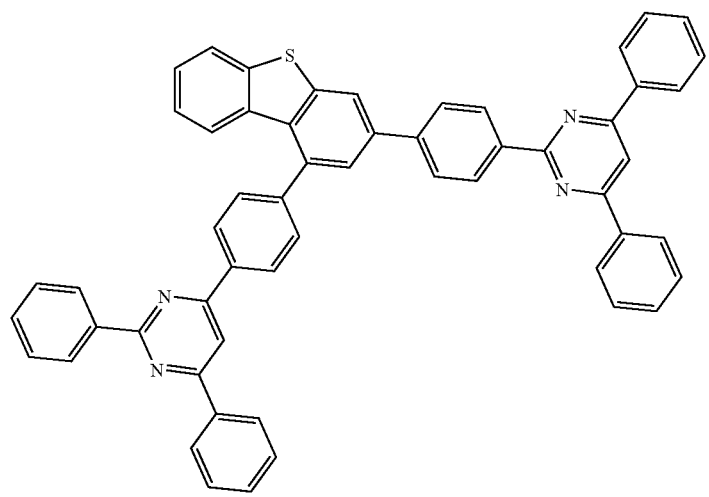
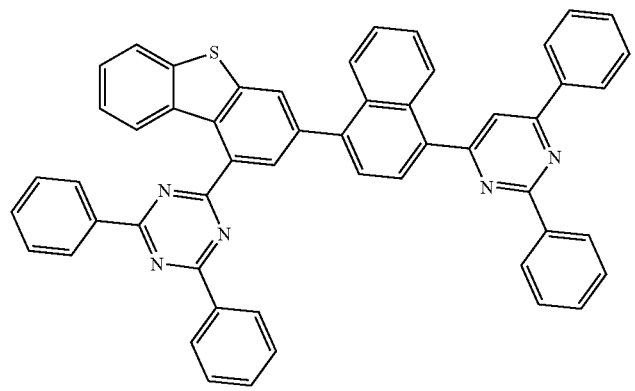

-continued
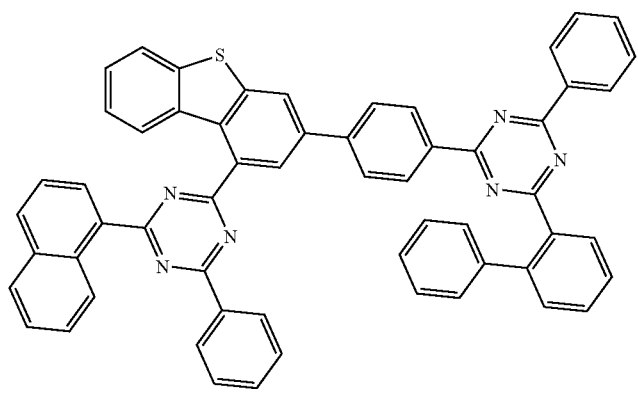
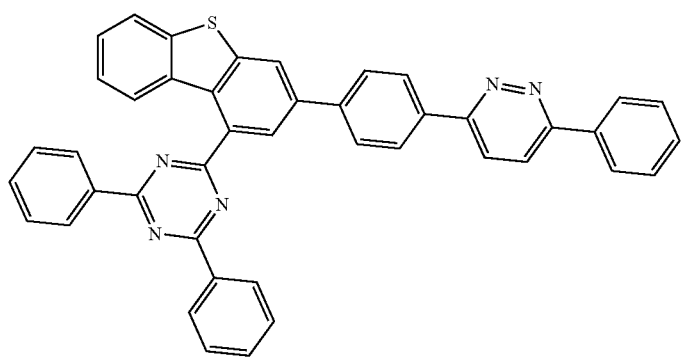
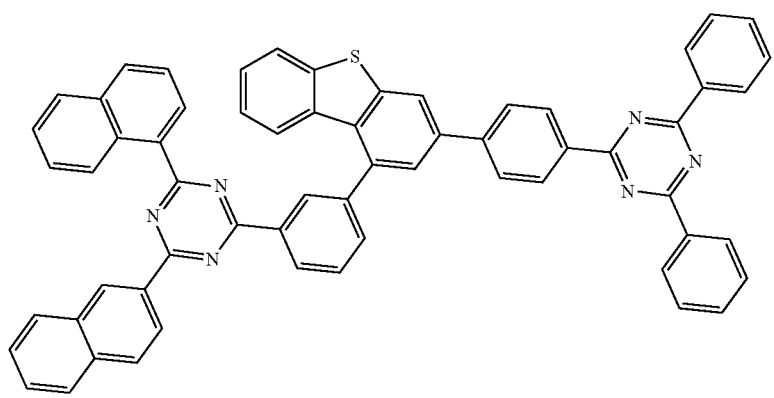
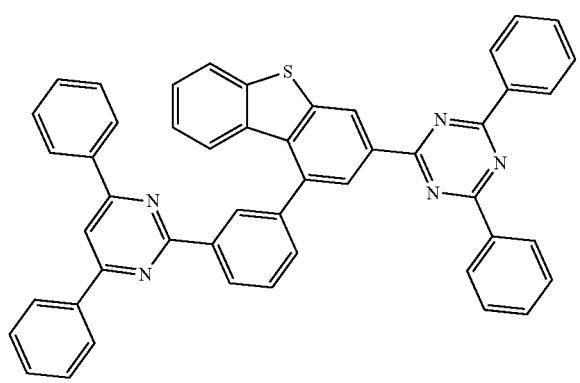

-continued
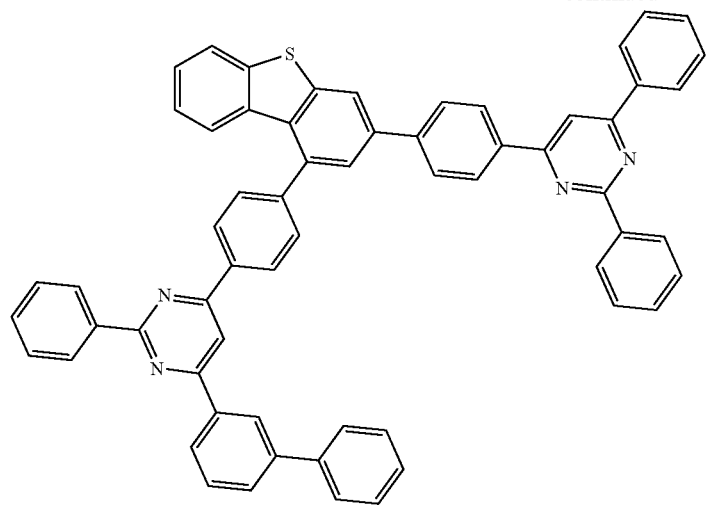
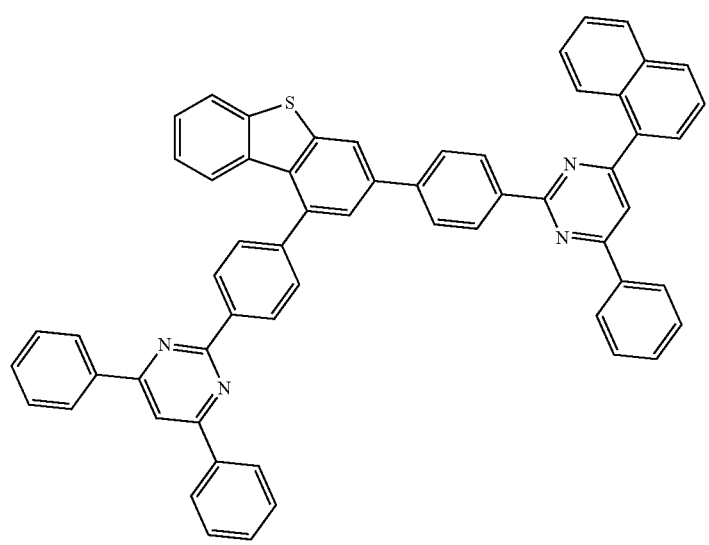
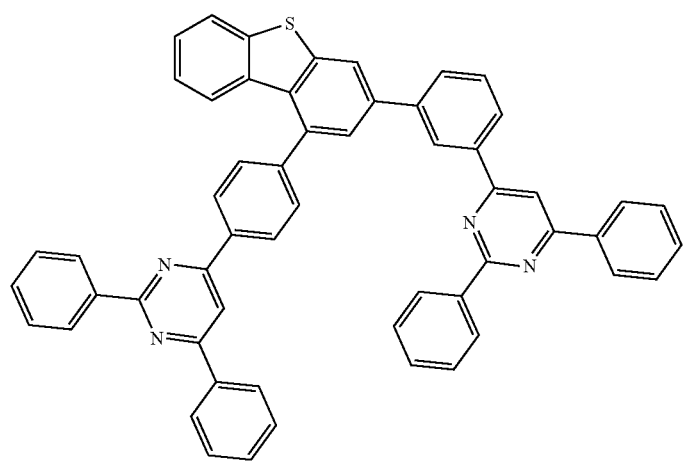

83
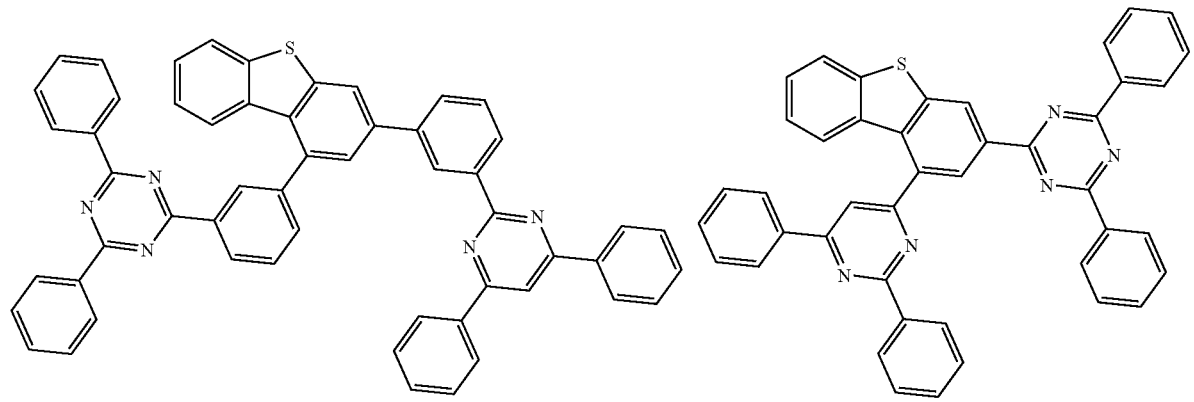
84
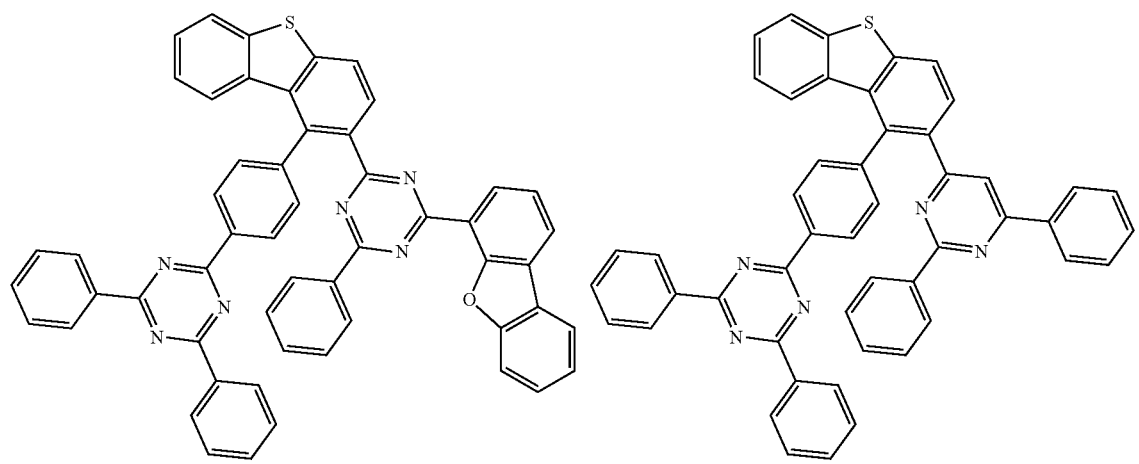
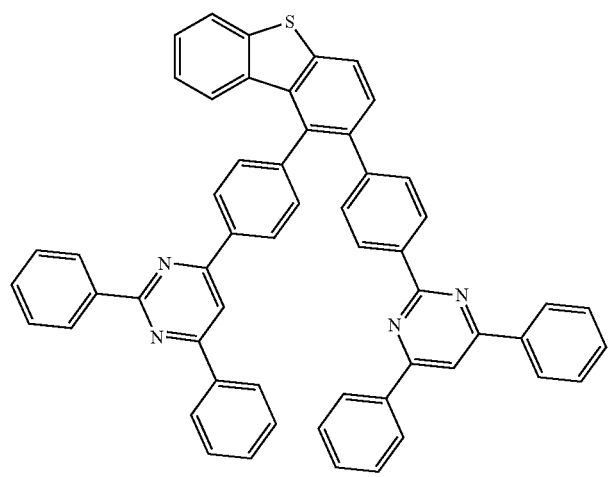

85
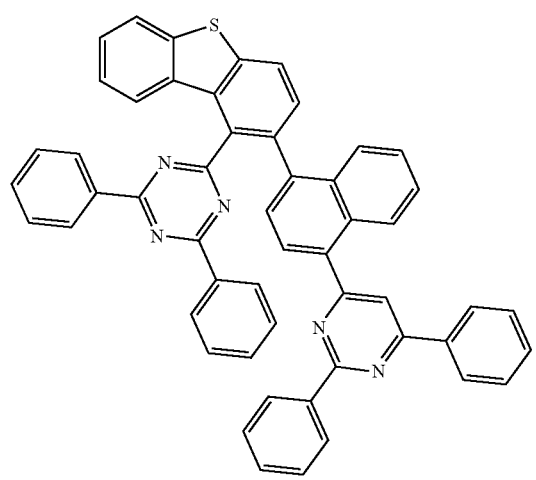
86
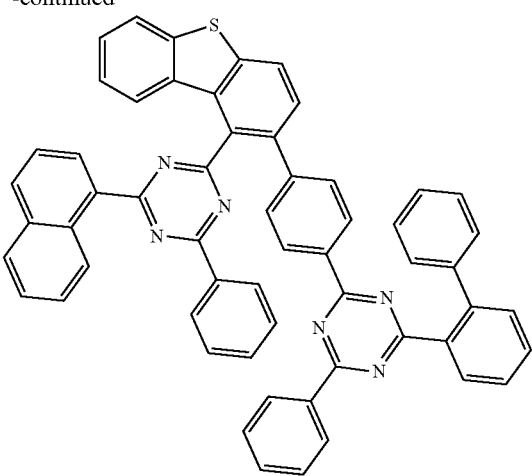
-continued
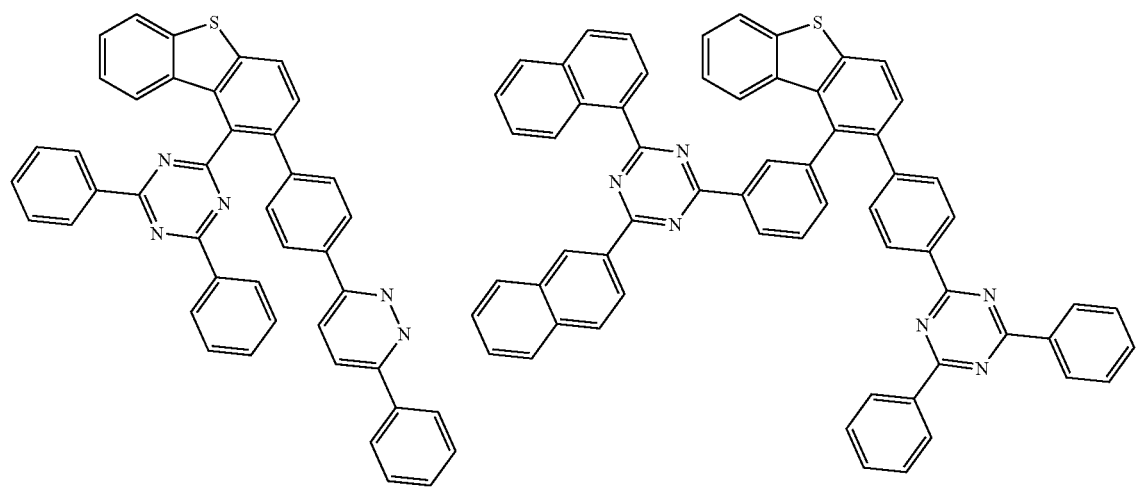
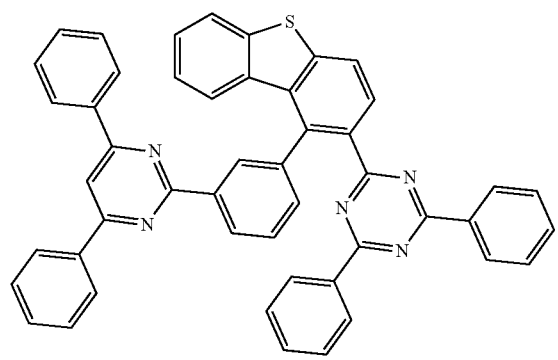

87
88
-continued
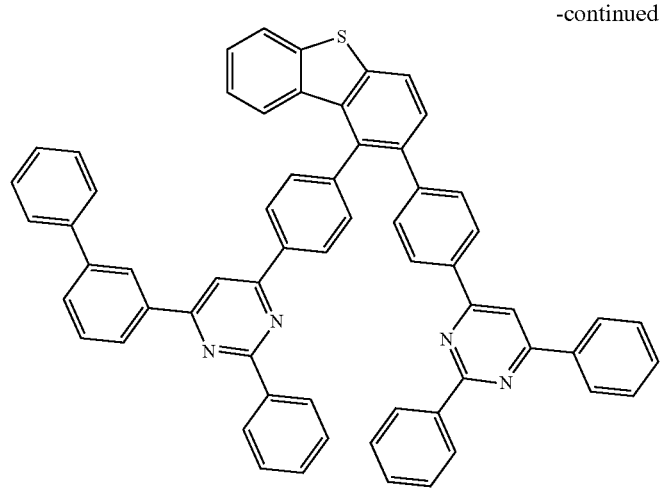
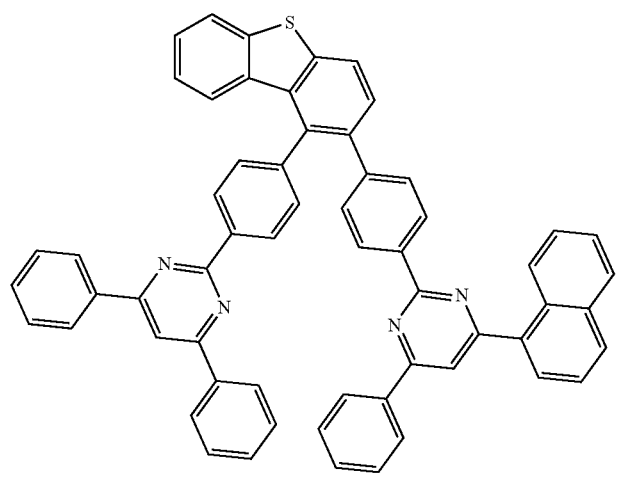
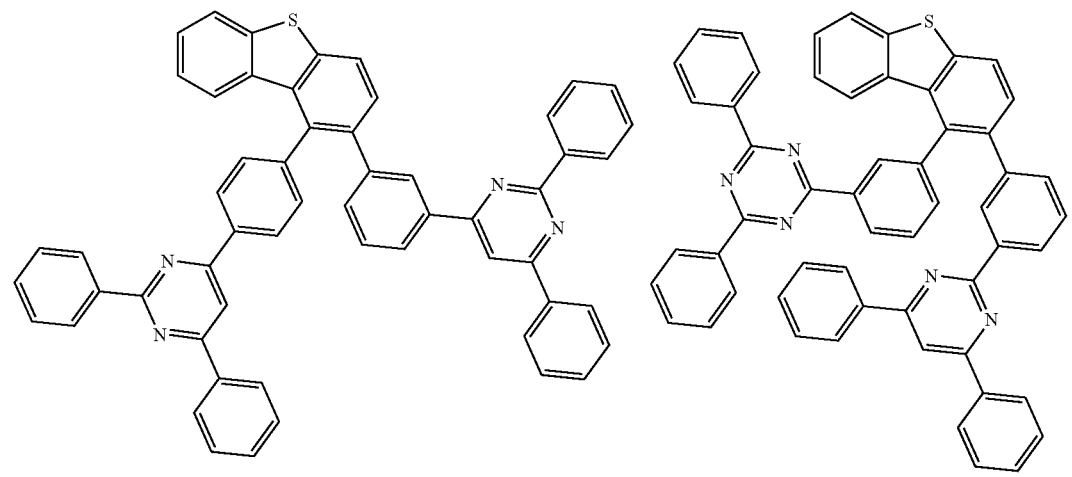

The compound represented by Chemical Formula 1 may be prepared according to the preparation method as shown in Reaction Schemes 1 below.

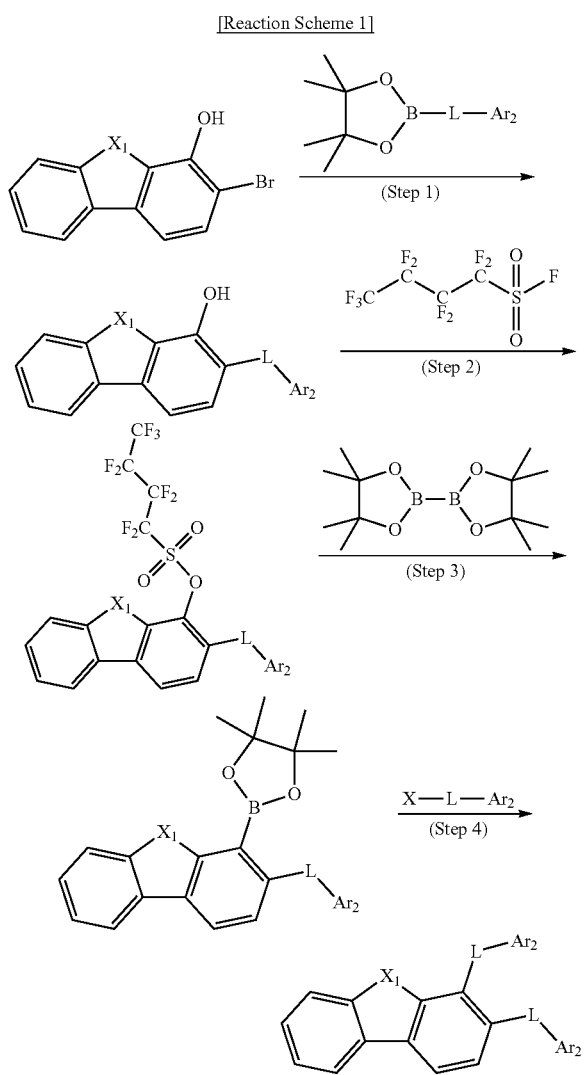

[Reaction Scheme 1]

The Reaction Scheme 1 illustrates that, in the Formula 1, $R_1$ and $R_2$ are -L-$Ar_2$, and $R_3$ and $R_4$ are hydrogen. In the Reaction Scheme 1, the definitions other than X are as defined in Formula 1, and X is halogen, preferably bromo. The preparation method can be further specified in the preparation examples to be described later.

In addition, the present disclosure provides an organic light emitting device comprising the compound represented by Chemical Formula 1. In one example, the present disclosure provides an organic light emitting device comprising a first electrode; a second electrode provided at a side opposite to the first electrode; and at least one layer of organic material layers provided between the first electrode and the second electrode, wherein the at least one layer of the organic material layers includes a compound represented by the Chemical Formula 1.

The organic material layer of the organic light emitting device of the present disclosure may have a single layer structure, but it may have a multilayered structure in which two or more organic material layers are stacked. For example, the organic light emitting device of the present disclosure may have a structure comprising a hole injection layer, a hole transport layer, a light emitting layer, an electron transport layer, an electron injection layer and the like as the organic material layer. However, the structure of the organic light emitting device is not limited thereto, and it may include a smaller number of organic layers.

Further, the organic material layer may include a hole injection layer, a hole transport layer, or a layer simultaneously performing hole injection and transport, wherein the hole injection layer, the hole transport layer, and the layer simultaneously performing hole injection and transport include a compound represented by the Chemical Formula 1.

Further, the organic material layer may include a light emitting layer, wherein the light emitting layer includes a compound represented by the Chemical Formula 1.

Further, the organic material layer may include an electron transport layer or an electron injection layer, wherein the electron transport layer or the electron injection layer includes a compound represented by the Chemical Formula 1.

Further, the electron transport layer, the electron injection layer and the layer simultaneously performing an electron injection and an electron transport include a compound represented by the Chemical Formula 1.

Further, the organic material layer may include a light emitting layer and an electron transport layer, wherein the electron transport layer may include a compound represented by the Chemical Formula 1.

Further, the organic light emitting device according to the present disclosure may be a normal type organic light emitting device in which an anode, at least one organic material layer, and a cathode are sequentially stacked on a substrate. Further, the organic light emitting device according to the present disclosure may be an inverted type organic light emitting device in which a cathode, at least one organic material layer and an anode are sequentially stacked on a substrate. For example, the structure of an organic light emitting device according to an embodiment of the present disclosure is illustrated in FIGS. 1 and 2.

FIG. 1 shows an example of an organic light emitting device comprising a substrate 1, an anode 2, a light emitting layer 3, and a cathode 4. In such a structure, the compound represented by the Chemical Formula 1 may be included in the light emitting layer.

FIG. 2 shows an example of an organic light emitting device comprising a substrate 1, an anode 2, a hole injection layer 5, a hole transport layer 6, a light emitting layer 7, an electron transport layer 8, and a cathode 4. In such a structure, the compound represented by the Chemical Formula 1 may be included in at least one layer of the hole injection layer, the hole transport layer, the light emitting layer and the electron transport layer.

The organic light emitting device according to the present disclosure may be manufactured by materials and methods known in the art, except that at least one layer of the organic material layers includes the compound represented by the Chemical Formula 1. In addition, when the organic light emitting device includes a plurality of organic material layers, the organic material layers may be formed of the same material or different materials.

For example, the organic light emitting device according to the present disclosure can be manufactured by sequentially stacking a first electrode, an organic material layer and a second electrode on a substrate. In this case, the organic light emitting device may be manufactured by depositing a metal, metal oxides having conductivity, or an alloy thereof on the substrate by using a PVD (physical vapor deposition) method such as a sputtering method or an e-beam evaporation method to form the anode, forming an organic material layer including the hole injection layer, the hole transport layer, the light emitting layer, and the electron transport layer thereon, and then depositing a material that can be used as the cathode thereon. In addition to such a method, the organic light emitting device may be manufactured by sequentially depositing a cathode material, an organic material layer and an anode material on a substrate.

In addition, the compound represented by the Chemical Formula 1 may be formed into an organic layer by a solution coating method as well as a vacuum deposition method at the time of manufacturing an organic light emitting element. Herein, the solution coating method means a spin coating, a dip coating, a doctor blading, an inkjet printing, a screen printing, a spray method, a roll coating, or the like, but is not limited thereto.

In addition to such a method, the organic light emitting device may be manufactured by sequentially depositing a cathode material, an organic material layer, and an anode material on a substrate (International Publication WO 2003/012890). However, the manufacturing method is not limited thereto.

For example, the first electrode is an anode and the second electrode is a cathode, or the first electrode is a cathode and the second electrode is an anode.

As the anode material, generally, a material having a large work function is preferably used so that holes can be smoothly injected into the organic material layer. Specific examples of the anode material include metals such as vanadium, chrome, copper, zinc, and gold, or an alloy thereof; metal oxides such as zinc oxides, indium oxides, indium tin oxides (ITO), and indium zinc oxides (IZO); a combination of metals and oxides, such as ZnO:Al or $SNO_2$:Sb; conductive polymers such as poly(3-methylthiophene), poly[3,4-(ethylene-1,2-dioxy)thiophene](PEDOT), polypyrrole, and polyaniline, and the like, but are not limited thereto.

As the cathode material, generally, a material having a small work function is preferably used so that electrons can be easily injected into the organic material layer. Specific examples of the cathode material include metals such as magnesium, calcium, sodium, potassium, titanium, indium, yttrium, lithium, gadolinium, aluminum, silver, tin, and lead, or an alloy thereof; a multilayered structure material such as LiF/Al or $LiO_2$/Al, and the like, but are not limited thereto.

The hole injection layer is a layer for injecting holes from the electrode, and the hole injection material is preferably a compound which has an ability of transporting the holes, a hole injecting effect in the anode and an excellent hole injecting effect to the light emitting layer or the light emitting material, prevents movement of an exciton generated in the light emitting layer to the electron injection layer or the electron injection material, and has an excellent thin film forming ability. It is preferable that a HOMO (highest occupied molecular orbital) of the hole injection material is between the work function of the anode material and a HOMO of a peripheral organic material layer. Specific examples of the hole injection material include metal porphyrine, oligothiophene, an arylamine-based organic material, a hexanitrilehexaazatriphenylene-based organic material, a quinacridone-based organic material, a perylene-based organic material, anthraquinone, polyaniline and polythiophene-based conductive polymer, and the like, but are not limited thereto.

The hole transport layer is a layer that receives holes from a hole injection layer and transports the holes to the light emitting layer. The hole transport material is suitably a material having large mobility to the holes, which may receive holes from the anode or the hole injection layer and transfer the holes to the light emitting layer. Specific examples thereof include an arylamine-based organic material, a conductive polymer, a block copolymer in which a conjugate portion and a non-conjugate portion are present together, and the like, but are not limited thereto.

The light emitting material is a material capable of emitting light in the visible light region by combining holes and electrons respectively transported from the hole transport layer and the electron transport layer, and having good quantum efficiency for fluorescence or phosphorescence. Specific examples include 8-hydroxy-quinoline aluminum complex ($Alq_3$); carbazole-based compounds; dimerized styryl compounds; BAlq; 10-hydroxybenzoquinoline-metal compounds; benzoxazole, benzothiazole and benzimidazole-based compounds; poly(p-phenylenevinylene)(PPV)-based polymers; spiro compounds; polyfluorene, rubrene, and the like, but are not limited thereto.

The light emitting layer may include a host material and a dopant material. The host material may be a fused aromatic ring derivative, a heterocycle-containing compound or the like. Specific examples of the fused aromatic ring derivatives include anthracene derivatives, pyrene derivatives, naphthalene derivatives, pentacene derivatives, phenanthrene compounds, and fluoranthene compounds. Examples of heterocyclic compounds include carbazole derivatives, dibenzofuran derivatives, ladder-type furan compounds, pyrimidine derivatives, and the like, but are not limited thereto.

Examples of the dopant material include an aromatic amine derivative, a styrylamine compound, a boron complex, a fluoranthene compound, a metal complex, and the like. Specific examples of the aromatic amine derivatives include substituted or unsubstituted fused aromatic ring derivatives having an arylamino group, examples thereof include pyrene, anthracene, chrysene, and periflanthene having the arylamino group, and the like, the styrylamine compound is a compound where at least one arylvinyl group is substituted in substituted or unsubstituted arylamine, in which one or more substituent groups selected from the group consisting of an aryl group, a silyl group, an alkyl group, a cycloalkyl group, and an arylamino group are substituted or unsubstituted. Specific examples thereof include styrylamine, styryldiamine, styryltriamine, styryltetramine, and the like, but are not limited thereto. Further, examples of the metal complex include an iridium complex, a platinum complex, and the like, but are not limited thereto.

The electron transport layer is a layer receiving the electrons from the electron injection layer and transporting the electrons to the light emitting layer, the electron transport material is a material that can receive the electrons well from the cathode and transport the electrons to the light emitting layer, and a material having large mobility to the electrons is suitable. Specific examples thereof include an 8-hydroxyquinoline Al complex; a complex including $Alq_3$; an organic radical compound; a hydroxyflavone-metal complex, and the like, but are not limited thereto. The electron transport layer may be used together with a predetermined desired cathode material as used according to the prior art. Particularly, an example of an appropriate cathode material is a general material having the low work function and followed by an aluminum layer or a silver layer. Specific examples thereof include cesium, barium, calcium, ytterbium, and samarium, and each case is followed by the aluminum layer or the silver layer.

The electron injection layer is a layer injecting the electrons from the electrode, and a compound which has an ability of transporting the electrons, an electron injecting effect from the cathode, and an excellent electron injecting effect to the light emitting layer or the light emitting material, prevents movement of an exciton generated in the light emitting layer to the hole injection layer, and has an excellent thin film forming ability is preferable. Specific examples thereof include fluorenone, anthraquinodimethane, diphenoquinone, thiopyran dioxide, oxazole, oxadiazole, triazole, imidazole, perylene tetracarboxylic acid, fluorenylidene methane, anthrone, and the like, and its derivative, a metal complex compound, a nitrogen-containing 5-membered cycle derivative, and the like, but are not limited thereto.

Examples of the metal complex compound include 8-hydroxyquinolinato lithium, bis(8-hydroxyquinolinato)zinc, bis(8-hydroxyquinolinato)copper, bis(8-hydroxyquinolinato)manganese, tris(8-hydroxyquinolinato)aluminum, tris(2-methyl-8-hydroxyquinolinato)aluminum, tris(8-hydroxyquinolinato)gallium, bis(10-hydroxybenzo[h]quinolinato) beryllium, bis(10-hydroxybenzo[h]quinolinato)zinc, bis(2-methyl-8-quinolinato)chlorogallium, bis(2-methyl-8-quinolinato)(o-cresolato)gallium, bis(2-methyl-8-quinolinato)(1-naphtholato)aluminum, bis(2-methyl-8-quinolinato)(2-naphtholato)gallium, and the like, but are not limited thereto.

The organic light emitting device according to the present disclosure may be a front side emission type, a back side emission type, or a double side emission type according to the used material.

In addition, the compound represented by the Chemical Formula 1 may be included in an organic solar cell or an organic transistor in addition to an organic light emitting device.

The preparation of the compound represented by the Chemical Formula 1 and the organic light emitting device comprising the same will be described in detail in the following examples. However, these examples are presented for illustrative purposes only, and the scope of the present disclosure is not limited thereto.

Example 1 (E1)

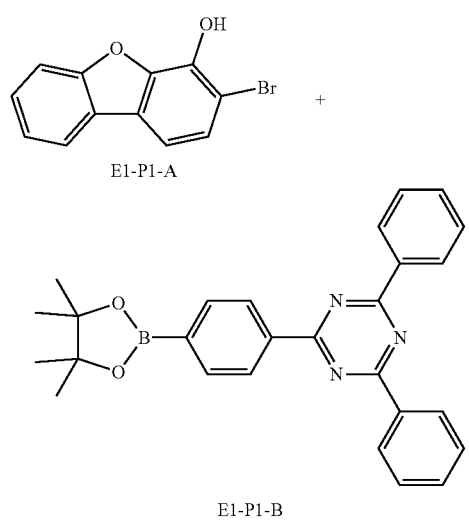

E1-P1-A

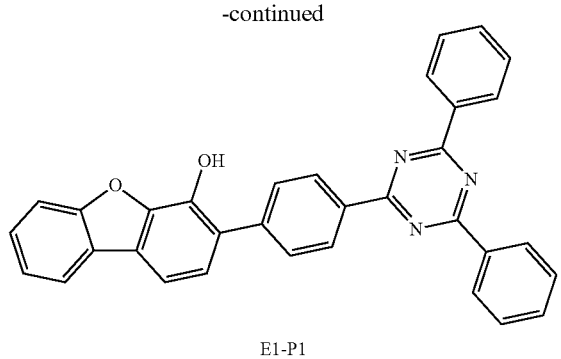

E1-P1

A compound (10.0 g, 38.0 mmol) represented by Chemical Formula E1-P1-A above and a compound (16.5 g, 38.0 mmol) represented by Chemical Formula E1-P1-B above were completely dissolved in THF (100 mL), and then a solution in which potassium carbonate (15.8 g, 114.0 mmol) was dissolved in 60 mL of water was added thereto. Tetrakis(triphenylphosphine)palladium (1.3 g, 1.14 mmol) was added and the mixture was heated and stirred for 8 hours. After the temperature was lowered to room temperature and the reaction was terminated, the potassium carbonate solution was removed and the white solid was filtered. The filtered white solid was washed twice with THF and ethyl acetate, respectively, to produce a compound (16.6 g, yield 89%) represented by Chemical Formula E1-P1 above.

MS [M+H]$^+$=492

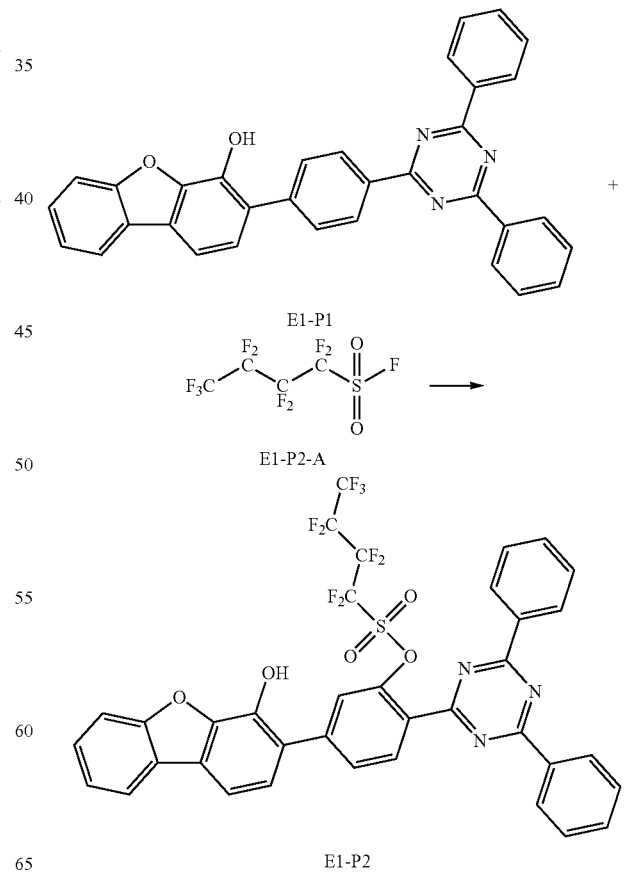

E1-P2

A compound (16.5 g, 33.6 mmol) represented by Chemical Formula E1-P1 above was completely dissolved in acetonitrile (160 mL), and then a solution in which potassium carbonate (13.9 g, 100.9 mmol) was dissolved in 55 mL of water was added thereto. A compound (10.2 g, 33.6 mmol) represented by Chemical Formula E1-P2-A above was added dropwise to the reaction solution. After termination of the reaction, the potassium carbonate solution was removed and the white solid was filtered. The filtered white solid was washed twice with ethanol and water, respectively, to produce a compound (23.9 g, yield 92%) represented by Chemical Formula E1-P2 above.

MS $[M+H]^+$=774

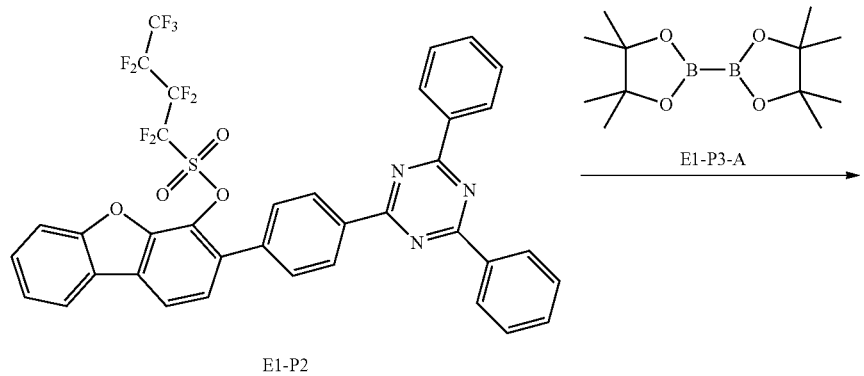

E1-P2

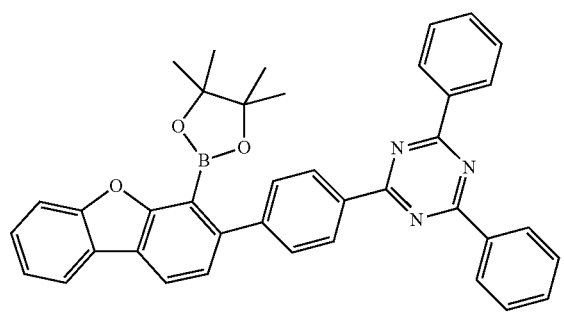

E1-P3

A compound (22.7 g, 29.3 mmol) represented by Chemical Formula E1-P2 above and a compound (7.5 g, 29.3 mmol) represented by Chemical Formula E1-P3-A above were completely dissolved in dioxane (300 mL), and then potassium acetate (8.6 g, 87.8 mmol) was added thereto, and heated and stirred. After the temperature was lowered to room temperature and the reaction was terminated, the potassium carbonate solution was removed and filtered to remove potassium acetate. The filtrate was solidified with ethanol and filtered. The white solid was washed twice with ethanol, respectively, to produce a compound (15.4 g, yield 87%) represented by the above formula E1-P3.

MS [M+H]$^+$=602

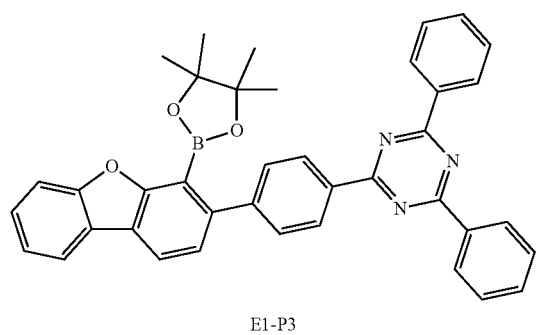

E1-P3

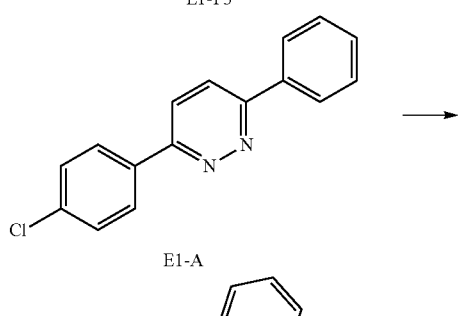

E1-A

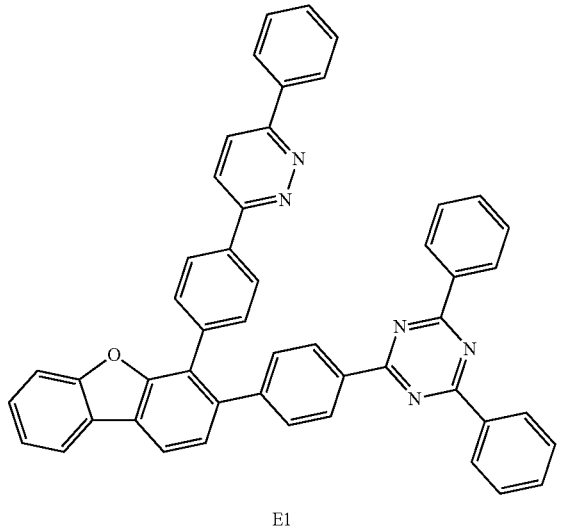

E1

A compound (14.1 g, 23.5 mmol) represented by Chemical Formula E1-P3 above and a compound (6.3 g, 23.5 mmol) represented by Chemical Formula E1-A above were completely dissolved in THF (150 mL), and then a solution in which potassium carbonate (9.7 g, 70.4 mmol) was dissolved in 40 mL of water was added thereto. Tetrakis(triphenylphosphine)palladium (0.8 g, 0.704 mmol) was added thereto, and heated and stirred for 8 hours. After the temperature was lowered to room temperature and the reaction was terminated, the potassium carbonate solution was removed and the white solid was filtered. The filtered white solid was washed twice with THF and ethyl acetate, respectively, to produce a compound (12.1 g, yield 73%) represented by Chemical Formula E1 above.

MS [M+H]$^+$=706

Example 2 (E2)

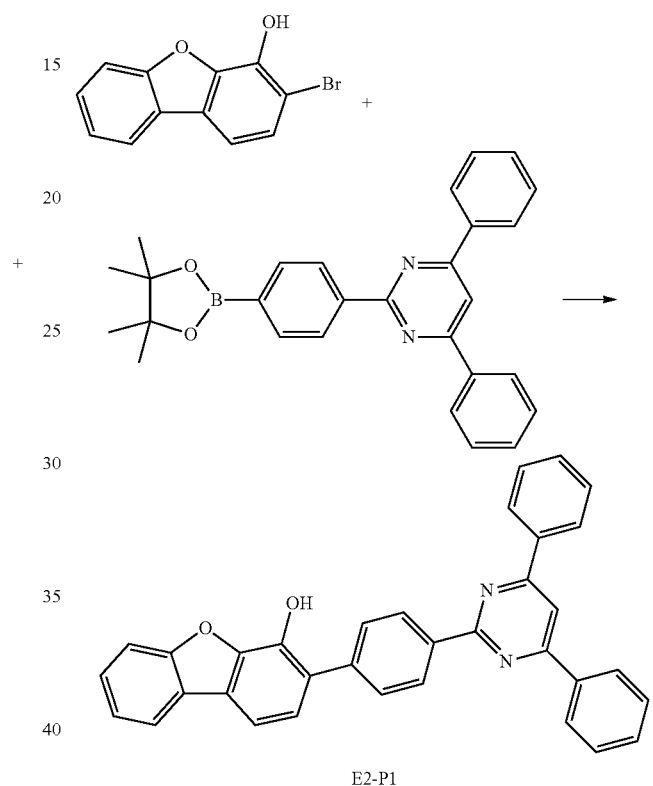

E2-P1

A compound represented by Chemical Formula E2-P1 above was prepared in the same manner as in E1-P1 of Example 1, except that the respective starting materials were reacted as shown in the reaction scheme above.

MS [M+H]$^+$=491

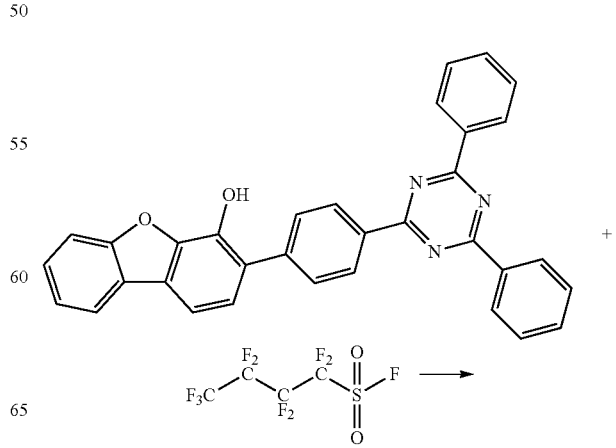

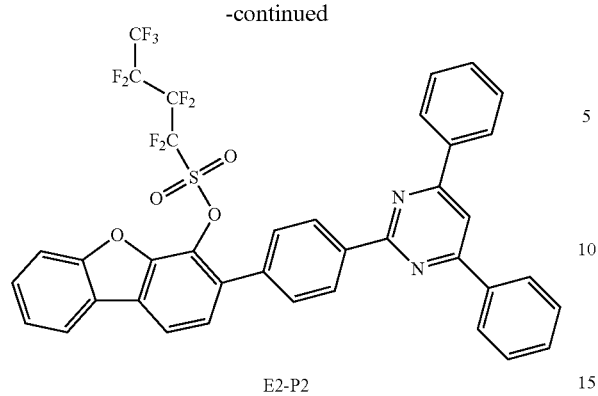
E2-P2
A compound represented by Chemical Formula E2-P2 above was prepared in the same manner as in E1-P2 of Example 1, except that the respective starting materials were reacted as shown in the reaction scheme above.
MS [M+H]$^+$=773
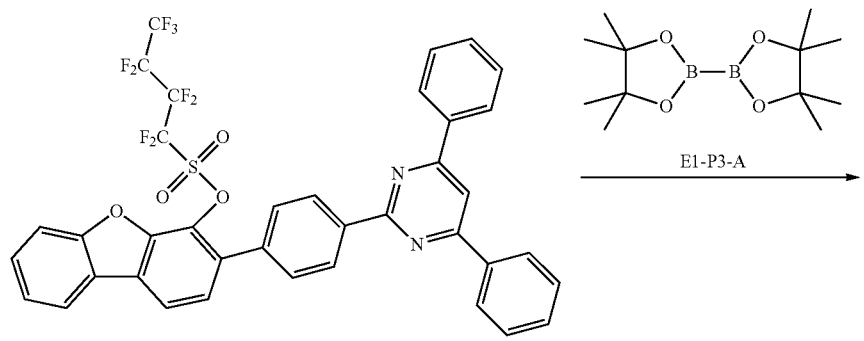
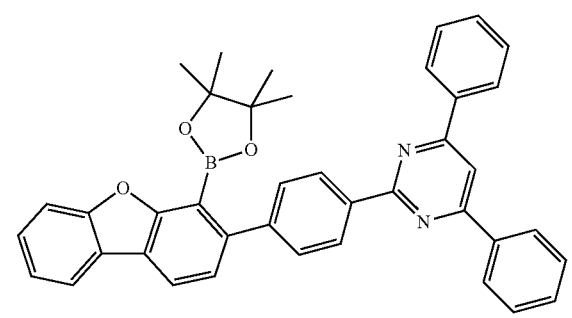
E2-P3

A compound represented by Chemical Formula E2-P3 above was prepared in the same manner as in E1-P3 of Example 1, except that the respective starting materials were reacted as shown in the reaction scheme above.

MS [M+H]⁺=601

MS [M+H]⁺=782

Example 3 (E3)

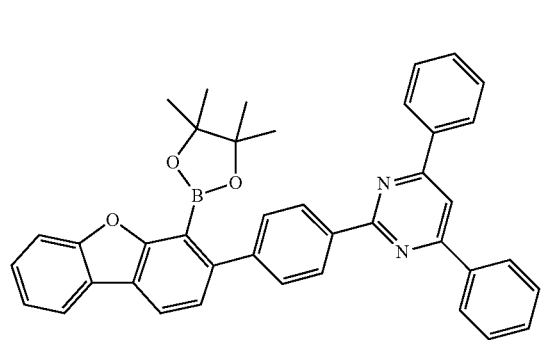

+

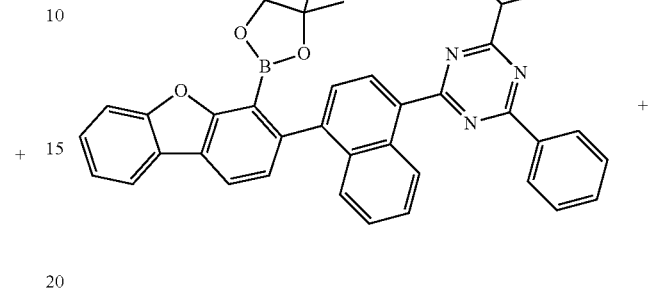

+

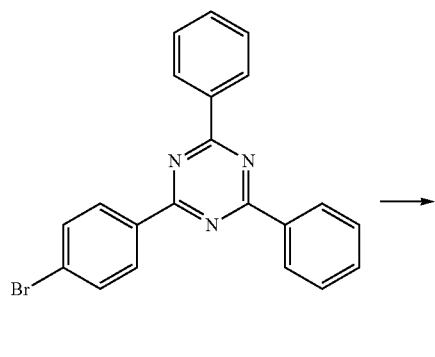

→

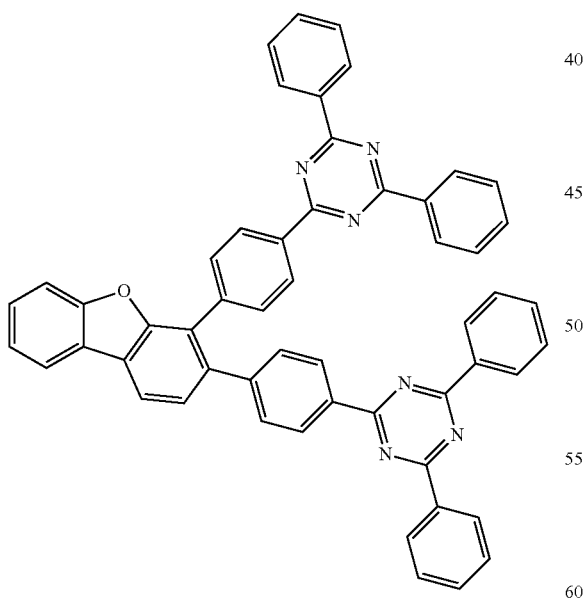

E2

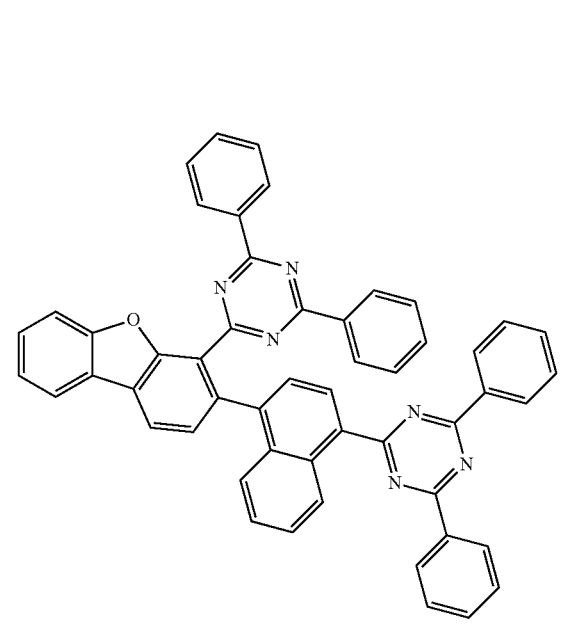

E3

A compound represented by Chemical Formula E2 above was prepared in the same manner as in E1 of Example 1, except that the respective starting materials were reacted as shown in the reaction scheme above, A compound represented by Chemical Formula E3 above was prepared in the same manner as in E1 of Example 1, except that the respective starting materials were reacted as shown in the reaction scheme above.

MS [M+H]⁺=757
Example 4 (E4)
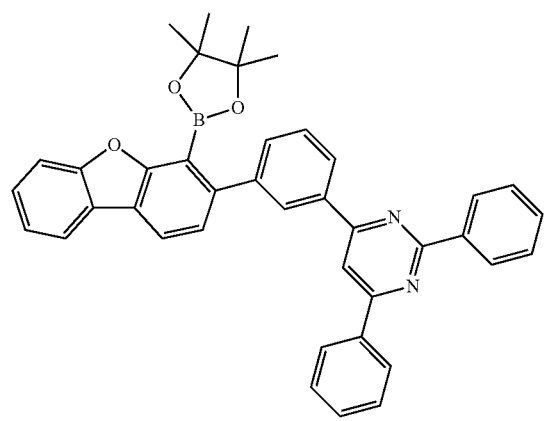
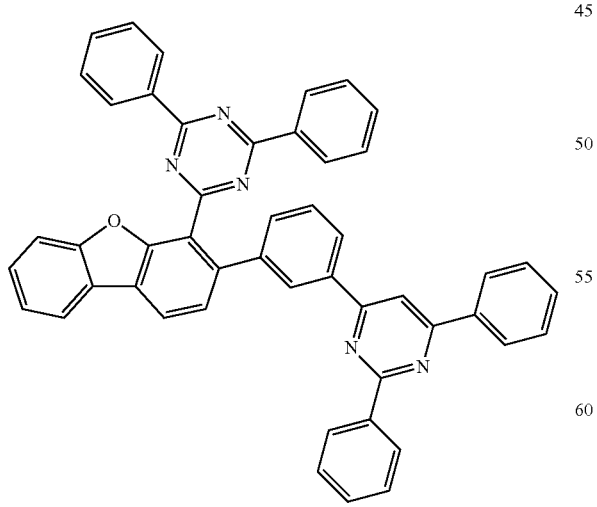
E4
A compound represented by Chemical Formula E4 above was prepared in the same manner as in E1 of Example 1, except that the respective starting materials were reacted as shown in the reaction scheme above.
MS [M+H]⁺=706
Example 5 (E5)
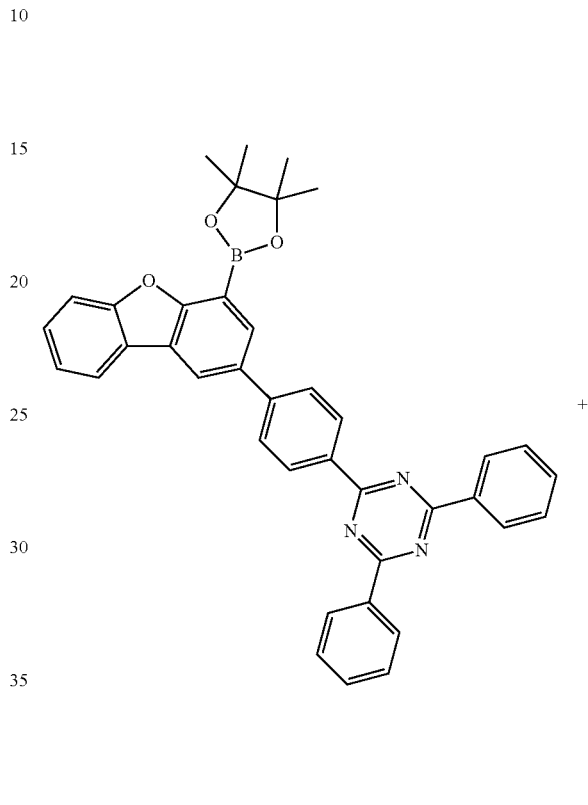
+
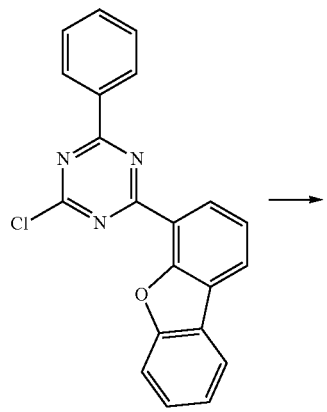

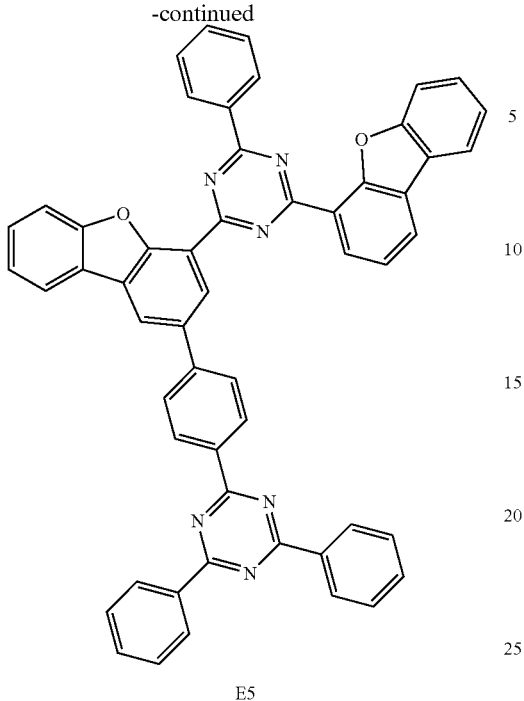

E5

A compound represented by Chemical Formula E5 above was prepared in the same manner as in E1 of Example 1, except that the respective starting materials were reacted as shown in the reaction scheme above.

MS [M+H]$^+$=797

Example 6 (E6)

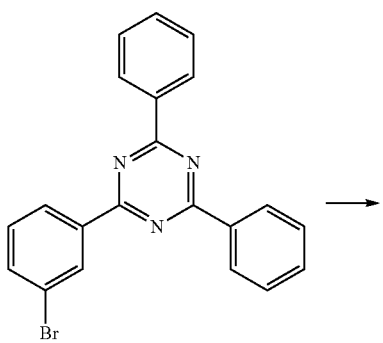

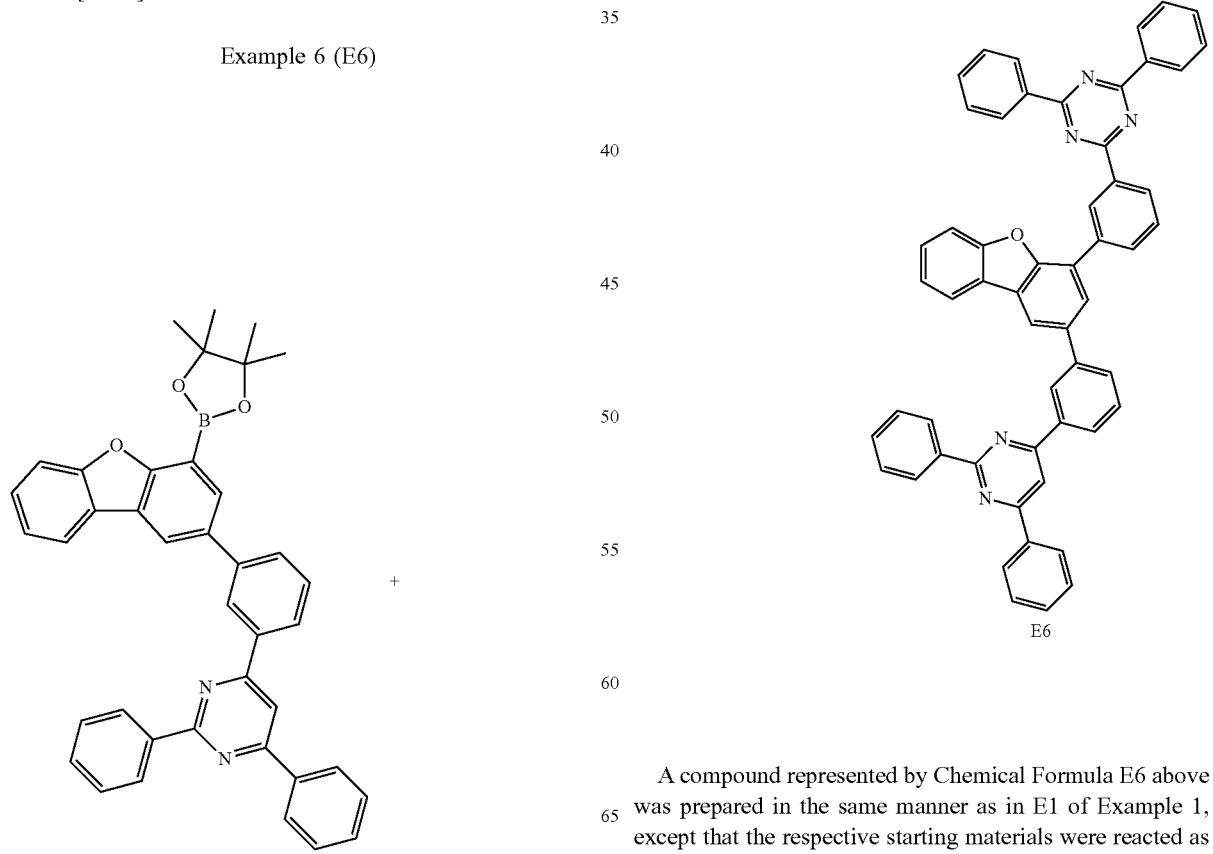

E6

A compound represented by Chemical Formula E6 above was prepared in the same manner as in E1 of Example 1, except that the respective starting materials were reacted as shown in the reaction scheme above.

MS [M+H]⁺=782

Example 7 (E7)

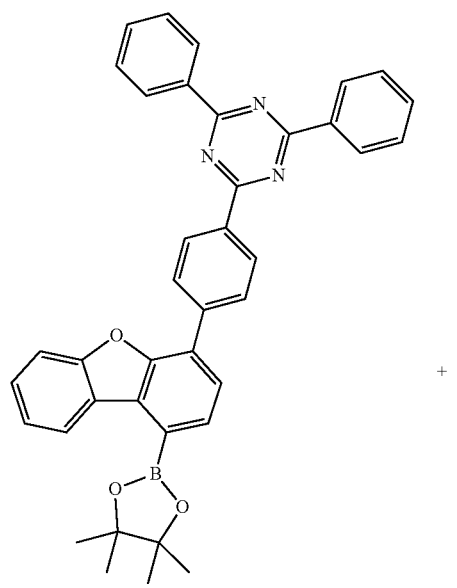

E7

A compound represented by Chemical Formula E7 above was prepared in the same manner as in E1 of Example 1, except that the respective starting materials were reacted as shown in the reaction scheme above.

MS [M+H]⁺=883

Example 8 (E8)

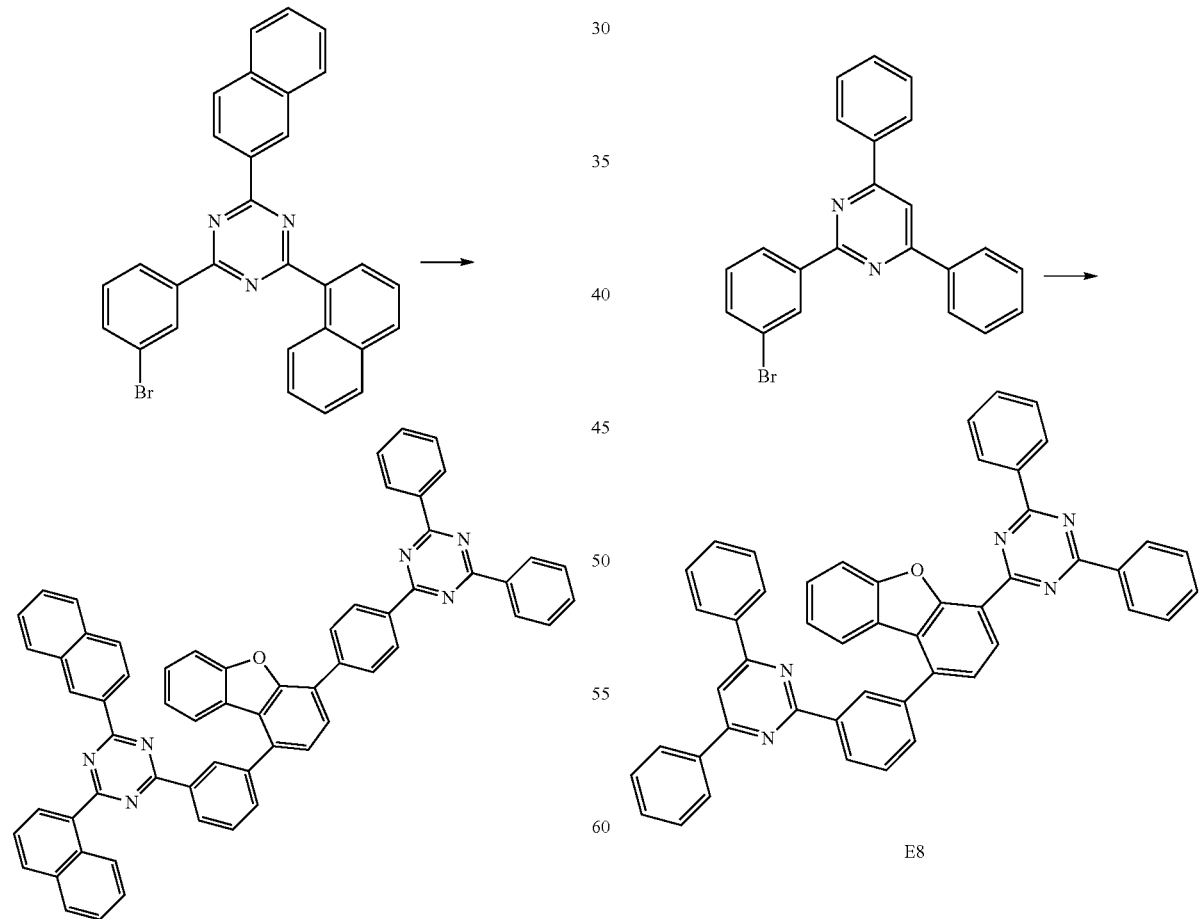

E8

A compound represented by Chemical Formula E8 above was prepared in the same manner as in E1 of Example 1, except that the respective starting materials were reacted as shown in the reaction scheme above.

MS [M+H]⁺=883
Example 9 (E9)
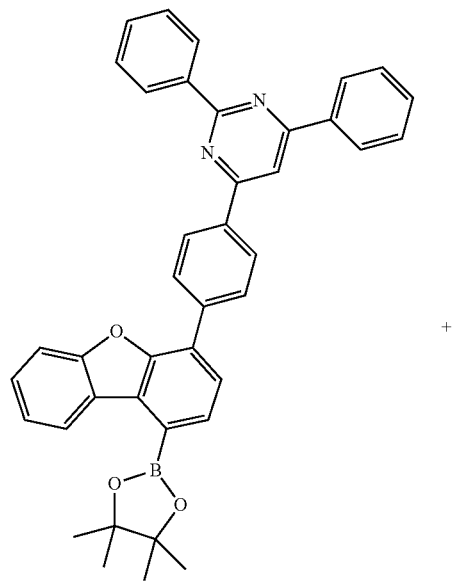
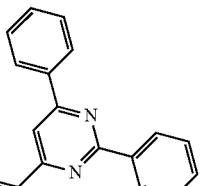
E9
A compound represented by Chemical Formula E9 above was prepared in the same manner as in E1 of Example 1, except that the respective starting materials were reacted as shown in the reaction scheme above.
MS [M+H]⁺=857
Example 10 (E10)
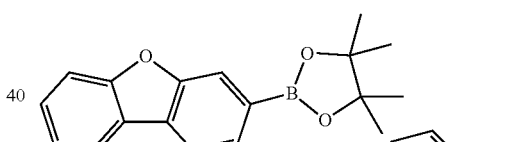
+
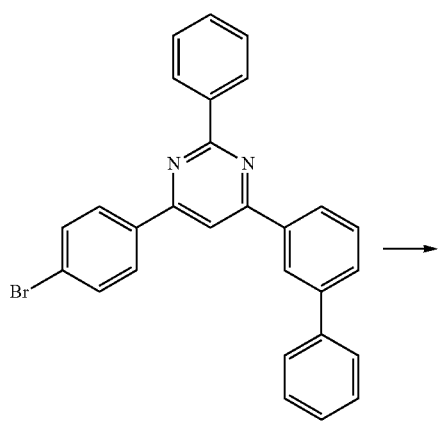
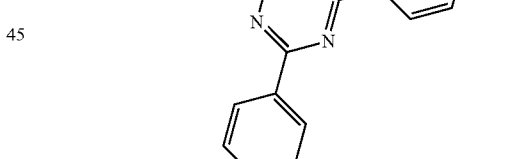
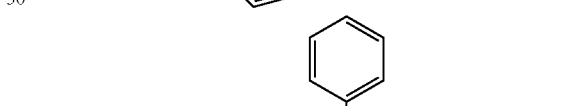
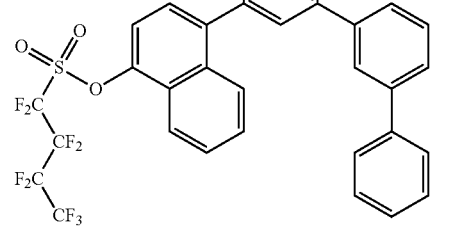

-continued

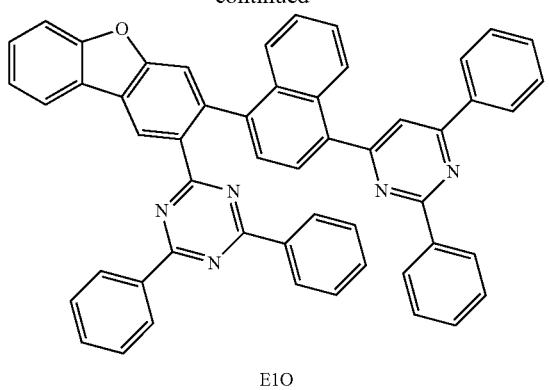

E10

A compound represented by Chemical Formula E10 above was prepared in the same manner as in E1 of Example 1, except that the respective starting materials were reacted as shown in the reaction scheme above.

MS [M+H]$^+$=756

Example 11 (E11)

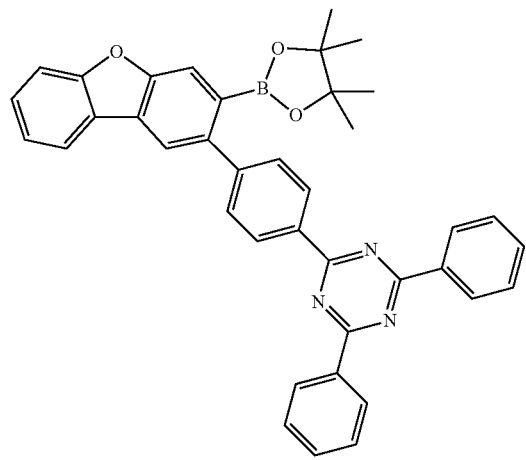

+

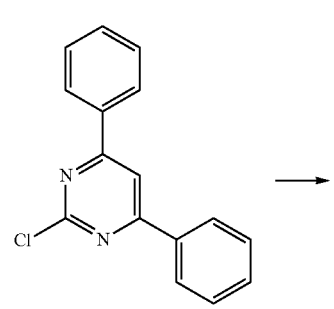

-continued

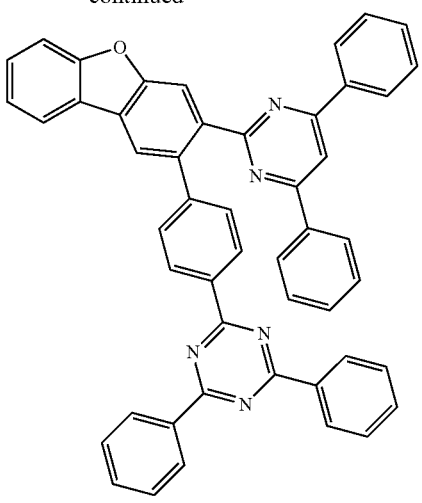

E11

A compound represented by Chemical Formula E11 above was prepared in the same manner as in E1 of Example 1, except that the respective starting materials were reacted as shown in the reaction scheme above.

MS [M+H]$^+$=706

Example 12 (E12)

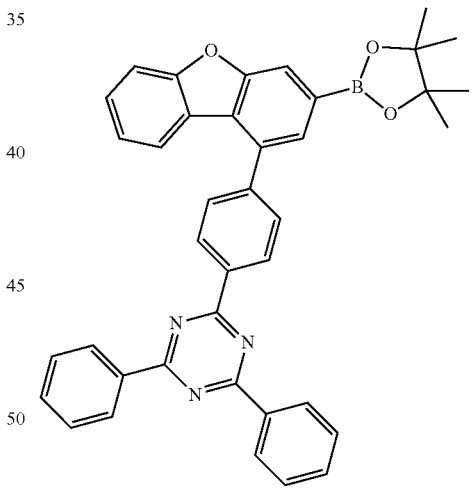

+

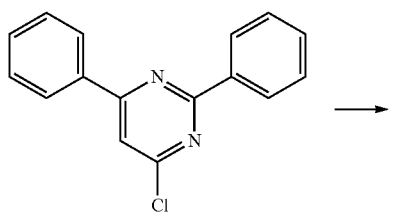

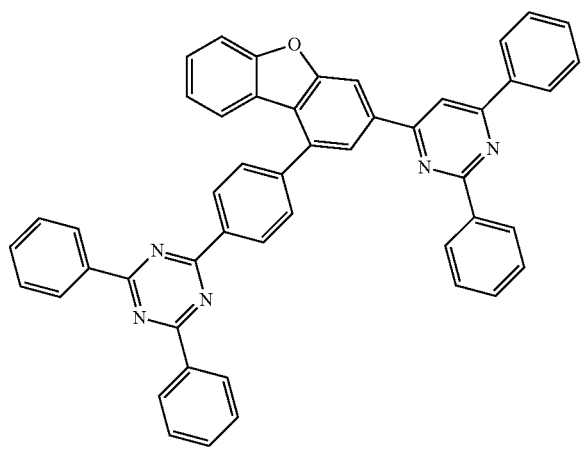

E12

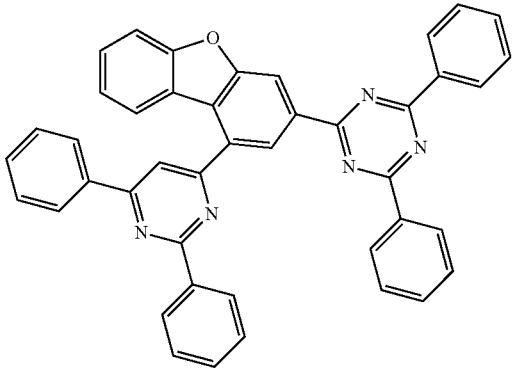

E13

A compound represented by Chemical Formula E12 above was prepared in the same manner as in E12 of Example 1, except that the respective starting materials were reacted as shown in the reaction scheme above.

MS [M+H]$^+$=706

Example 13 (E13)

A compound represented by Chemical Formula E13 above was prepared in the same manner as in E1 of Example 1, except that the respective starting materials were reacted as shown in the reaction scheme above.

MS [M+H]$^+$=630

Example 14 (E14)

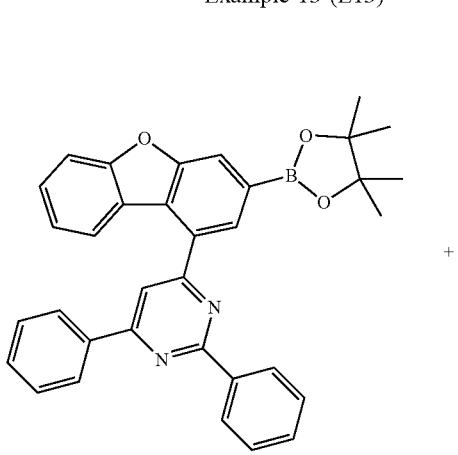

+

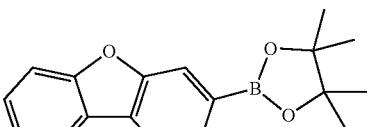

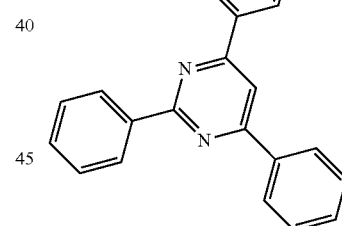

+

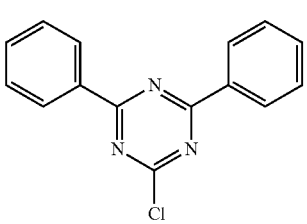

→

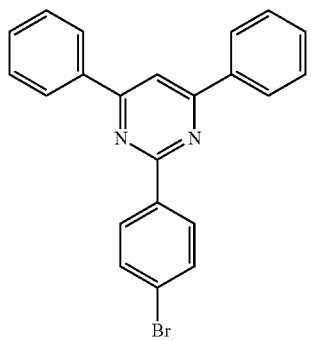

→

-continued

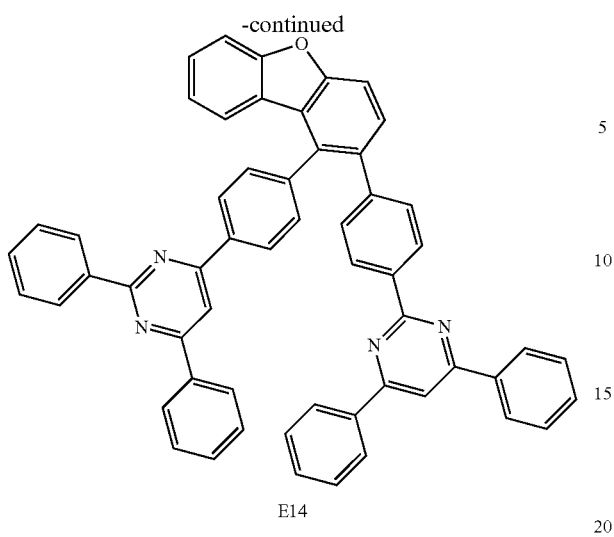

E14

A compound represented by Chemical Formula E14 above was prepared in the same manner as in E1 of Example 1, except that the respective starting materials were reacted as shown in the reaction scheme above.

MS [M+H]$^+$=781

Example 15 (E15)

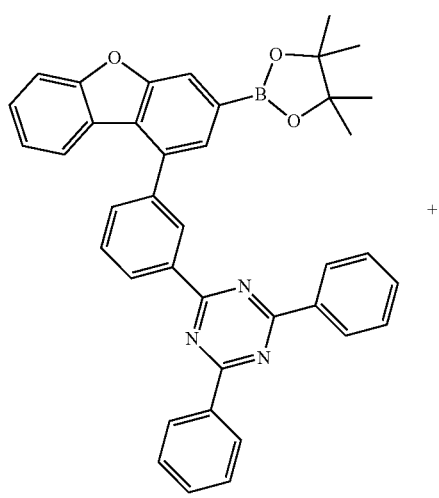

+

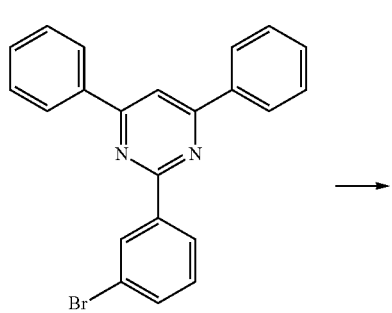

→

-continued

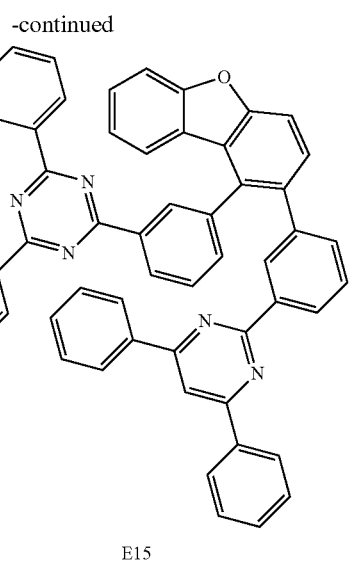

E15

A compound represented by Chemical Formula E15 above was prepared in the same manner as in E1 of Example 1, except that the respective starting materials were reacted as shown in the reaction scheme above.

MS [M+H]$^+$=782

Example 16 (E16)

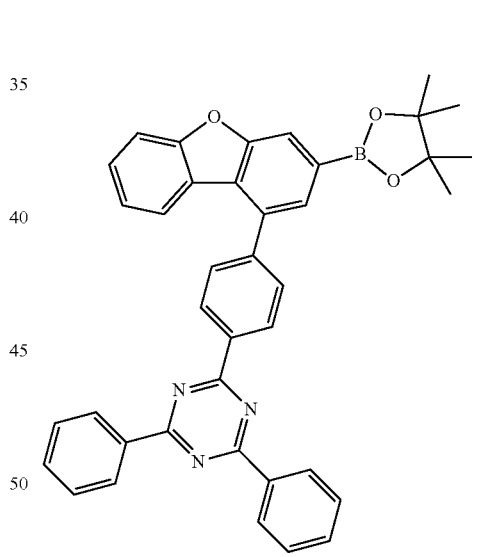

+

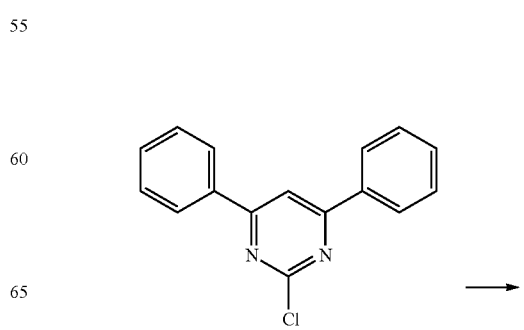

→

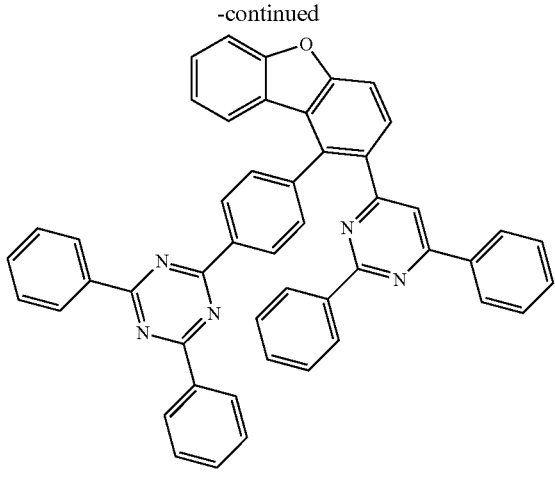

E16

A compound represented by Chemical Formula E16 above was prepared in the same manner as in E1 of Example 1, except that the respective starting materials were reacted as shown in the reaction scheme above.

MS [M+H]$^+$=706

Example 17 (E17)

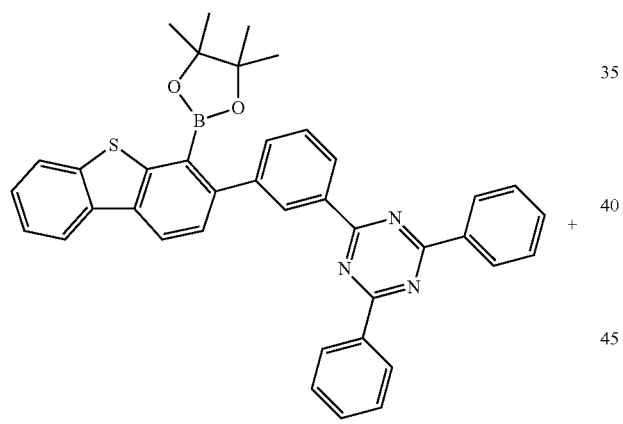

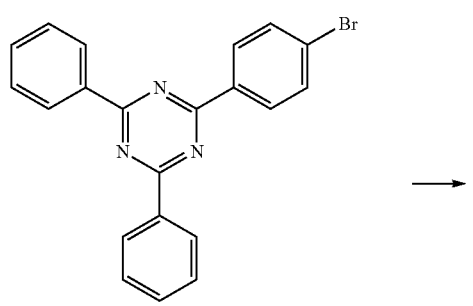

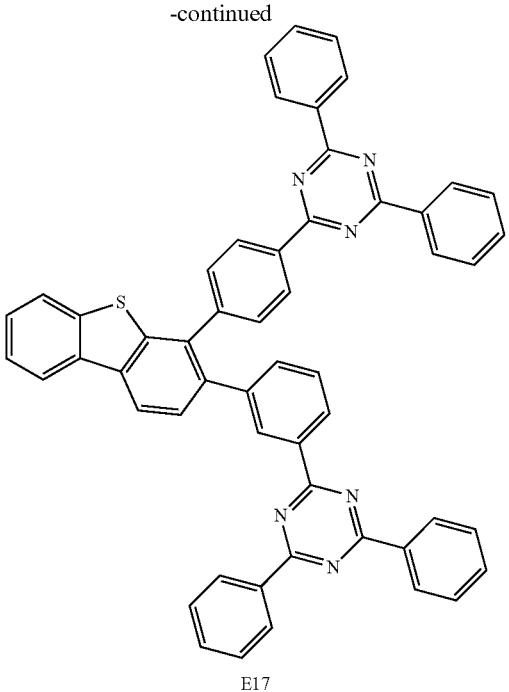

E17

A compound represented by Chemical Formula E17 above was prepared in the same manner as in E1 of Example 1, except that the respective starting materials were reacted as shown in the reaction scheme above.

MS [M+H]$^+$=799

Example 18 (E18)

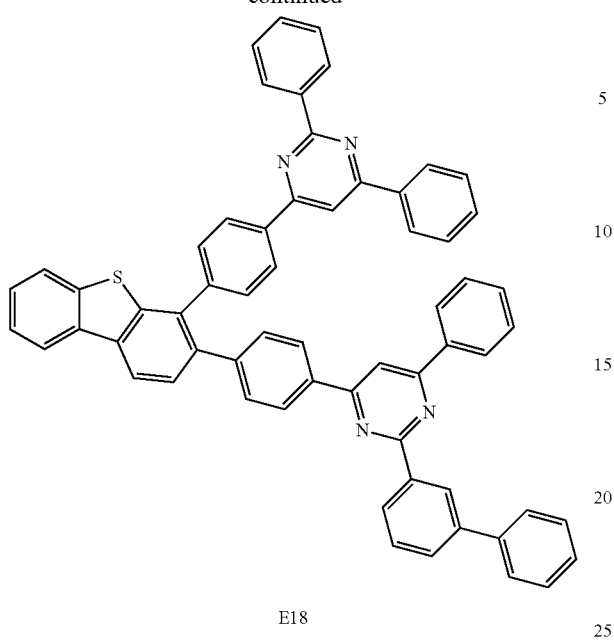

E18

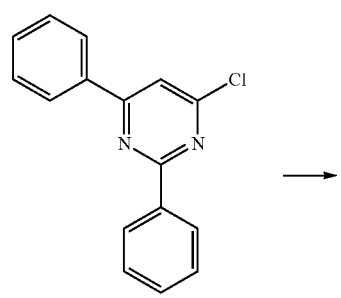

A compound represented by Chemical Formula E18 above was prepared in the same manner as in E1 of Example 1, except that the respective starting materials were reacted as shown in the reaction scheme above.

MS [M+H]$^+$=873

Example 19 (E19)

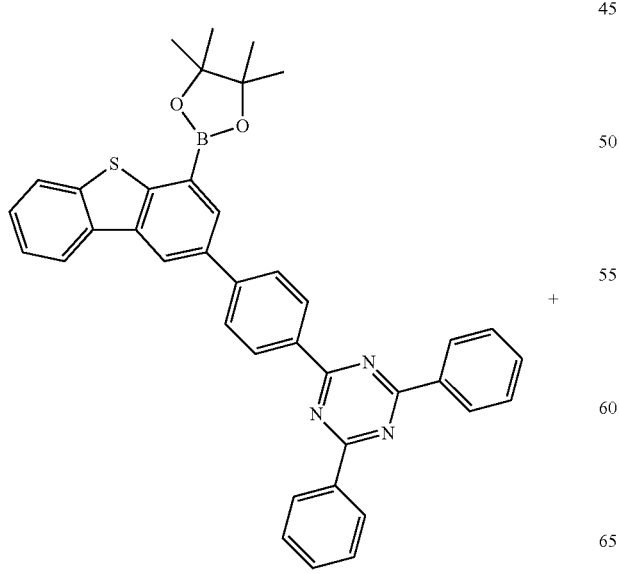

+

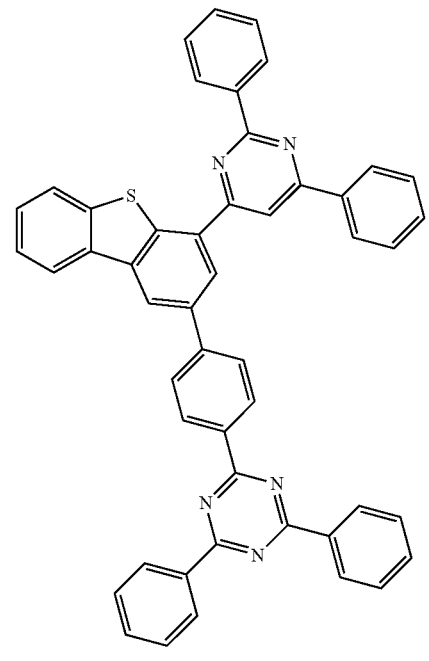

E19

A compound represented by Chemical Formula E19 above was prepared in the same manner as in E1 of Example 1, except that the respective starting materials were reacted as shown in the reaction scheme above.

MS [M+H]$^+$=722
Example 20 (E20)
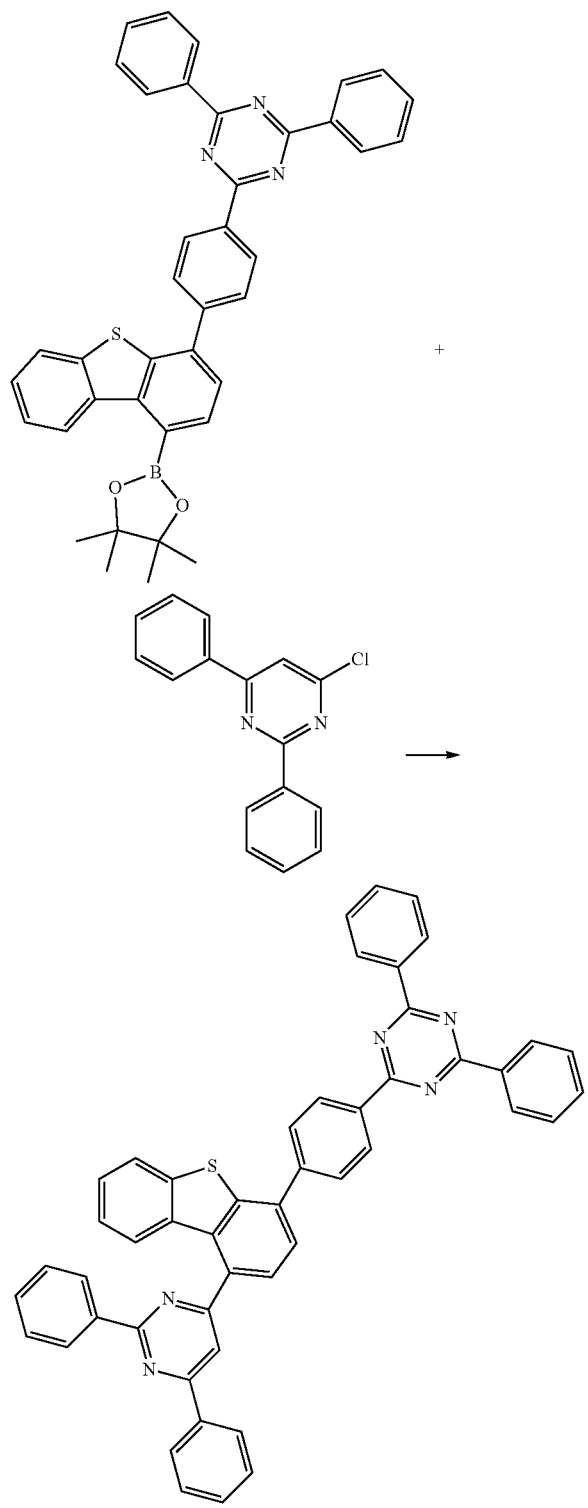
E20
A compound represented by Chemical Formula E20 above was prepared in the same manner as in E1 of Example 1, except that the respective starting materials were reacted as shown in the reaction scheme above.
MS [M+H]$^+$=722
Example 21 (E21)
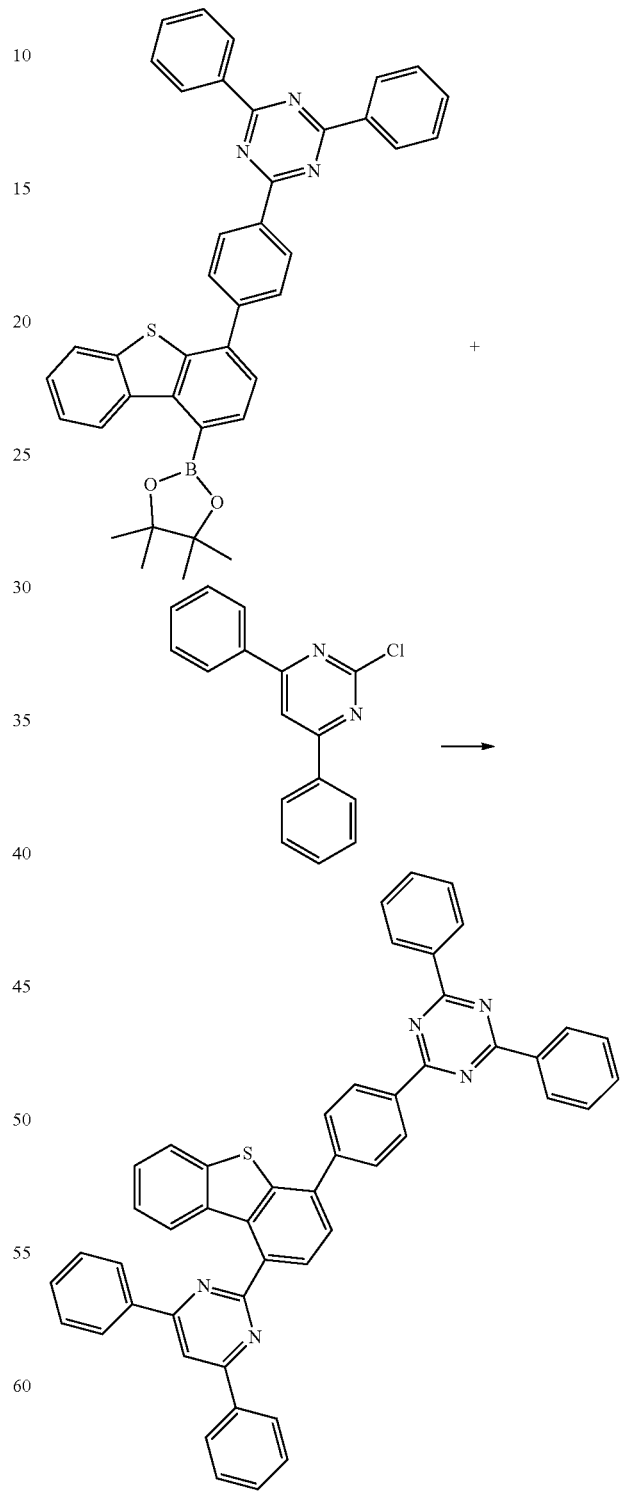
E21

A compound represented by Chemical Formula E21 above was prepared in the same manner as in E1 of Example 1, except that the respective starting materials were reacted as shown in the reaction scheme above.

MS [M+H]$^+$=722

Example 22 (E22)

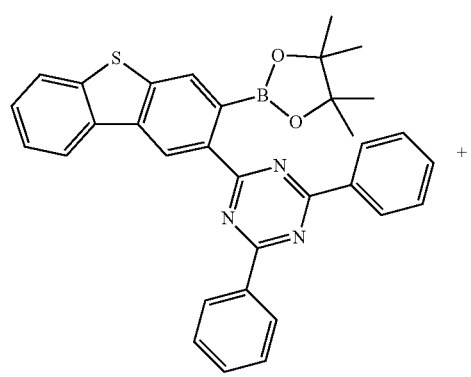

+

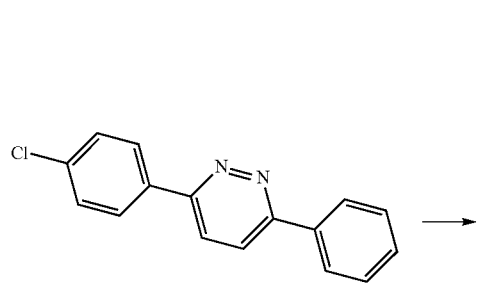

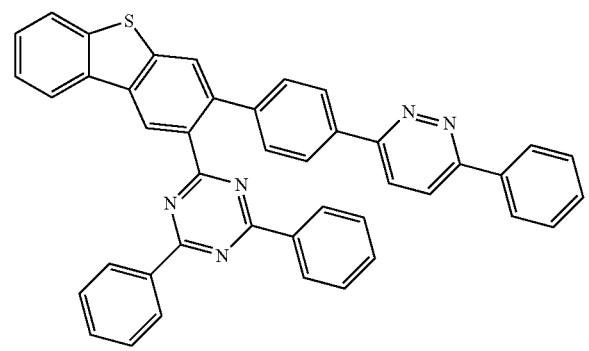

E22

A compound represented by Chemical Formula E22 above was prepared in the same manner as in E1 of Example 1, except that the respective starting materials were reacted as shown in the reaction scheme above.

MS [M+H]$^+$=646

Example 23 (E23)

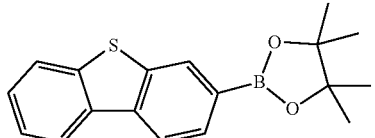

+

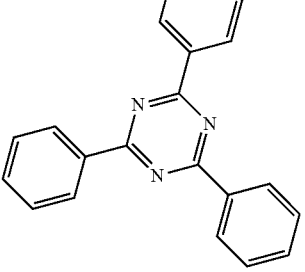

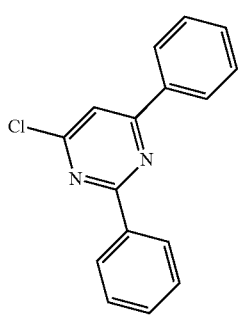

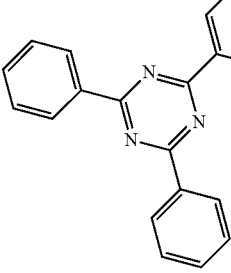

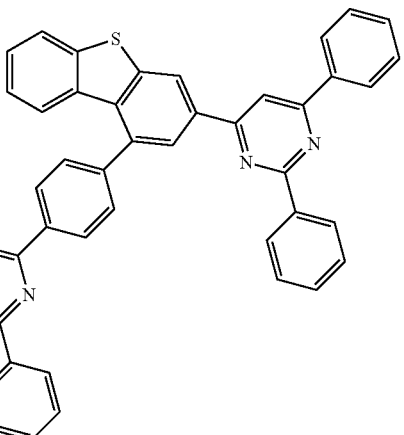

E23

A compound represented by Chemical Formula E23 above was prepared in the same manner as in E1 of Example 1, except that the respective starting materials were reacted as shown in the reaction scheme above.

MS [M+H]$^+$=722

Example 24 (E24)

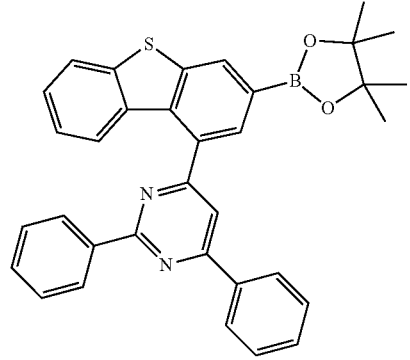

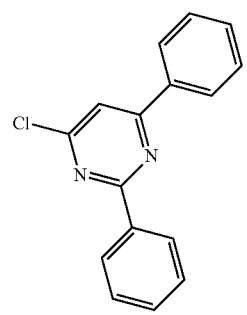

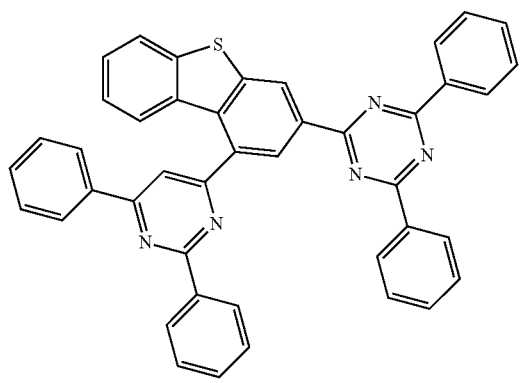

E24

A compound represented by Chemical Formula E24 above was prepared in the same manner as in E1 of Example 1, except that the respective starting materials were reacted as shown in the reaction scheme above.

MS [M+H]$^+$=646

Example 25 (E25)

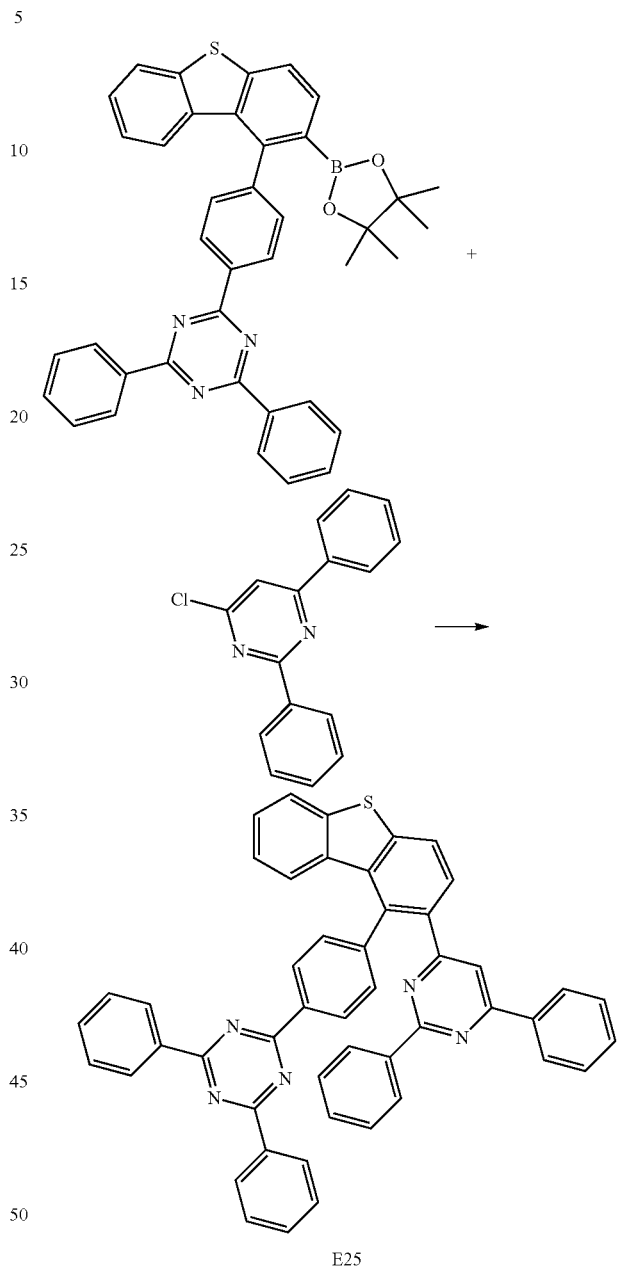

E25

A compound represented by Chemical Formula E25 above was prepared in the same manner as in E1 of Example 1, except that the respective starting materials were reacted as shown in the reaction scheme above.

MS [M+H]$^+$=722

Experimental Example 1-1

A glass substrate on which a thin film of ITO (indium tin oxide) was coated in a thickness of 1,000 Å was put into distilled water containing the detergent dissolved therein and washed by the ultrasonic wave. In this case, the used detergent was a product commercially available from Fisher Co. and the distilled water was one which had been twice filtered by using a filter commercially available from Millipore Co. The ITO was washed for 30 minutes, and ultrasonic washing was then repeated twice for 10 minutes by using distilled water. After the washing with distilled water was completed, the substrate was ultrasonically washed with isopropyl alcohol, acetone, and methanol solvent, and dried, after which it was transported to a plasma cleaner. Then, the substrate was cleaned with oxygen plasma for 5 minutes, and then transferred to a vacuum evaporator.

On the ITO transparent electrode thus prepared, a compound of Formula [HI-A] below was thermally vacuum-deposited in a thickness of 600 Å to form a hole injection layer. Hexaazatriphenylene of Formula [HAT] below (50 Å) and a compound of Formula [HT-A] below (600 Å) were sequentially vacuum-deposited on the hole injection layer to form a hole transport layer. Then, compounds of Formulas [BH] and [BD] below were vacuum-deposited at a weight ratio of 25:1 on the hole transport layer in a thickness of 200 Å to form a light emitting layer. The compound of the Formula E1 and lithiumquinolate of Formula [LiQ] were vacuum-deposited at a weight ratio of 1:1 on the light emitting layer to form an electron injection and transport layer with a thickness of 350 Å. Lithium fluoride (LiF) in a thickness of 10 Å and aluminum (LiF) in a thickness of 1,000 Å were sequentially deposited on the electron injection and transport layer to form a cathode.

In the above process, the vapor deposition rate of the organic material was maintained at 0.4 to 0.9 Å/sec, the vapor deposition rate of lithium fluoride of the cathode was maintained at 0.3 Å/sec, the vapor deposition rate of aluminum was maintained at 2 Å/sec, and the degree of vacuum during vapor deposition was maintained at $1\times10^{-7}$~$5\times10^{-8}$ torr to manufacture an organic light emitting device.

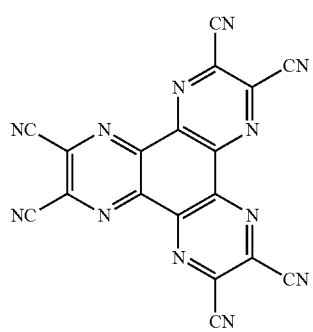

[HAT]

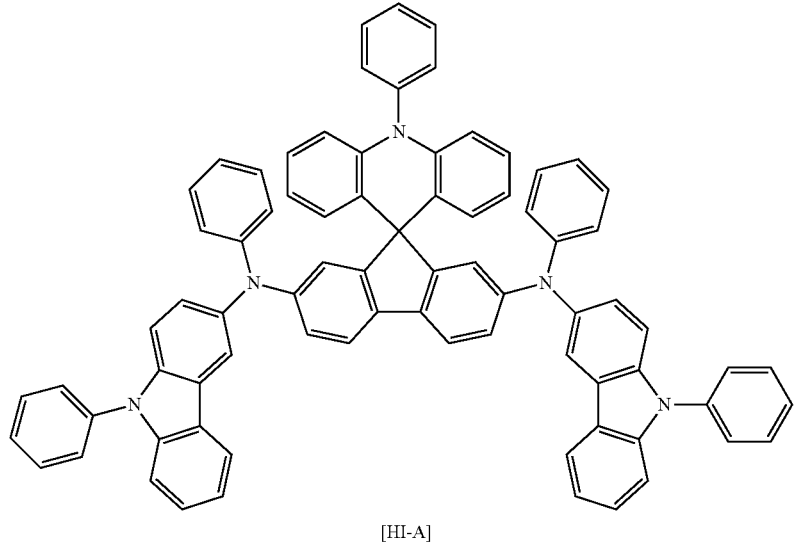

[HI-A]

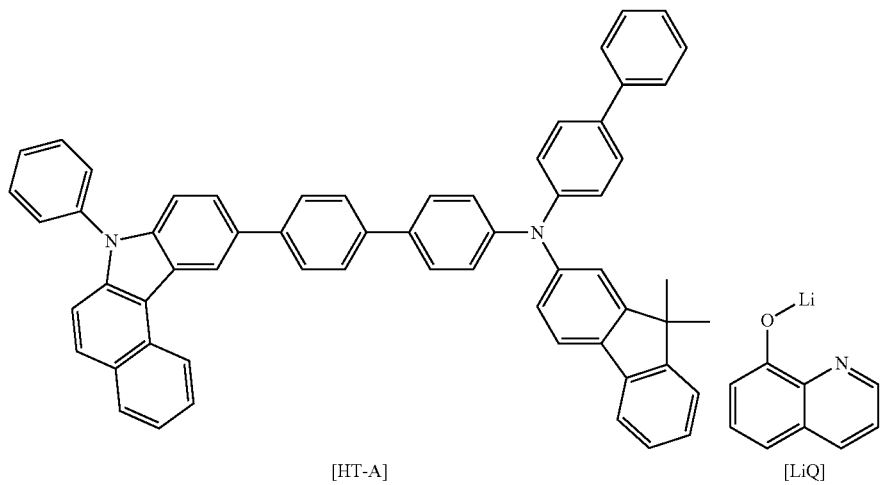

[HT-A]

[LiQ]

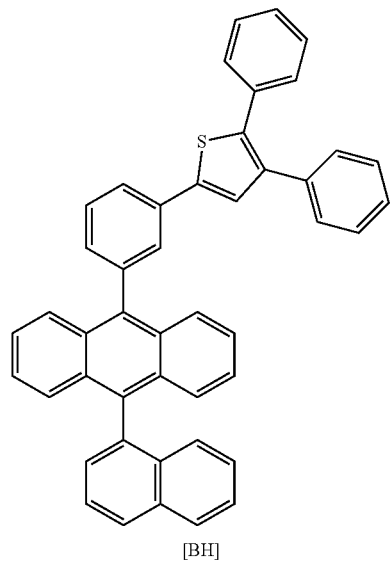

[BH]

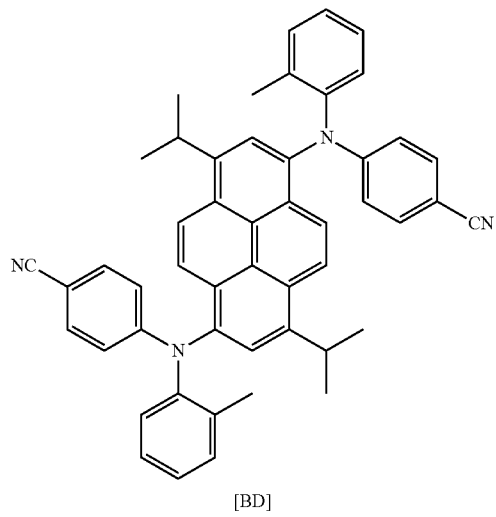

[BD]

Experimental Examples 1-2 to 1-25

The organic light emitting device was manufactured in the same manner as in Experimental Example 1-1, except that the compounds shown in Table 1 below was used instead of the compound E1 of Example 1 in Experimental Example 1-1.

Comparative Experimental Examples 1-1 to 1-15

The organic light emitting devices were manufactured in the same manner as in Experimental Example 1-1, except that the compounds shown in Table 2 below were used instead of the compound 1 of Example 1 in Experimental Example 1. In Table 2, the structure of each compound is as follows.

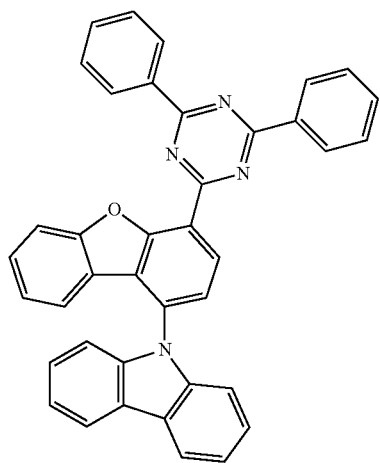

[ET-1-A]

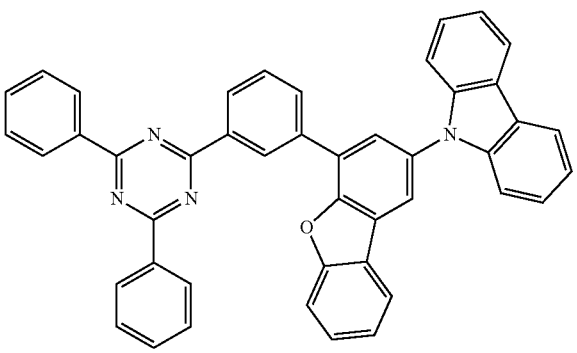

[ET-1-B]

-continued
[ET-1-C]
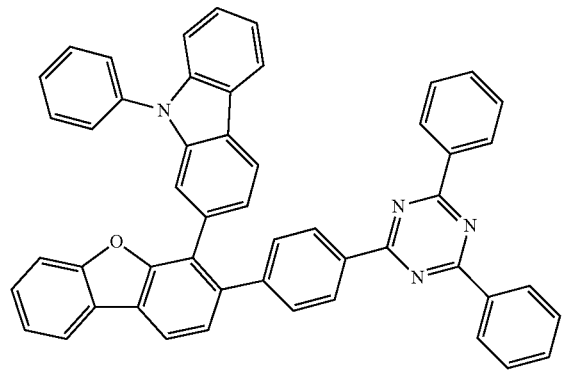
[ET-1-D]
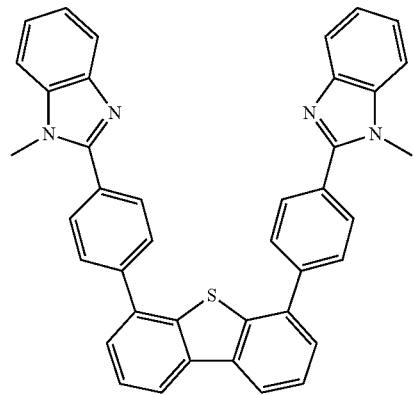
[ET-1-E]
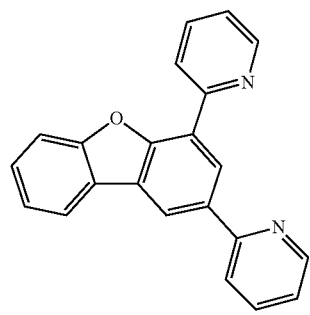
[ET-1-F]
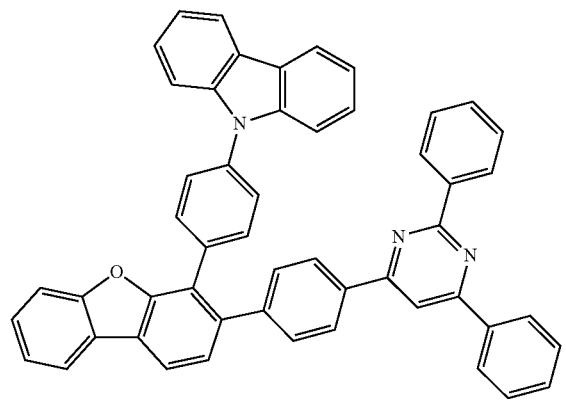
[ET-1-G]
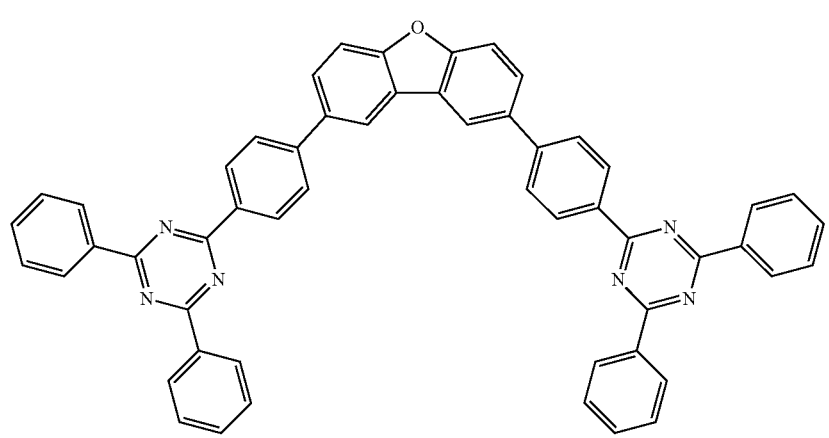

[ET-1-H]
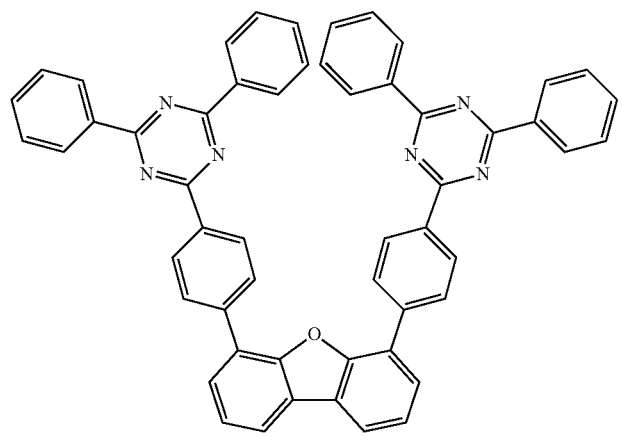
[ET-1-I]
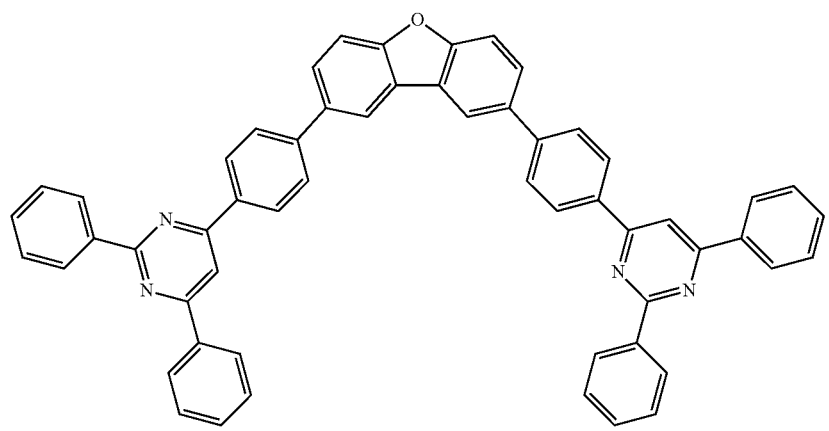
[ET-1-J]
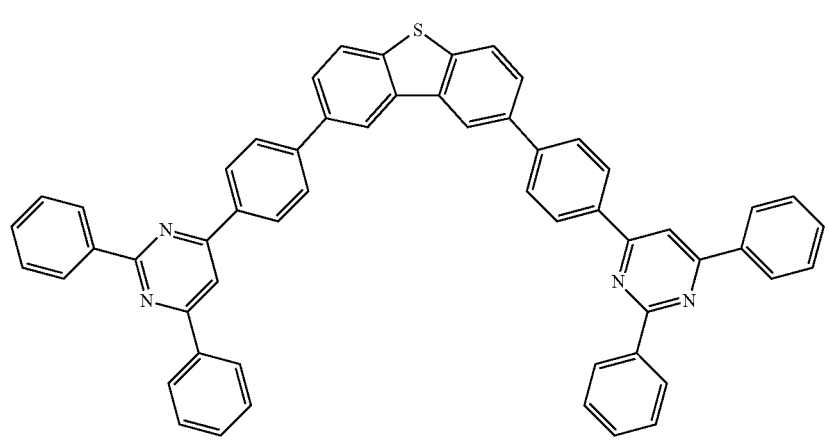

[ET-1-K]
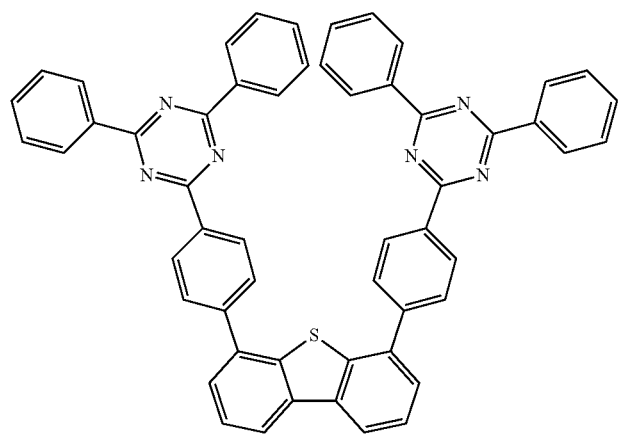
[ET-1-L]
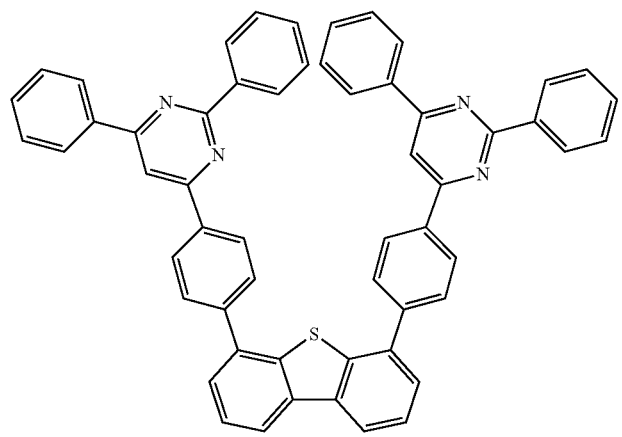
[ET-1-M]
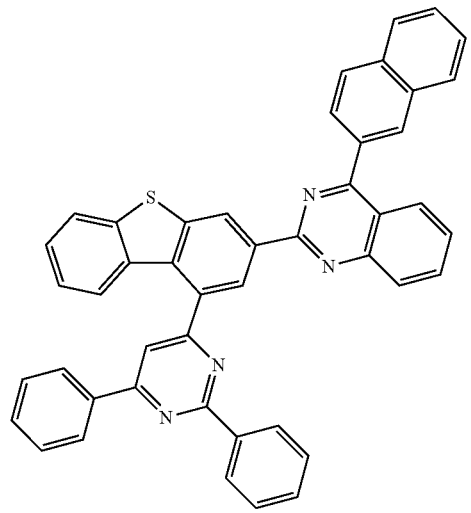
[ET-1-N]
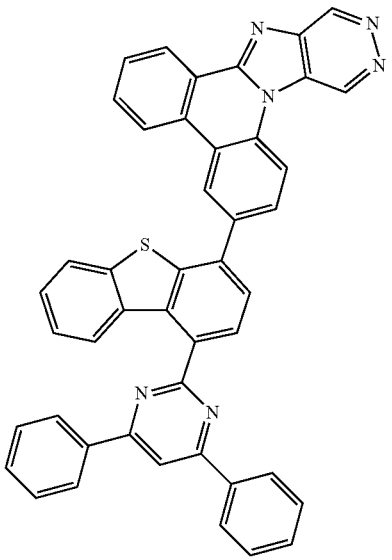

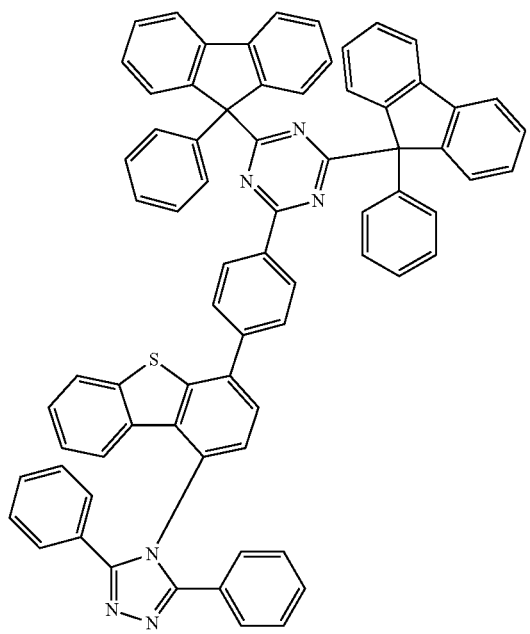

[ET-1-O]

The driving voltage and light emitting efficiency were measured at the current density of 10 mA/cm² for the organic light emitting devices manufactured in the Experimental Examples 1-1 to 1-25 and Comparative Examples 1-1 to 1-15, and the time (T90) at which the luminance became 90% relative to the initial luminance at the current density of 20 mA/cm² was measured. The results are shown in Tables 1 and 2 below.

TABLE 1

| | Compound | Voltage (V) | Efficiency (Cd/A) | Color coordinate (x, y) | Lifetime(h) T90 at 20 mA/Cm² |
|---|---|---|---|---|---|
| Experimental Example 1-1 | E1 | 4.30 | 5.55 | (0.142, 0.097) | 148 |
| Experimental Example 1-2 | E2 | 4.31 | 5.60 | (0.142, 0.096) | 140 |
| Experimental Example 1-3 | E3 | 4.40 | 5.22 | (0.142, 0.096) | 170 |
| Experimental Example 1-4 | E4 | 4.24 | 5.70 | (0.142, 0.096) | 127 |
| Experimental Example 1-5 | E5 | 4.36 | 5.51 | (0.142, 0.096) | 153 |
| Experimental Example 1-6 | E6 | 4.18 | 5.75 | (0.142, 0.097) | 121 |
| Experimental Example 1-7 | E7 | 4.32 | 5.58 | (0.142, 0.096) | 138 |
| Experimental Example 1-8 | E8 | 4.30 | 5.44 | (0.142, 0.099) | 161 |
| Experimental Example 1-9 | E9 | 4.18 | 5.76 | (0.142, 0.096) | 120 |
| Experimental Example 1-10 | E10 | 4.40 | 5.21 | (0.142, 0.098) | 172 |
| Experimental Example 1-11 | E11 | 4.37 | 5.47 | (0.142, 0.096) | 160 |
| Experimental Example 1-12 | E12 | 4.31 | 5.50 | (0.142, 0.097) | 140 |
| Experimental Example 1-13 | E13 | 4.41 | 5.20 | (0.142, 0.096) | 180 |
| Experimental Example 1-14 | E14 | 4.39 | 5.79 | (0.142, 0.097) | 130 |
| Experimental Example 1-15 | E15 | 4.16 | 5.79 | (0.142, 0.097) | 131 |
| Experimental Example 1-16 | E16 | 4.30 | 5.60 | (0.142, 0.097) | 139 |
| Experimental Example 1-17 | E17 | 4.28 | 5.63 | (0.142, 0.097) | 126 |
| Experimental Example 1-18 | E18 | 4.16 | 5.80 | (0.142, 0.096) | 122 |

TABLE 1-continued

| | Compound | Voltage (V) | Efficiency (Cd/A) | Color coordinate (x, y) | Lifetime(h) T90 at 20 mA/Cm$^2$ |
|---|---|---|---|---|---|
| Experimental Example 1-19 | E19 | 4.33 | 5.57 | (0.142, 0.096) | 144 |
| Experimental Example 1-20 | E20 | 4.40 | 5.33 | (0.142, 0.097) | 177 |
| Experimental Example 1-21 | E21 | 4.44 | 5.29 | (0.142, 0.096) | 160 |
| Experimental Example 1-22 | E22 | 4.30 | 5.52 | (0.142, 0.096) | 166 |
| Experimental Example 1-23 | E23 | 4.27 | 5.60 | (0.142, 0.096) | 138 |
| Experimental Example 1-24 | E24 | 4.39 | 5.44 | (0.142, 0.096) | 177 |
| Experimental Example 1-25 | E25 | 4.30 | 5.55 | (0.142, 0.097) | 148 |

TABLE 2

| | Compound | Voltage (V) | Efficiency (cd/A) | Color coordinate (x, y) | Lifetime(h) T90 at 20 mA/Cm$^2$ |
|---|---|---|---|---|---|
| Comparative Example 1-1 | ET-1-A | 5.31 | 3.05 | (0.142, 0.098) | 40 |
| Comparative Example 1-2 | ET-1-B | 5.00 | 4.02 | (0.142, 0.102) | 38 |
| Comparative Example 1-3 | ET-1-C | 5.11 | 3.99 | (0.142, 0.096) | 42 |
| Comparative Example 1-4 | ET-1-D | 5.23 | 3.87 | (0.142, 0.096) | 50 |
| Comparative Example 1-5 | ET-1-E | 5.77 | 2.00 | (0.142, 0.096) | 17 |
| Comparative Example 1-6 | ET-1-F | 4.99 | 4.10 | (0.142, 0.096) | 39 |
| Comparative Example 1-7 | ET-1-G | 5.00 | 3.21 | (0.142, 0.096) | 55 |
| Comparative Example 1-8 | ET-1-H | 5.01 | 3.24 | (0.142, 0.096) | 52 |
| Comparative Example 1-9 | ET-1-I | 4.98 | 3.87 | (0.142, 0.096) | 27 |
| Comparative Example 1-10 | ET-1-J | 5.08 | 3.30 | (0.142, 0.096) | 57 |
| Comparative Example 1-11 | ET-1-K | 5.07 | 3.33 | (0.142, 0.097) | 58 |
| Comparative Example 1-12 | ET-1-L | 4.99 | 3.85 | (0.142, 0.097) | 29 |
| Comparative Example 1-13 | ET-1-M | 5.55 | 3.00 | (0.142, 0.097) | 41 |
| Comparative Example 1-14 | ET-1-N | 5.21 | 3.11 | (0.142, 0.097) | 44 |
| Comparative Example 1-15 | ET-1-O | 5.33 | 3.01 | (0.142, 0.097) | 33 |

As shown in Tables 1 and 2, it is confirmed that the heterocyclic compound represented by Chemical Formula 1 according to one embodiment of the present disclosure can be used for an organic material layer capable of simultaneously performing electron injection and electron transport of the organic light emitting device.

Specifically, when comparing Experimental Examples 1-1 to 1-25 with Comparative Examples 1-1, 1-2, 1-3, 1-6, 1-13, 1-14 and 1-15, it is confirmed that the compounds in which different $Ar_1$ is substituted in dibenzofuran or dibenzothiophene skeleton exhibit excellent characteristics in terms of driving voltage, efficiency and lifetime of the organic light emitting device, as compared with the compounds having a substituent group other than $Ar_1$ in the dibenzofuran or dibenzothiophene skeleton.

Further, when comparing Experimental Examples 1-1 to 1-25 with Comparative Examples 1-5, it is confirmed that the compounds in which different $Ar_1$ is substituted in dibenzofuran or dibenzothiophene skeleton exhibit excellent characteristics in the organic light emitting device, as compared with the compounds in which identical $Ar_1$ are substituted in dibenzofuran or dibenzothiophene skeleton.

Further, when comparing Experimental Examples 1-1 to 1-25 with Comparative Examples 1-4, 1-7, 1-8, 1-9, 1-10, 1-11 and 1-12, it is confirmed that the compound in which different $Ar_1$ are substituted in dibenzofuran or dibenzothiophene skeleton exhibit excellent characteristics in the organic light emitting device, as compared with Compounds in which $Ar_1$ are substituted on different phenyl groups in dibenzofuran or dibenzothiophene skeleton.

The heterocyclic compound represented by Chemical Formula 1 according to one embodiment of the present disclosure has excellent thermal stability, deep HOMO level of 6.0 eV or more, high triplet energy (ET) and hole stability, and thus can exhibit excellent characteristics.

In one embodiment of the present disclosure, when the heterocyclic compound represented by Chemical Formula 1 is used for an organic material layer capable of simultaneously performing electron injection and electron transport, the n-type dopant used in the art can be mixed and used.

Accordingly, the heterocyclic compound represented by Chemical Formula 1 according to one embodiment of the present disclosure has low driving voltage and high efficiency, and improve the reliability of the device due to the hole stability of the compound.

DESCRIPTION OF REFERENCE CHARACTERS

| 1: substrate | 2: anode |
|---|---|
| 3: light emitting layer | 4: cathode |
| 5: hole injection layer | 6: hole transport layer |
| 7: light emitting layer | 8: electron transport layer |

The invention claimed is:
1. A compound represented by Chemical Formula 1:

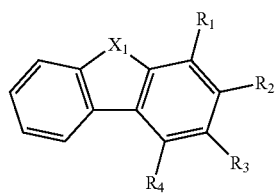

[Chemical Formula 1]

wherein, in Chemical Formula 1,
$X_1$ is O or S,
two of $R_1$ to $R_4$ are hydrogen, and the rest are $Ar_1$ which differ from each other,
$Ar_1$ is each independently -L-$Ar_2$,
L is each independently a direct bond, or substituted or unsubstituted $C_{6-60}$ arylene,
$Ar_2$ is each independently represented by Chemical Formula 2 below,

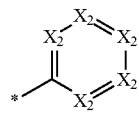

[Chemical Formula 2]

wherein, in Chemical Formula 2,
one, two, or three of $X_2$ are N, and the rest are $CR_5$,
$R_5$ is each independently hydrogen, deuterium, substituted or unsubstituted $C_{1-60}$ alkyl, substituted or unsubstituted $C_{6-60}$ aryl, or substituted or unsubstituted $C_{5-60}$ heteroaryl containing at least one heteroatom selected from the group consisting of N, O and S; with the proviso that when two of $X_2$ are N, $R_5$ is not a heteroaryl group.

2. The compound of claim 1, wherein
L is each independently a direct bond, phenylene, or naphthylene.

3. The compound of claim 1, wherein
$Ar_2$ represented by Chemical Formula 2 is any one selected from the group consisting of the following:

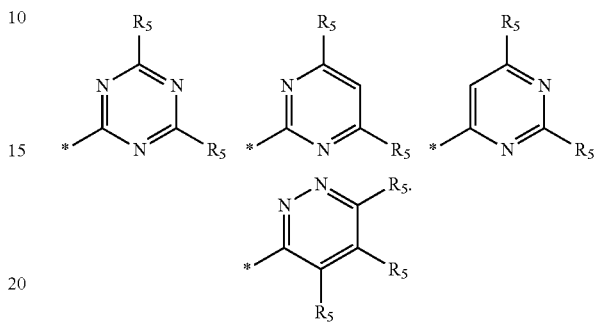

4. The compound of claim 1, wherein
in the Chemical Formula 2, at least one of $R_5$ is each independently substituted or unsubstituted $C_{6-60}$ aryl, or substituted or unsubstituted $C_{5-60}$ heteroaryl containing at least one heteroatom selected from the group consisting of N, O and S.

5. The compound of claim 1, wherein
$R_5$ is each independently hydrogen, phenyl, biphenylyl, naphthyl, or dibenzofuranyl.

6. The compound of claim 1, wherein
the compound represented by the Chemical Formula 1 is any one selected from the group consisting of the following:

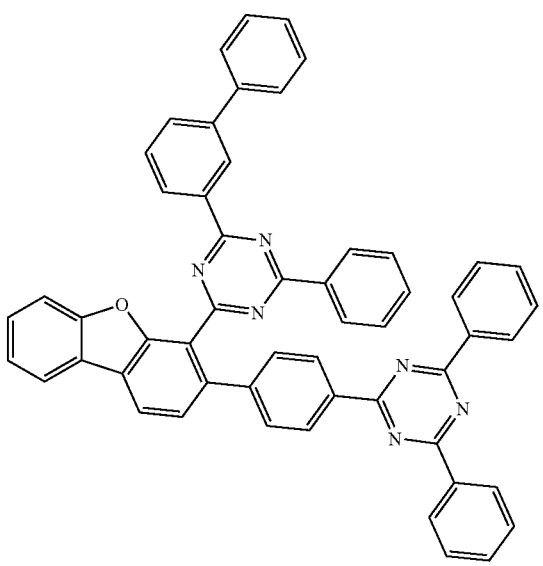

143
-continued
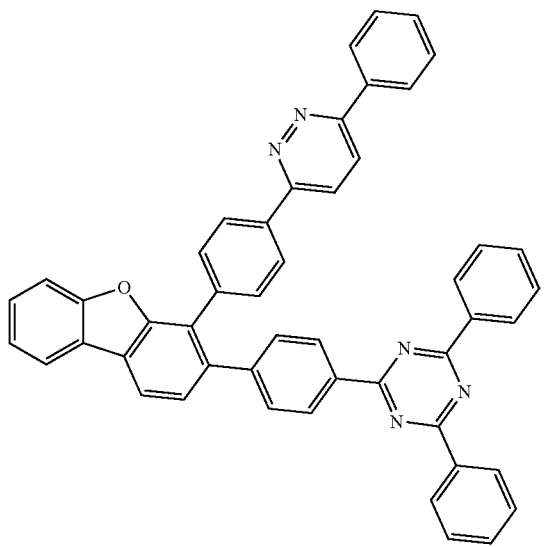
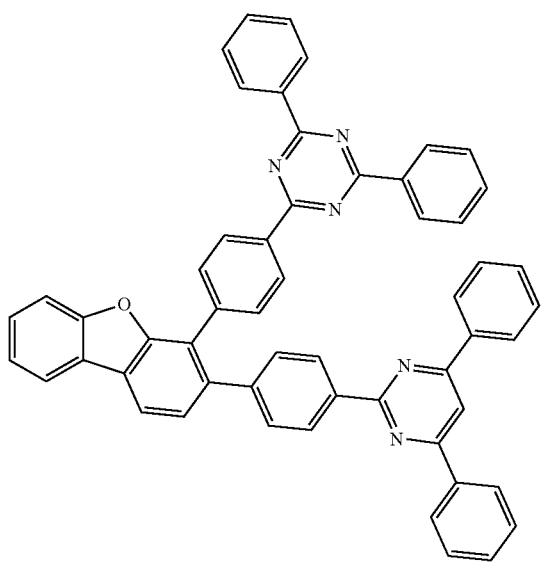
144
-continued
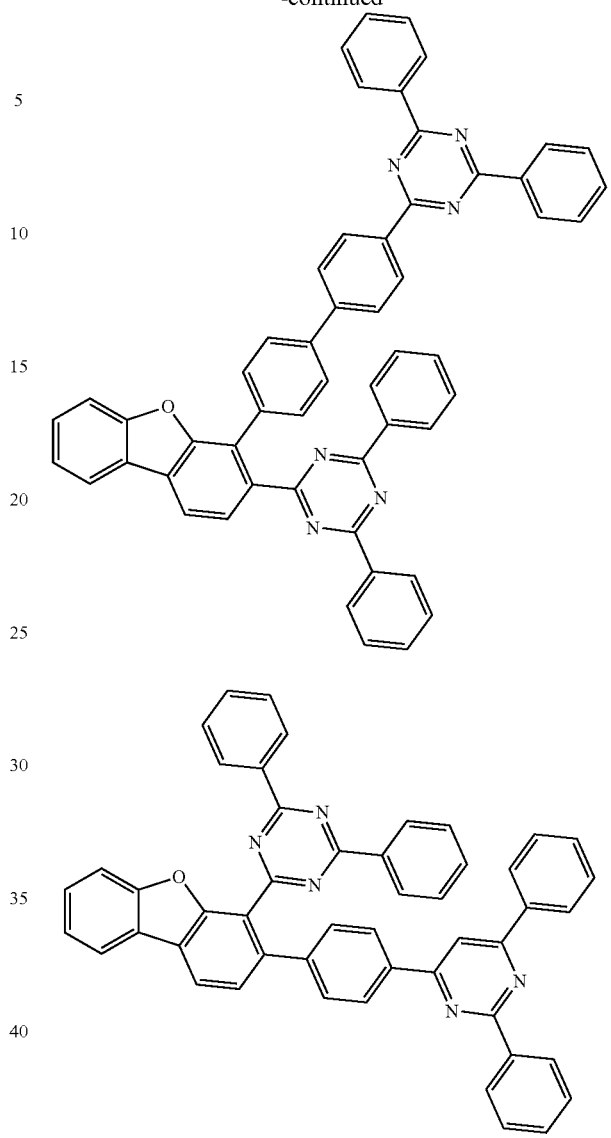
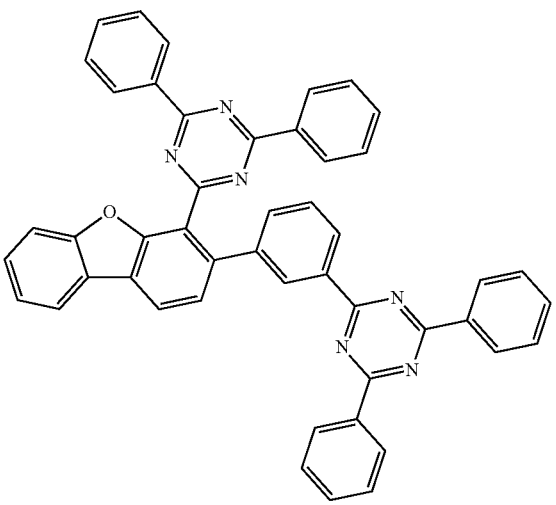

145
-continued
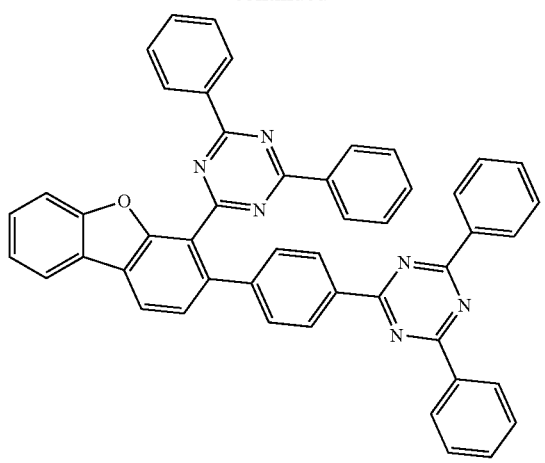
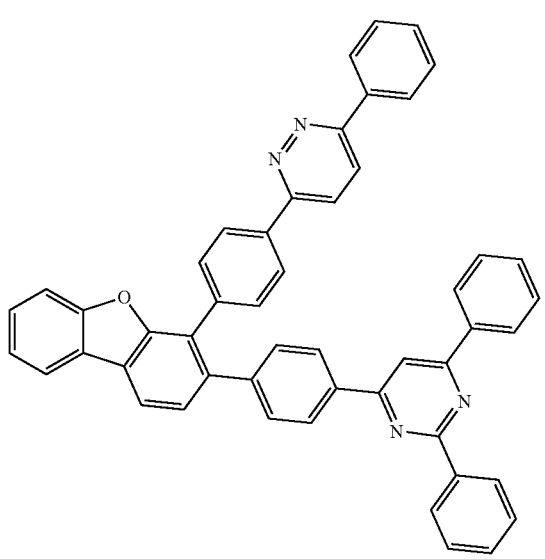
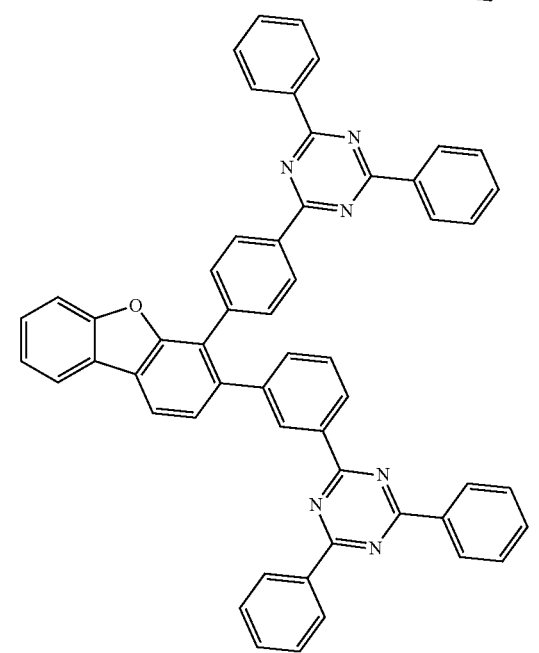
146
-continued
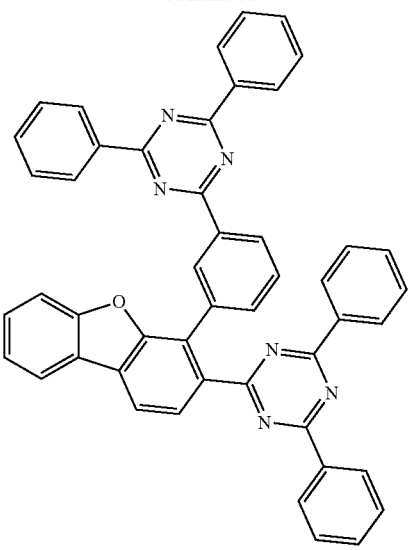
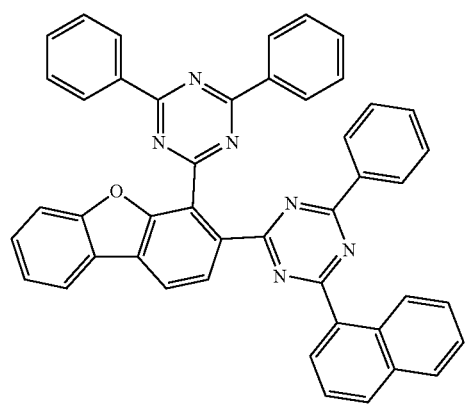
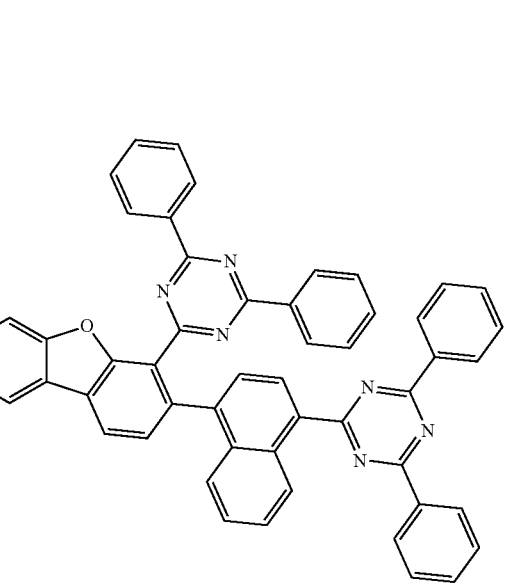

147
-continued
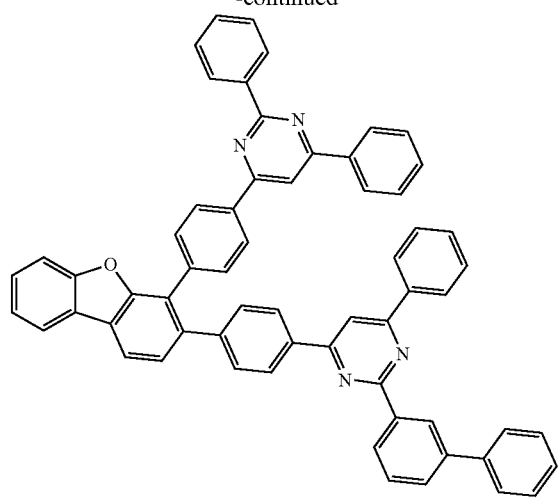
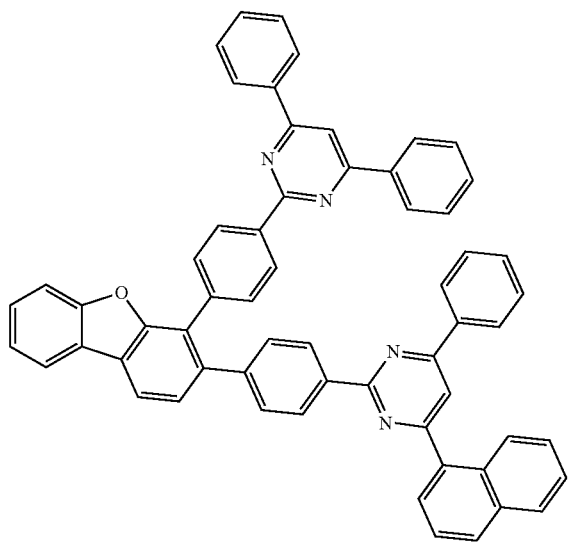
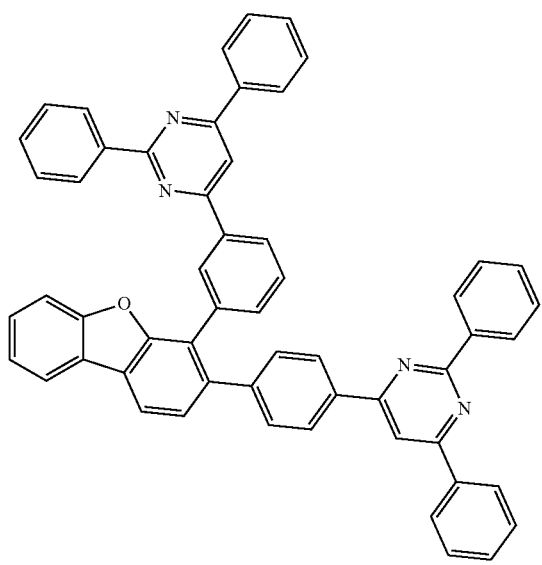
148
-continued
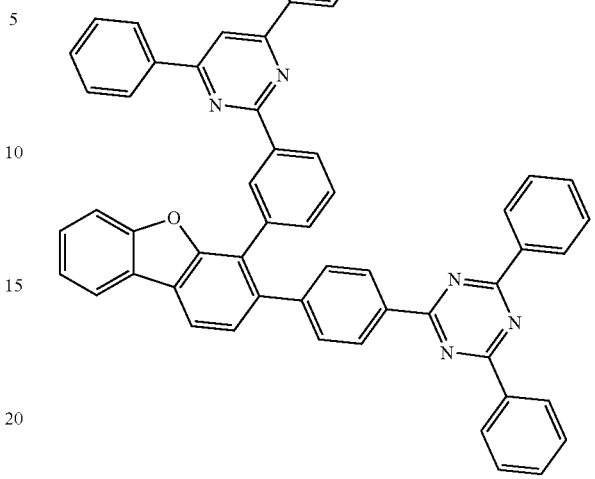
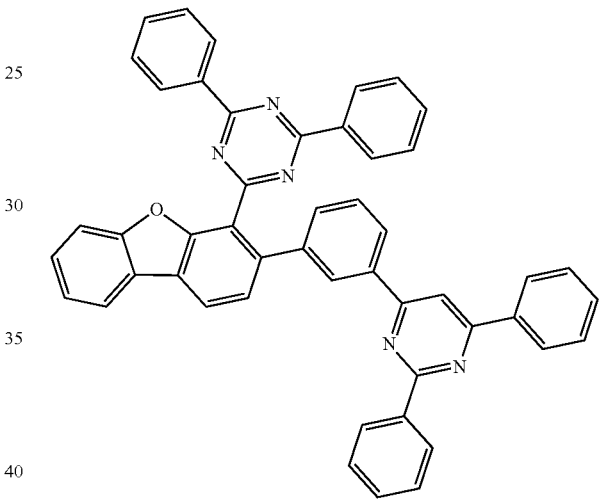
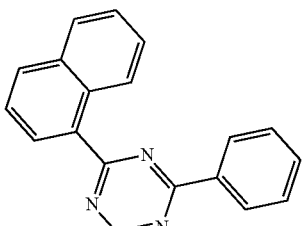
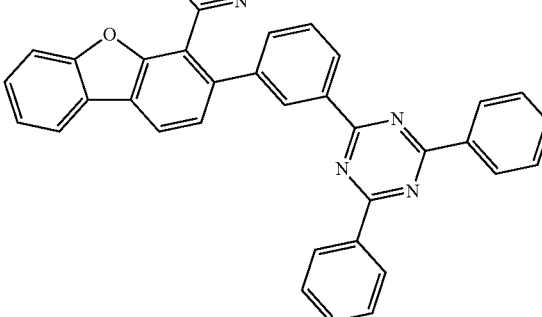

149
-continued
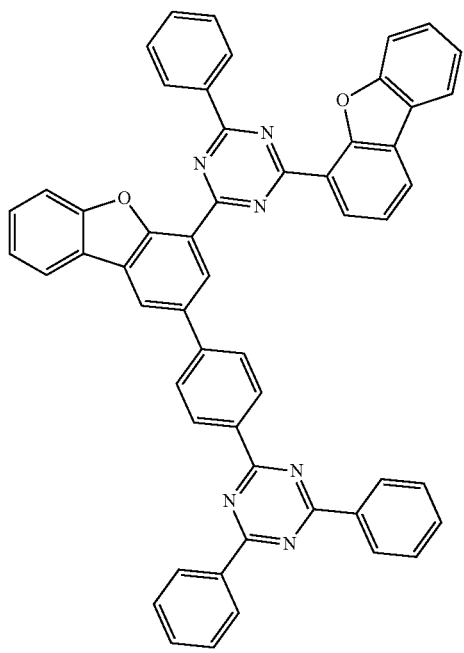
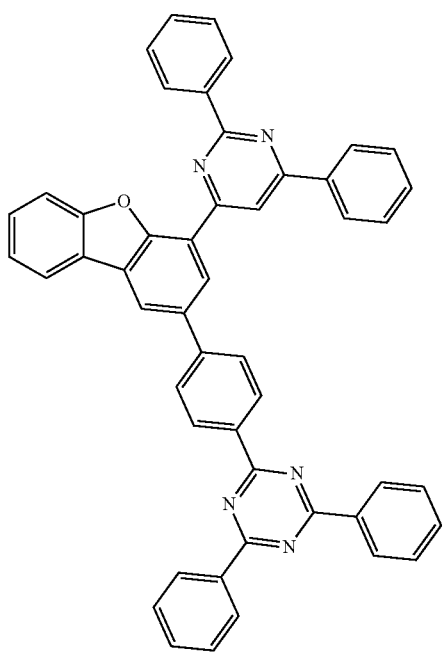
150
-continued
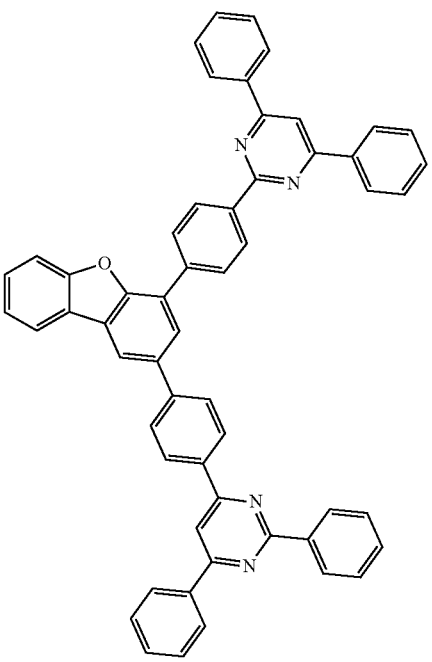
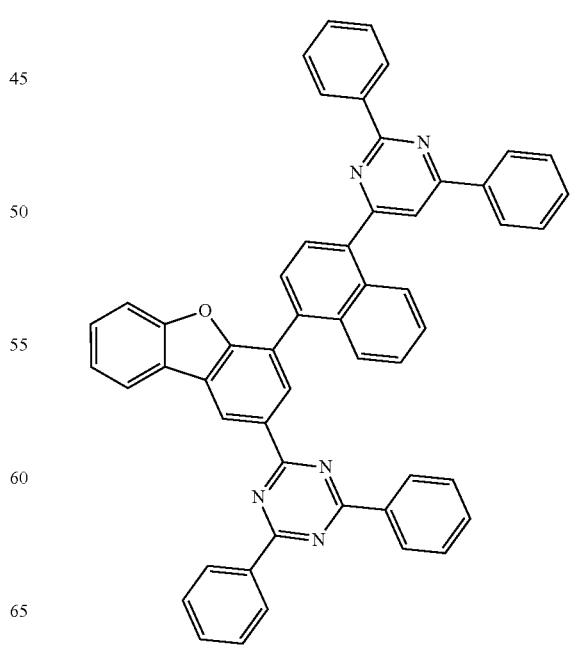

151
-continued
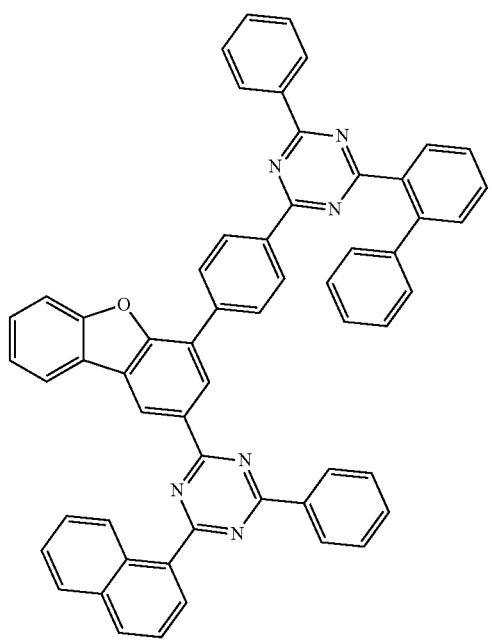
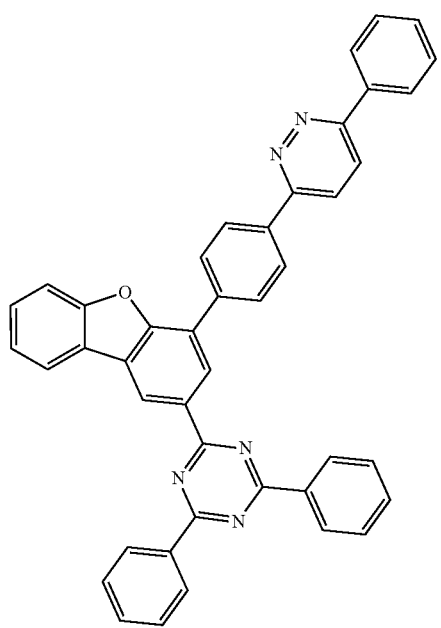
152
-continued
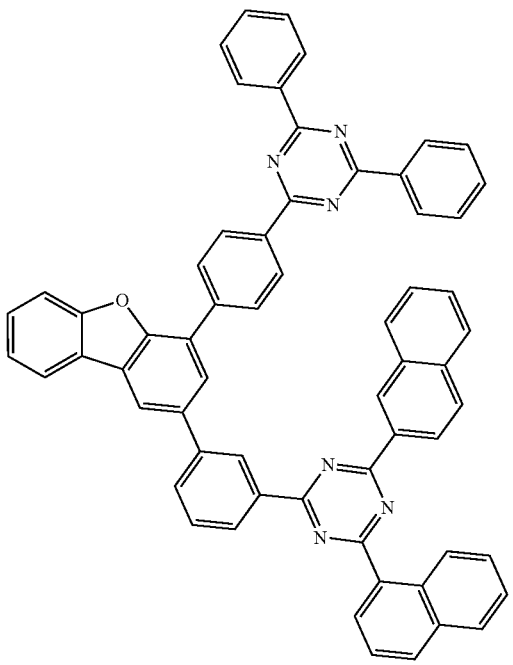
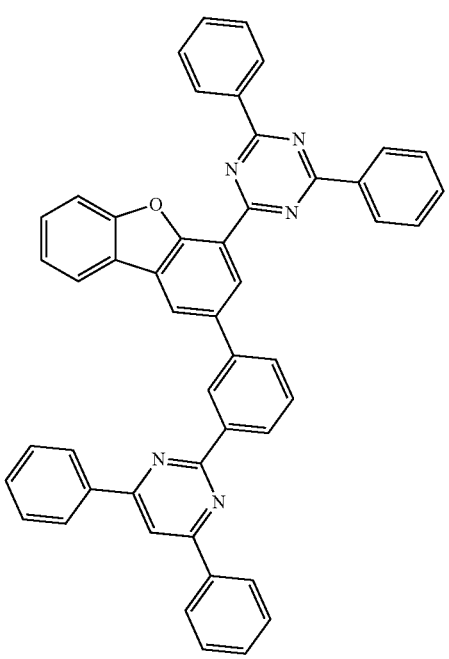

153
-continued
154
-continued
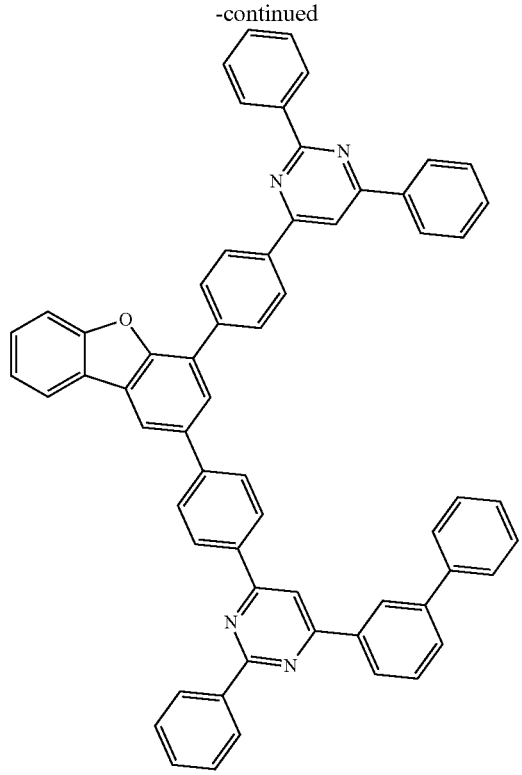
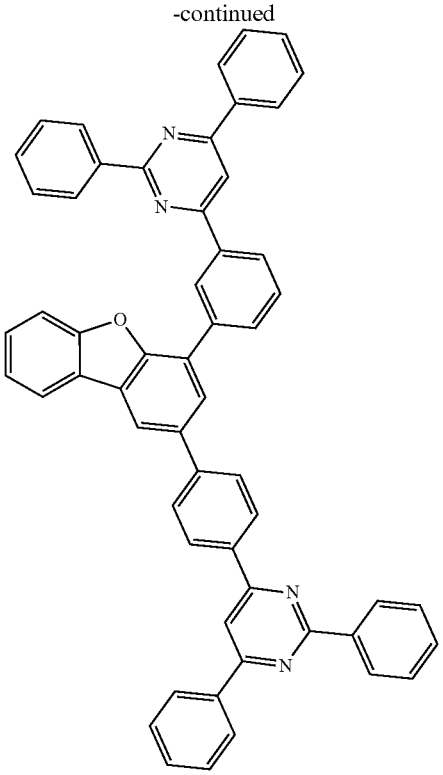
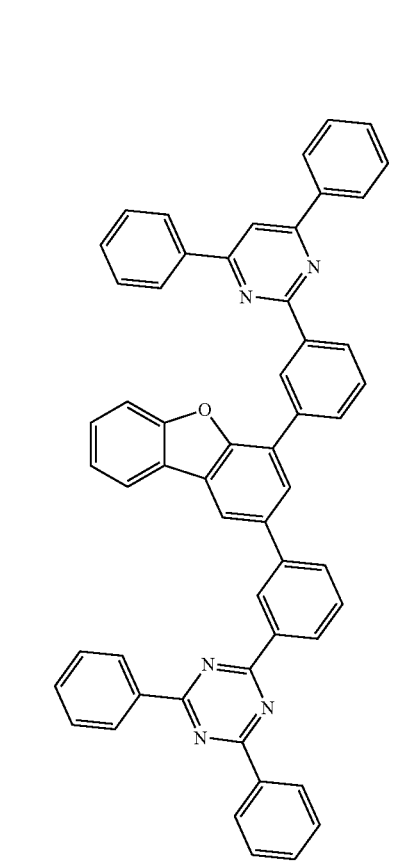

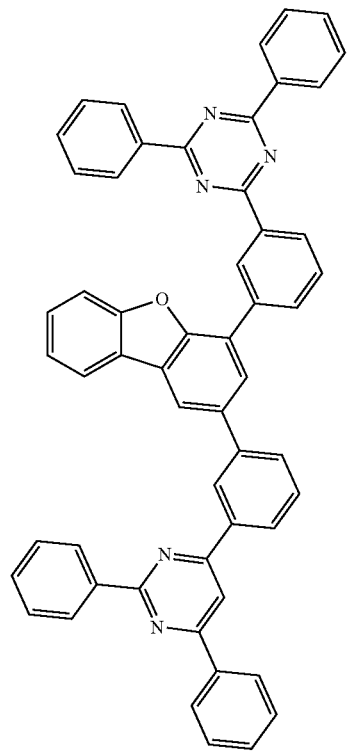
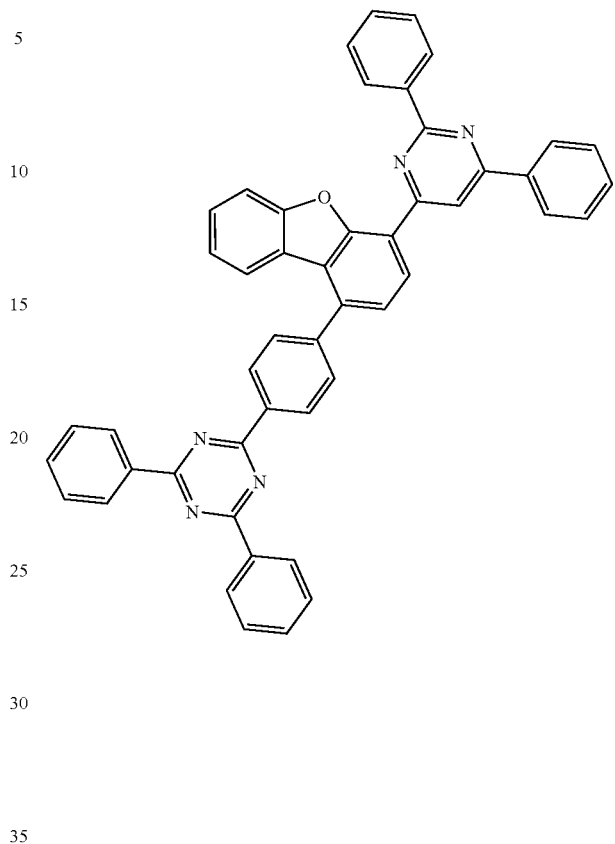
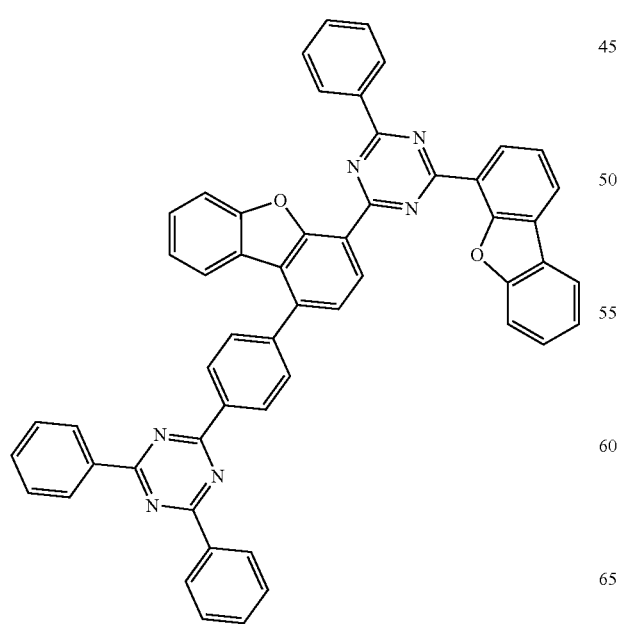
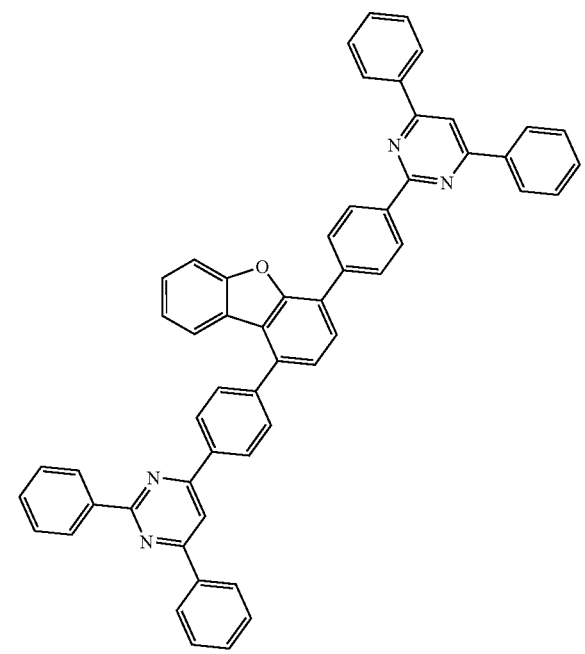

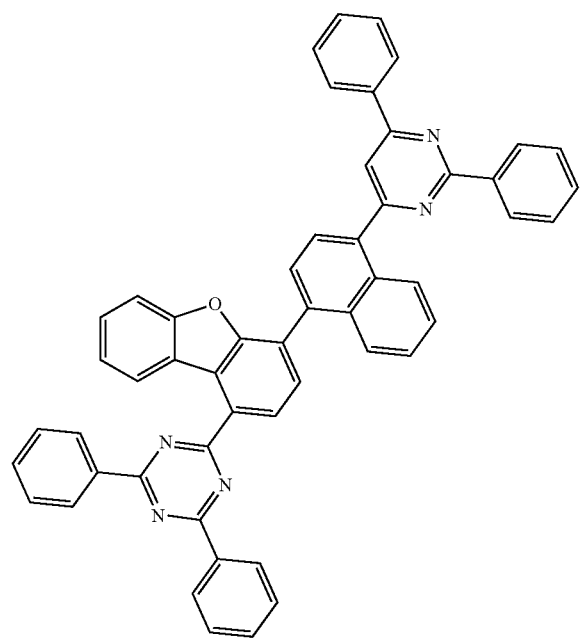
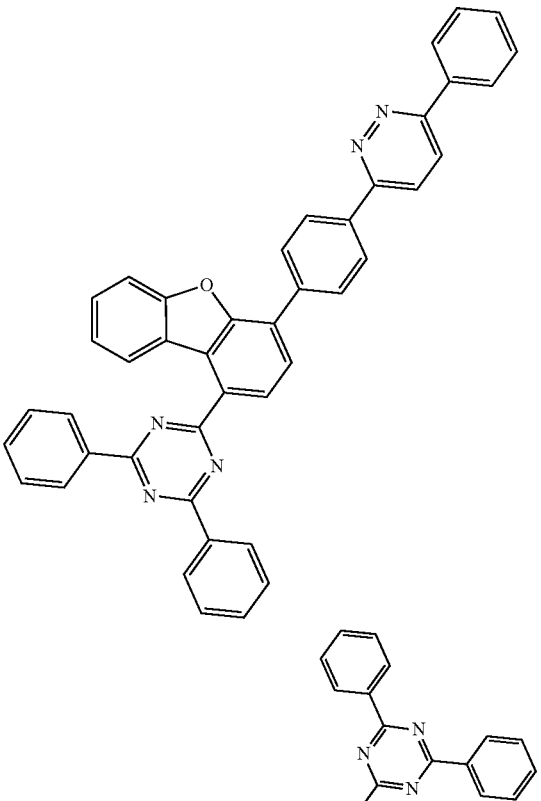
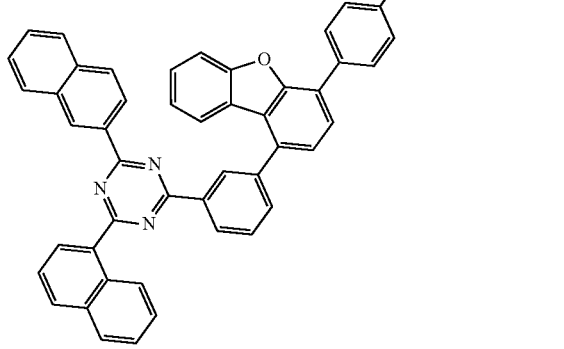
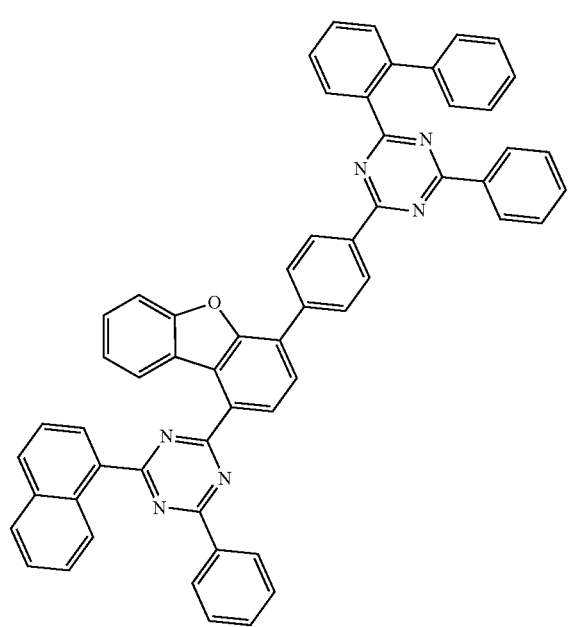
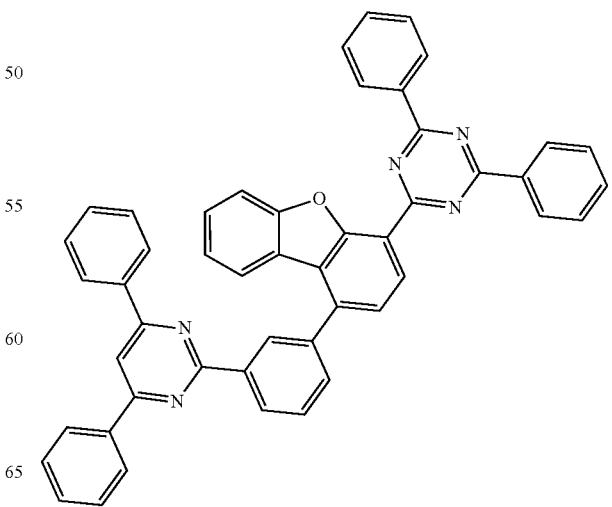

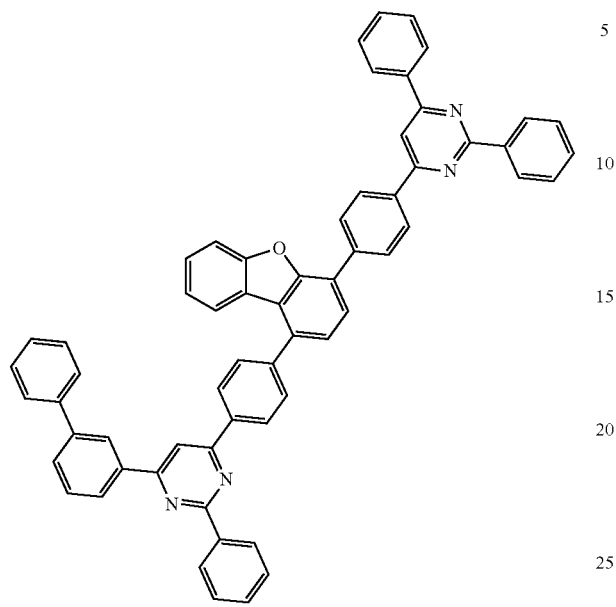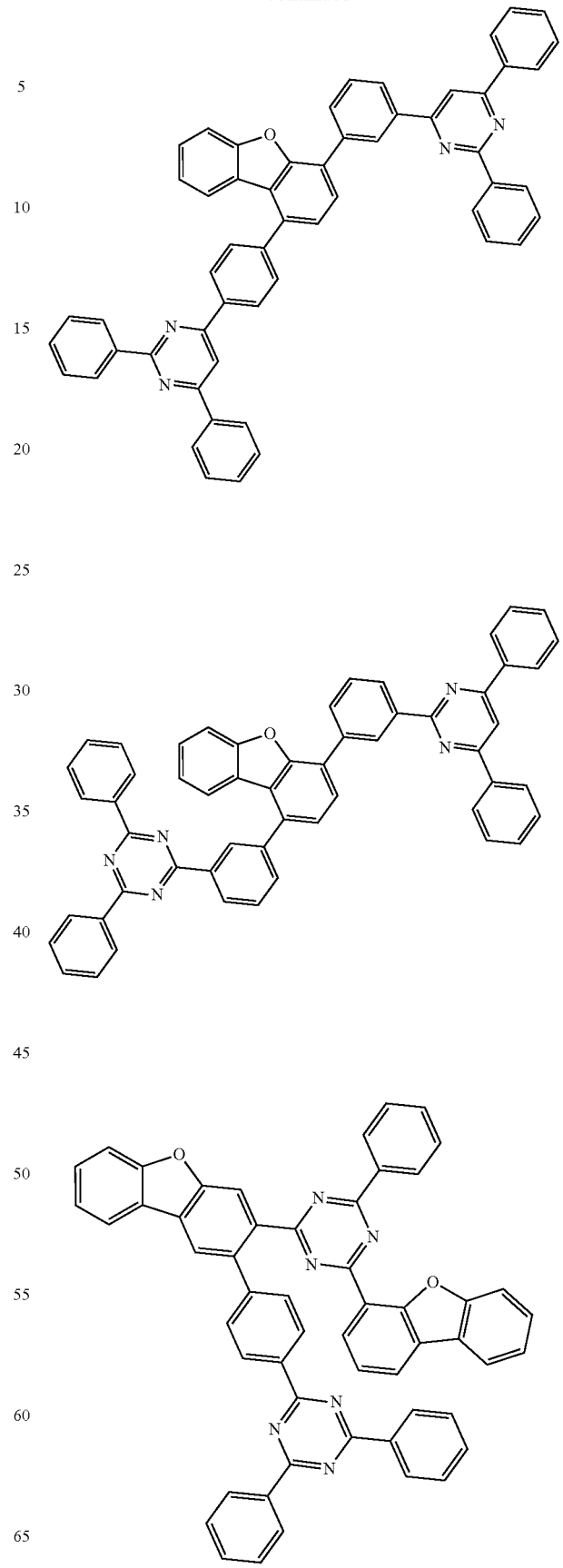

161
-continued
162
-continued
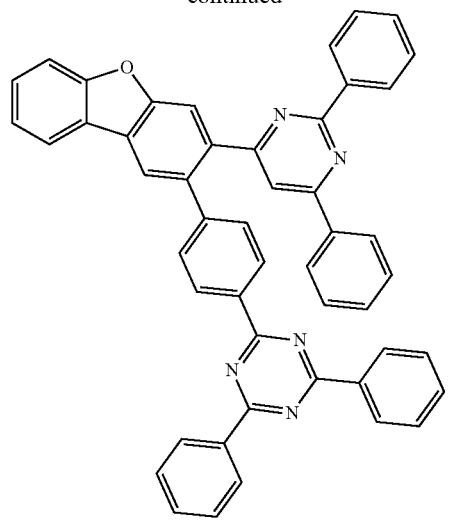
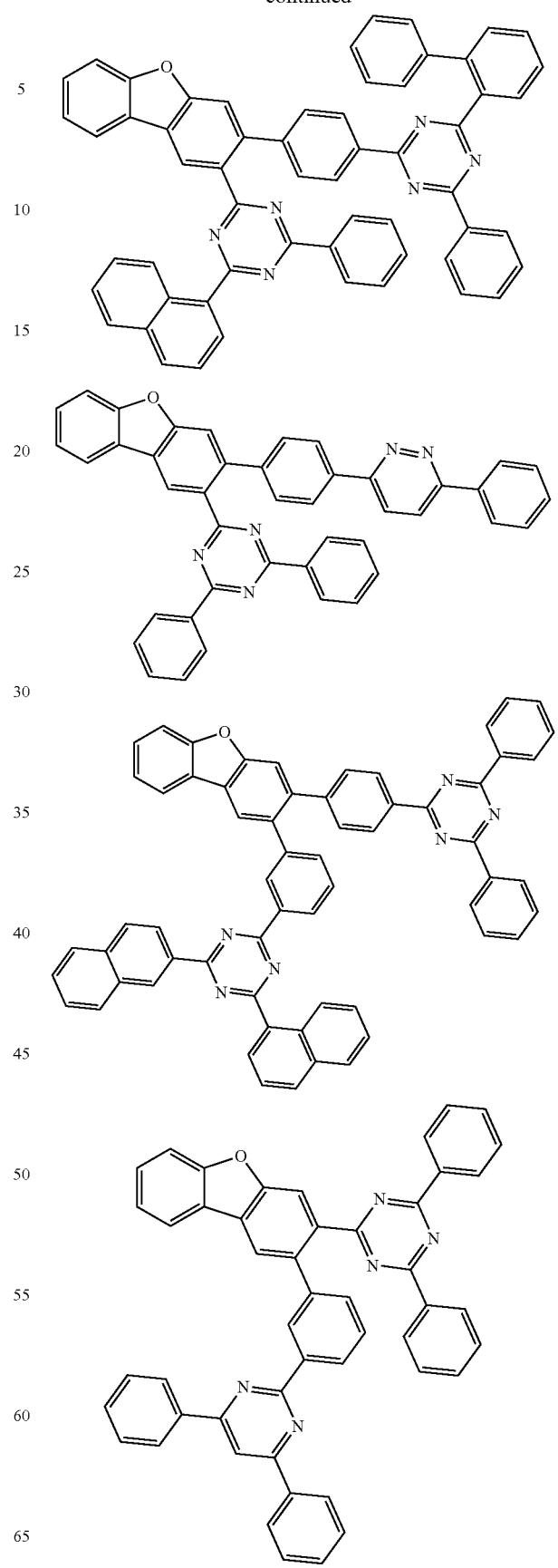

163
-continued
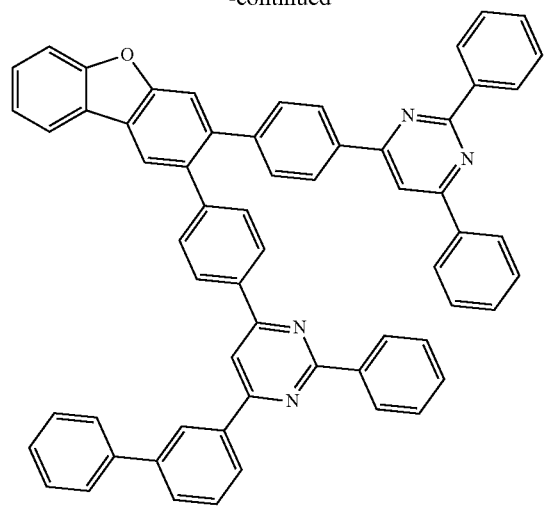
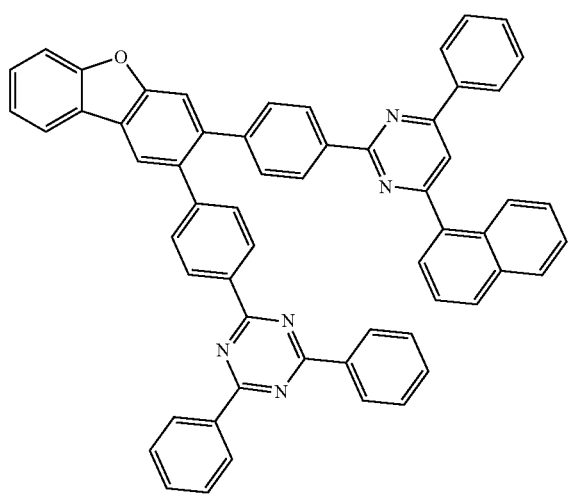
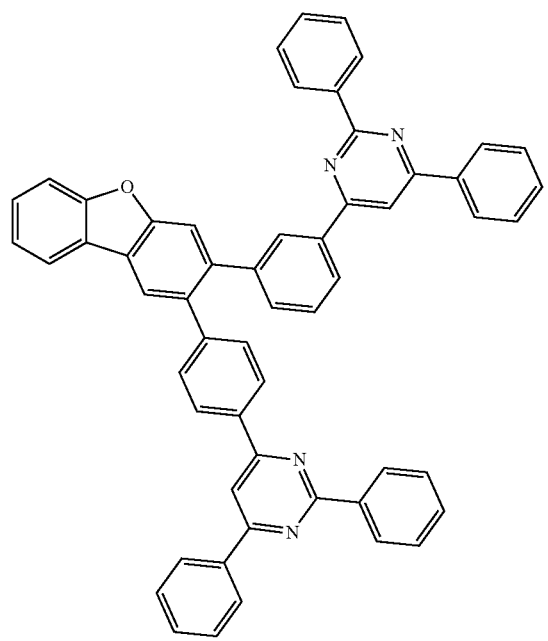
164
-continued
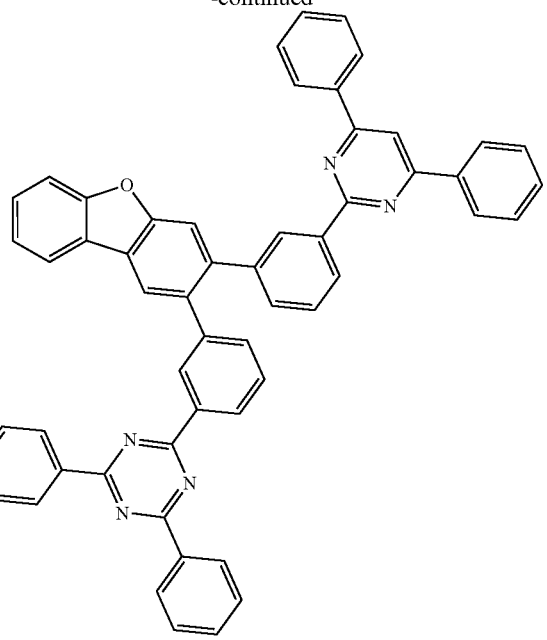
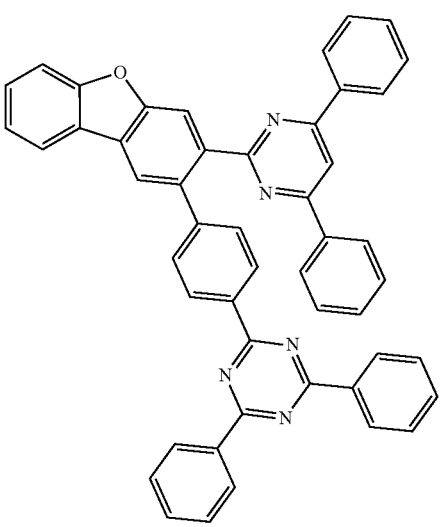
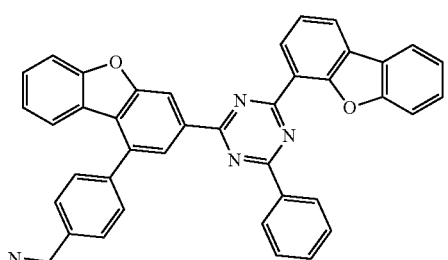
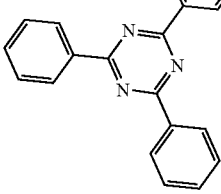

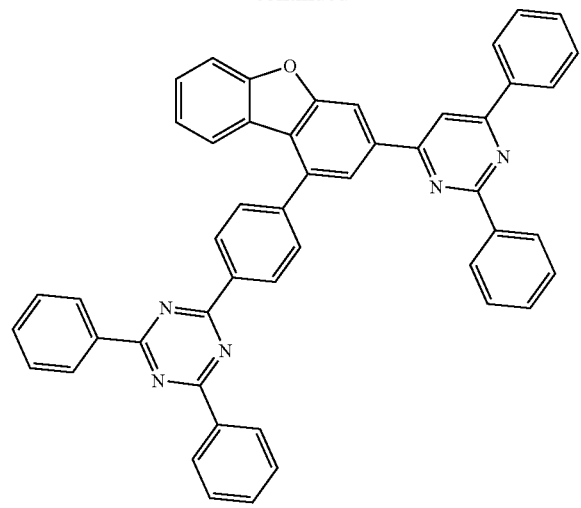
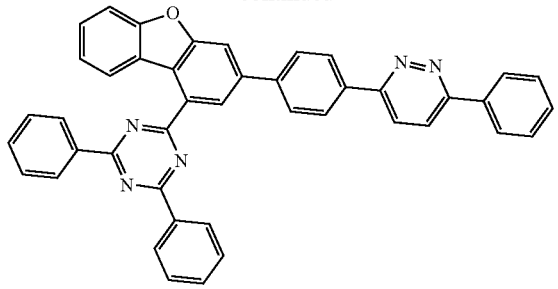
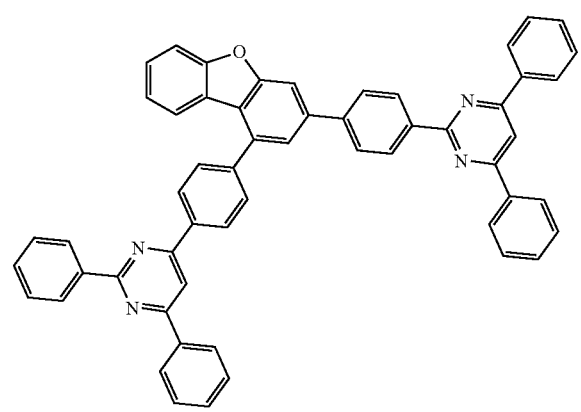
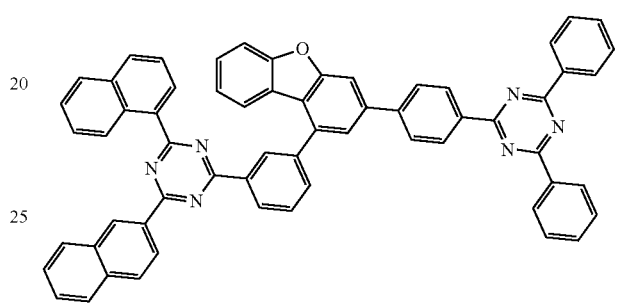
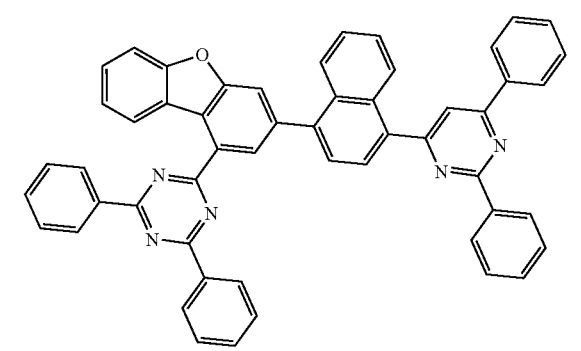
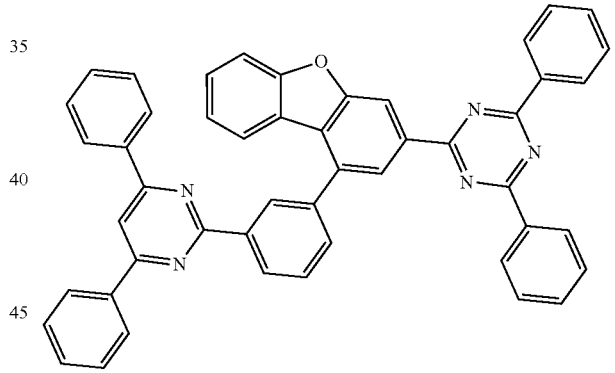
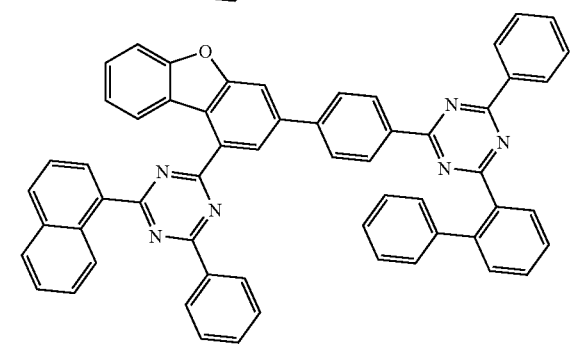
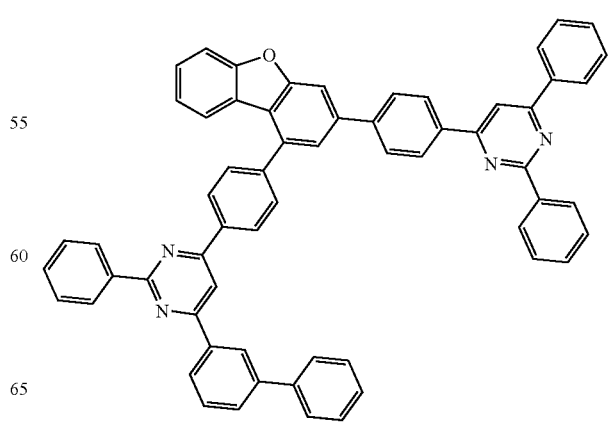

167
-continued
168
-continued
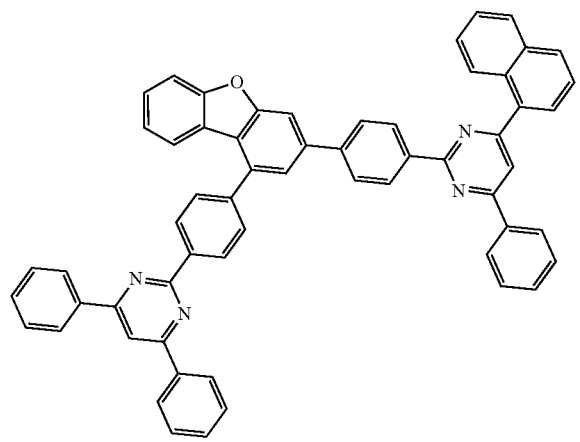
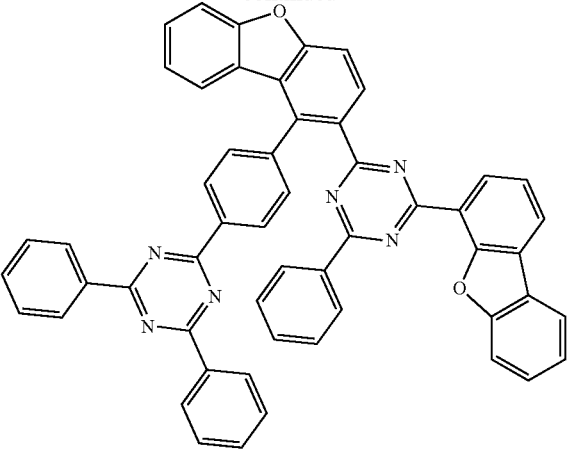

169 -continued
170 -continued
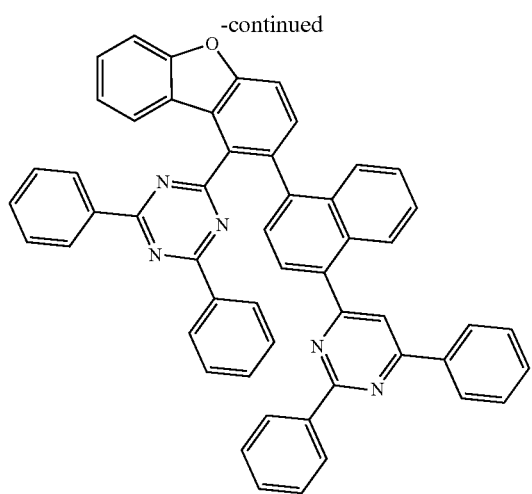
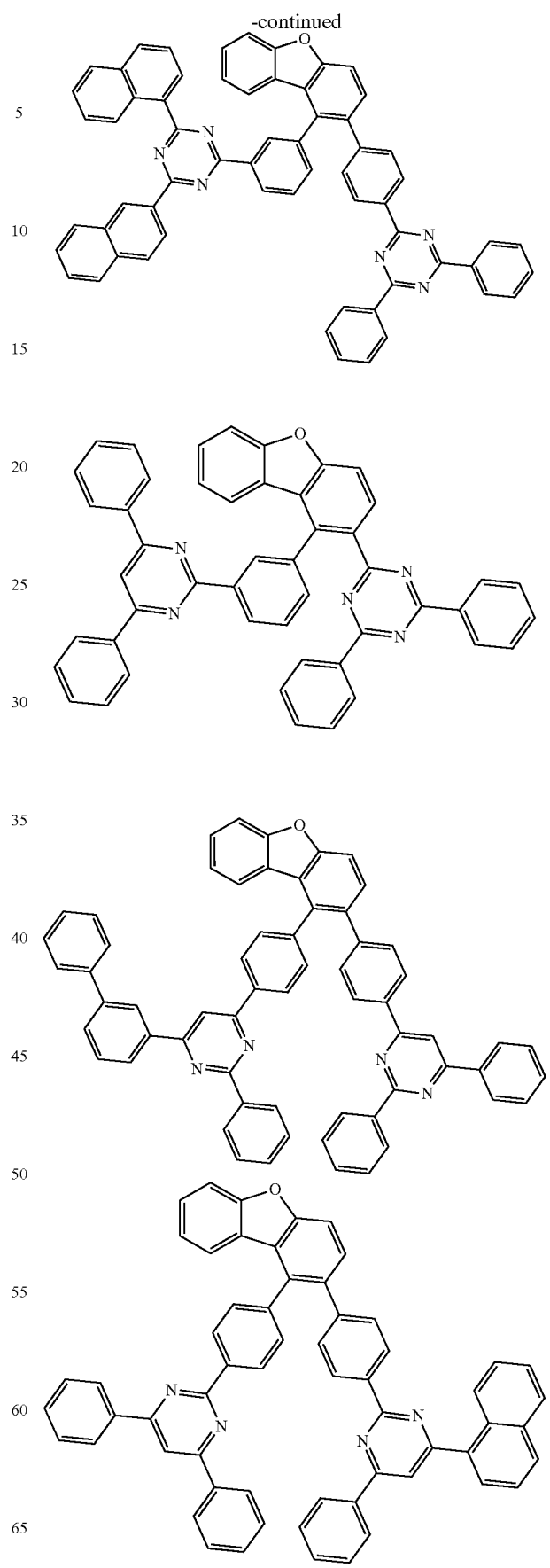

171
-continued
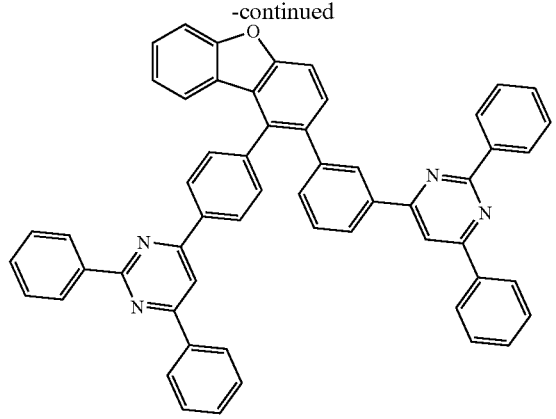
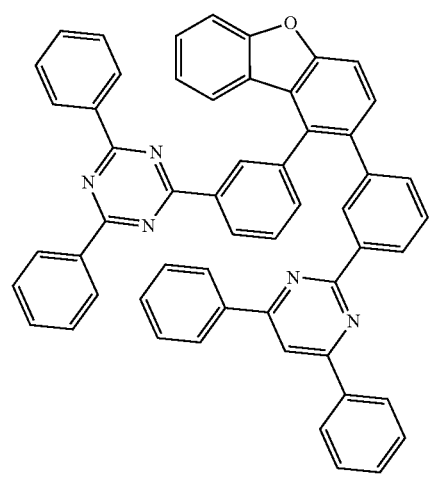
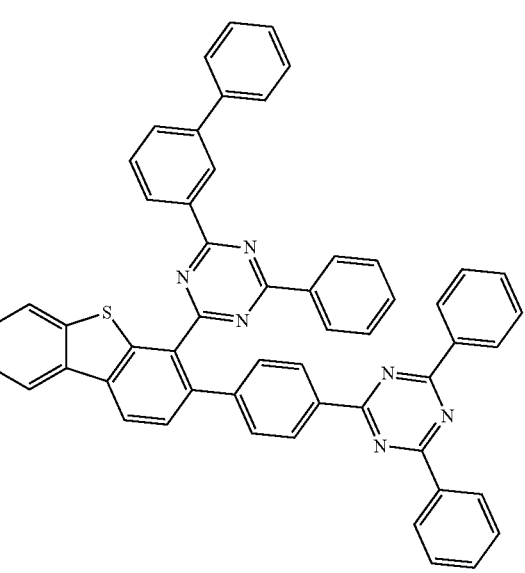
172
-continued
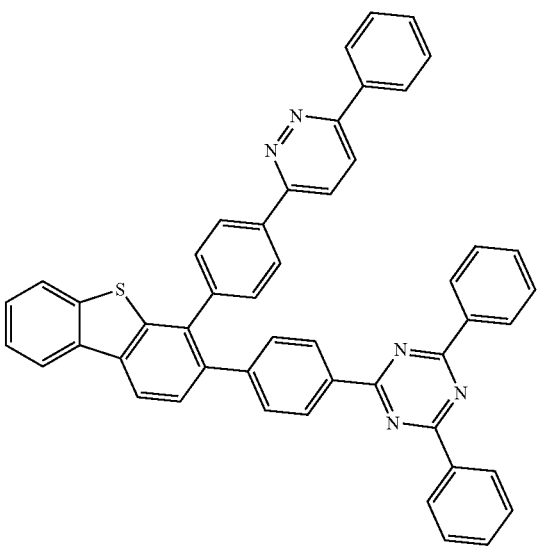
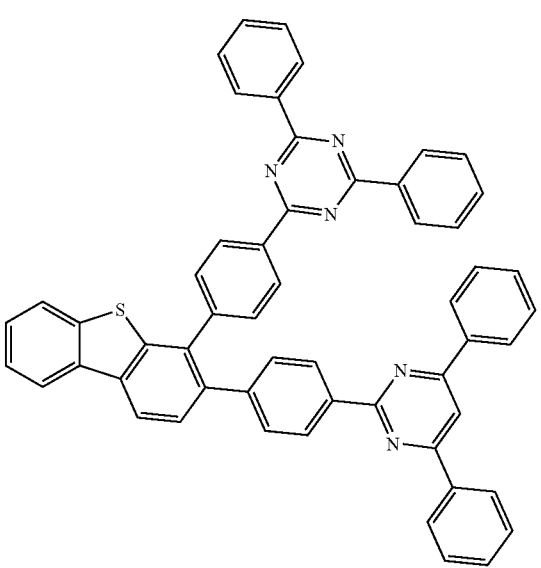

173
-continued
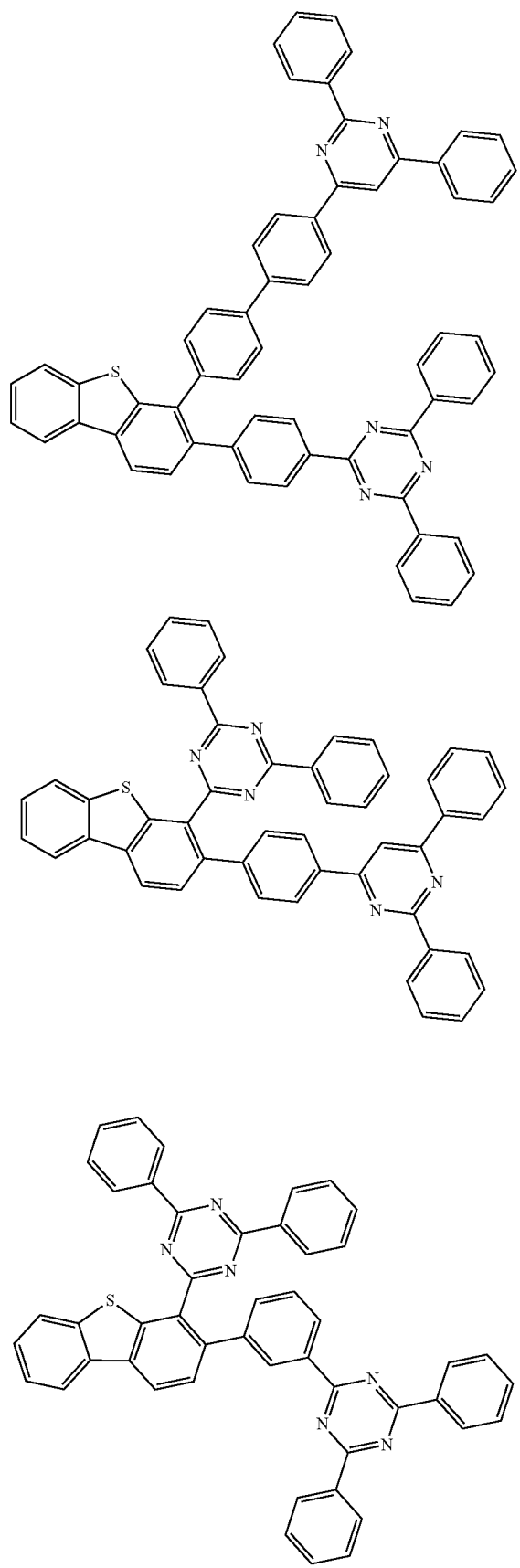
174
-continued
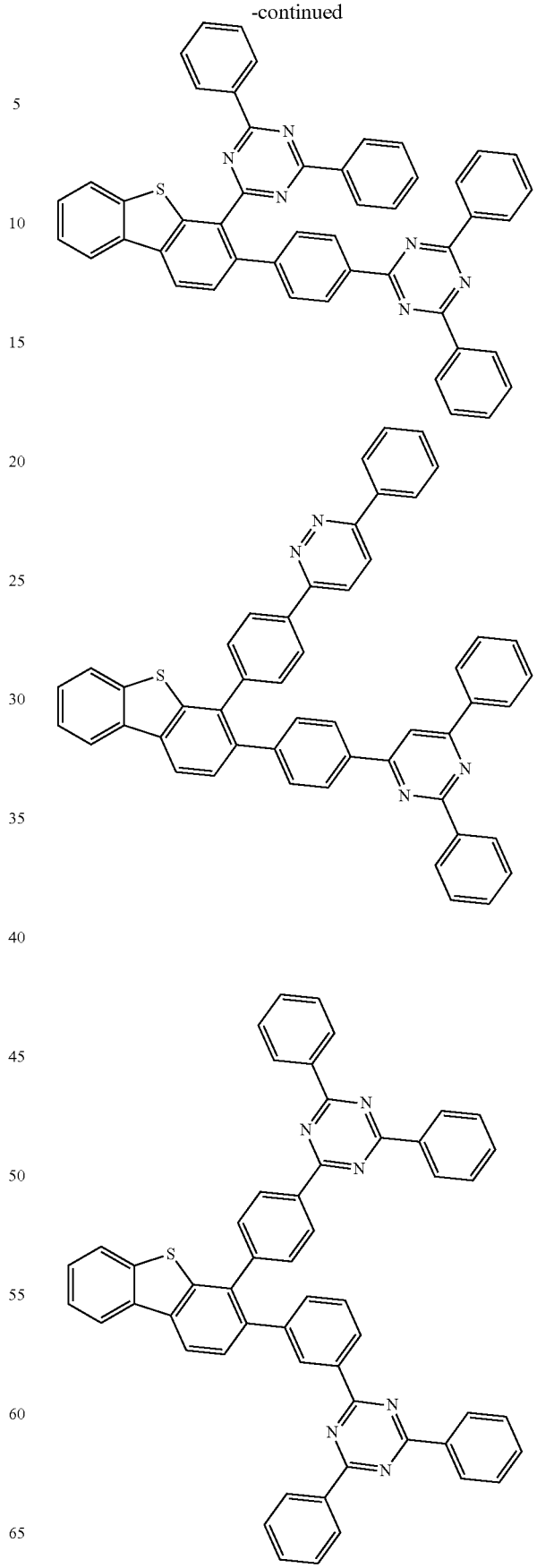

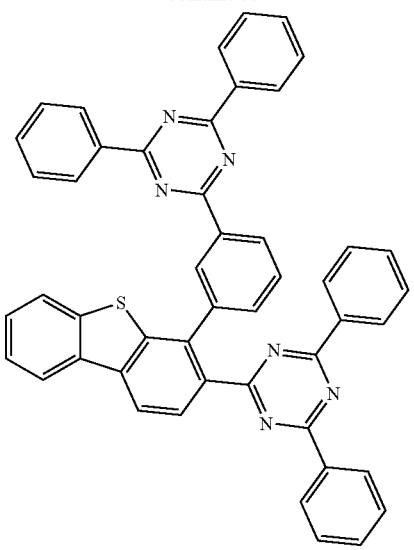
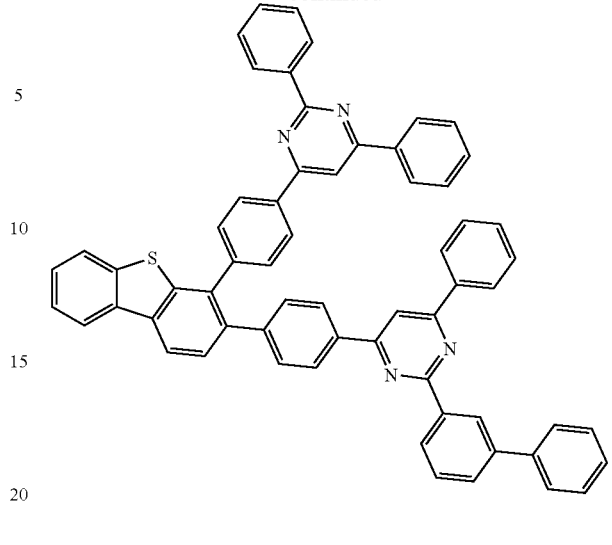
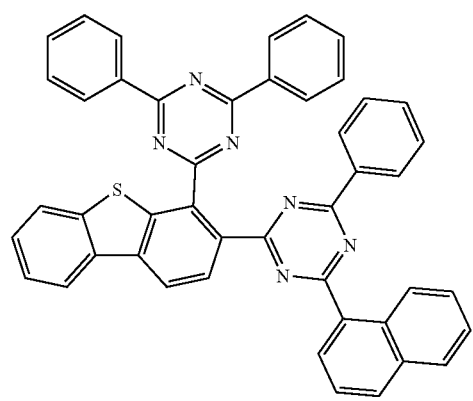
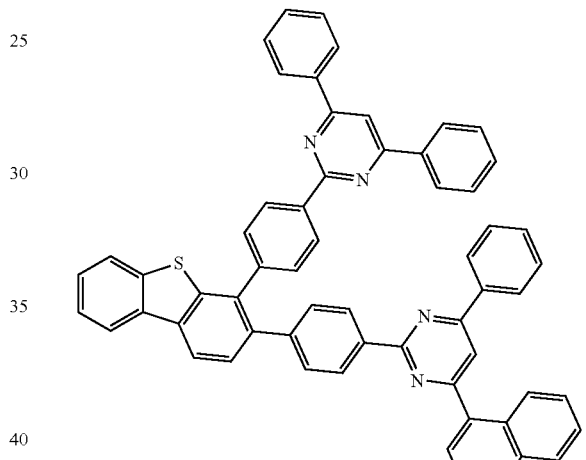
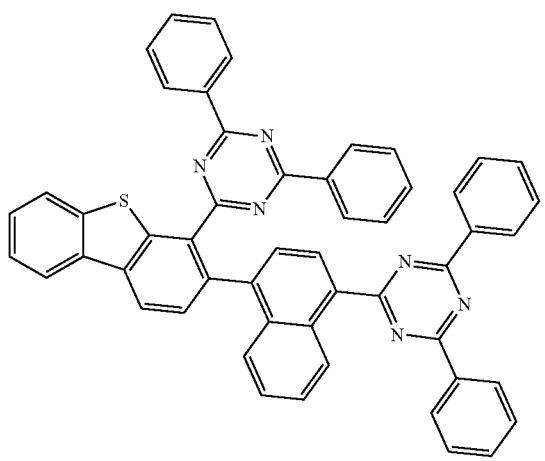
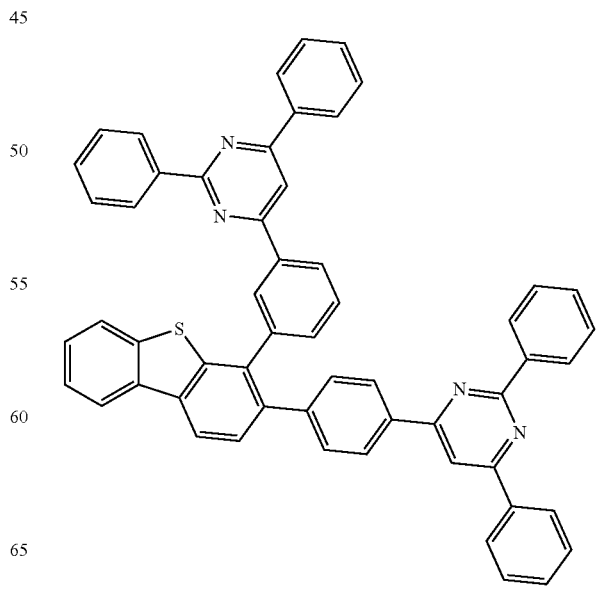

177
-continued
178
-continued
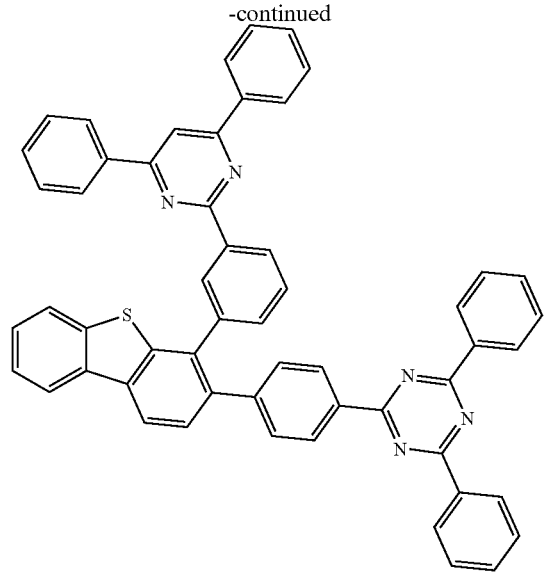
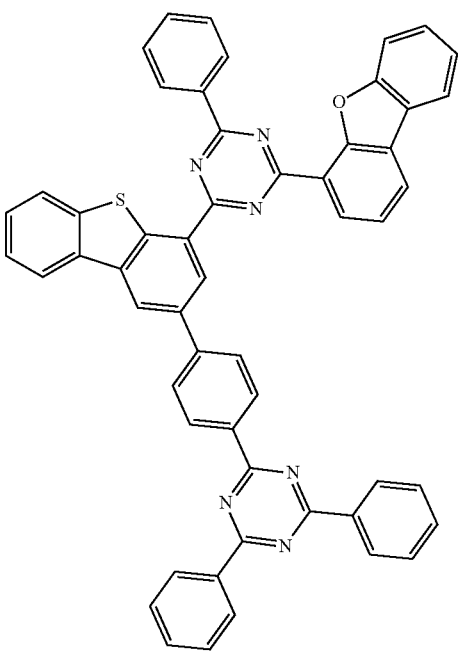
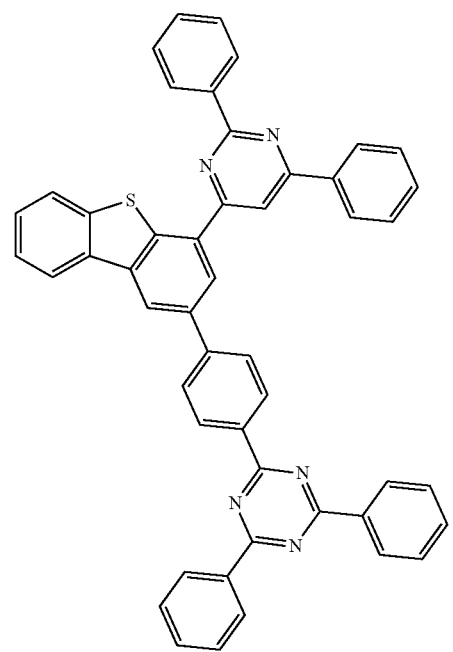

179
-continued
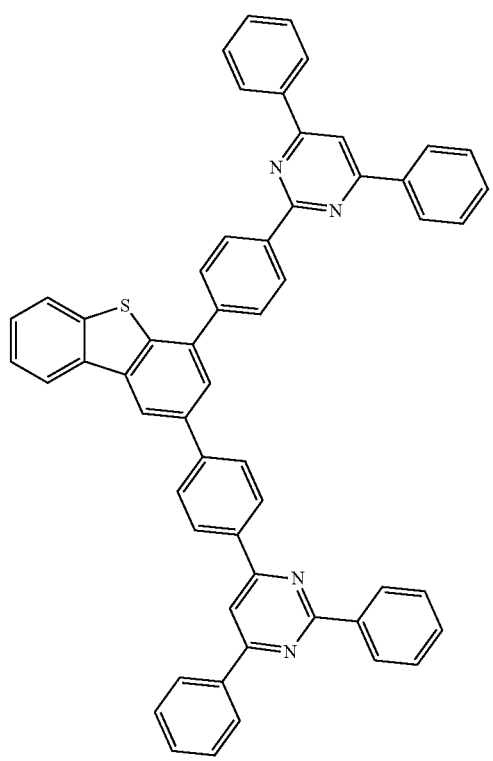
180
-continued
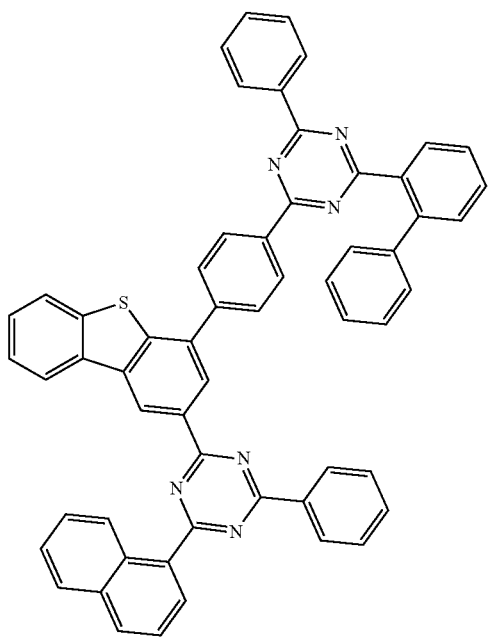
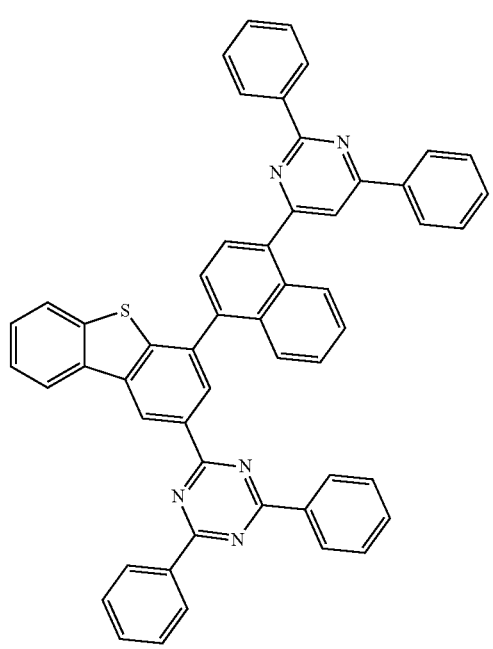
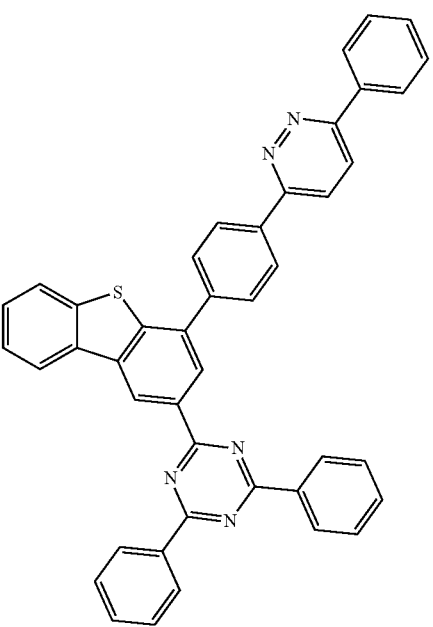

181
-continued
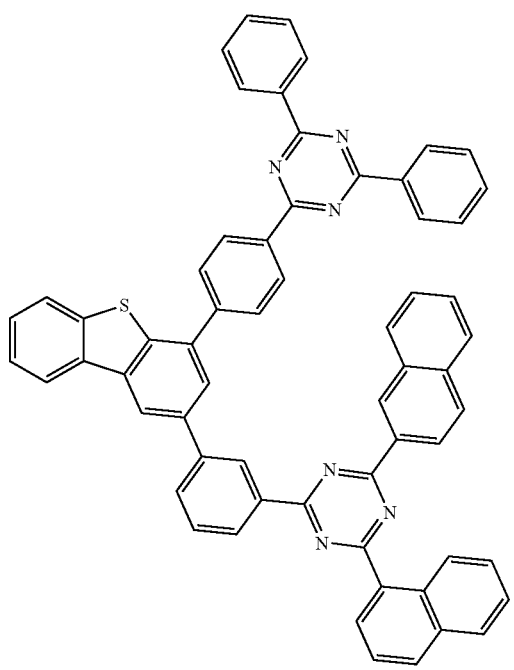
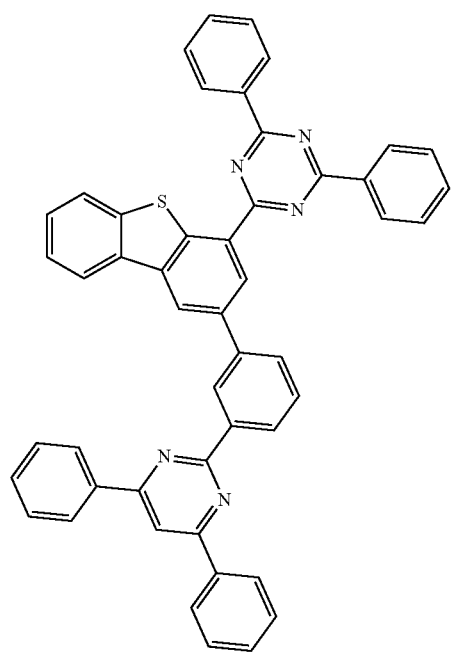
182
-continued
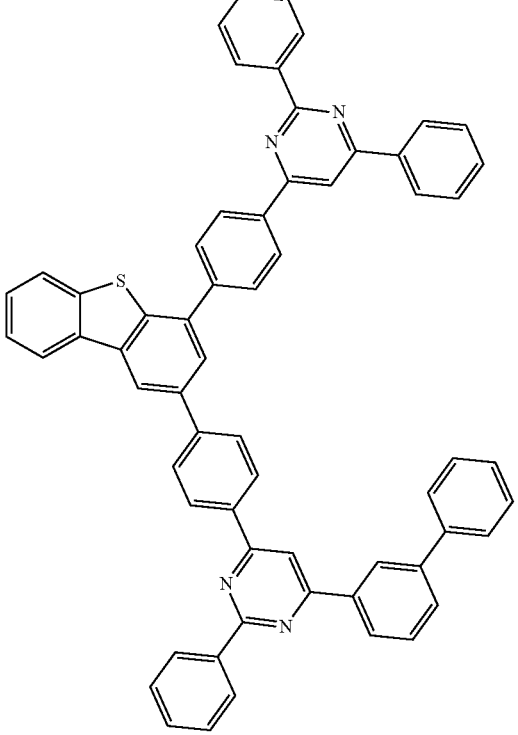
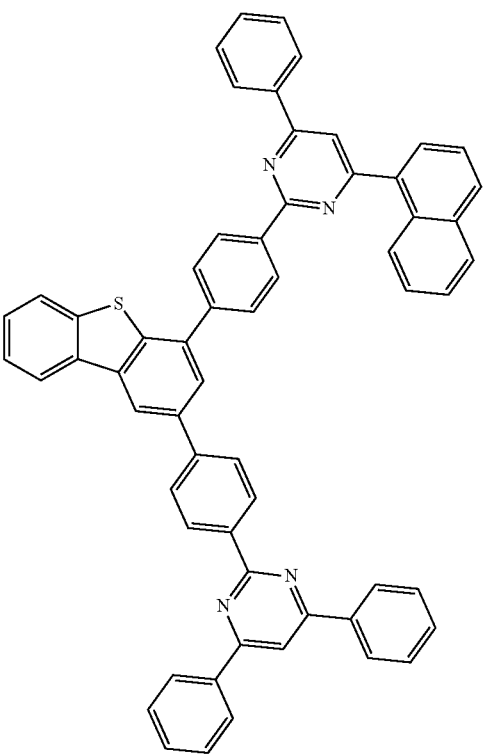

183
-continued
184
-continued
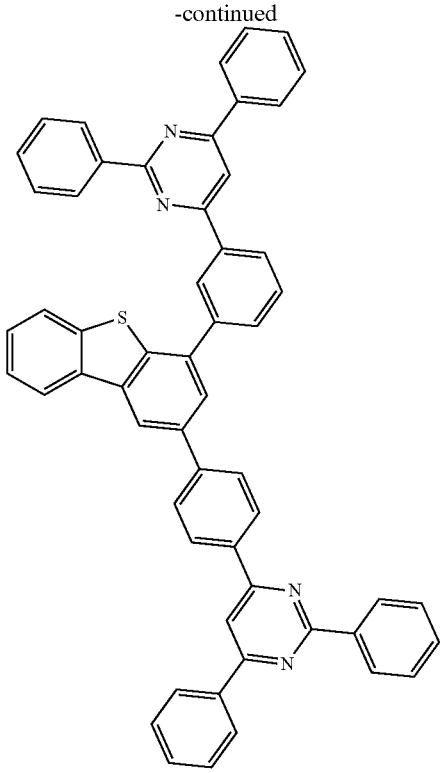
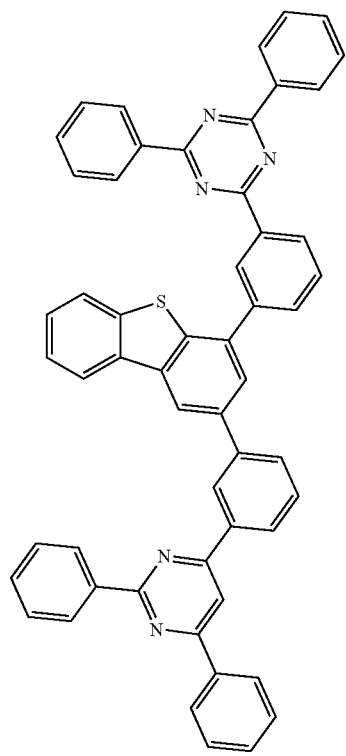

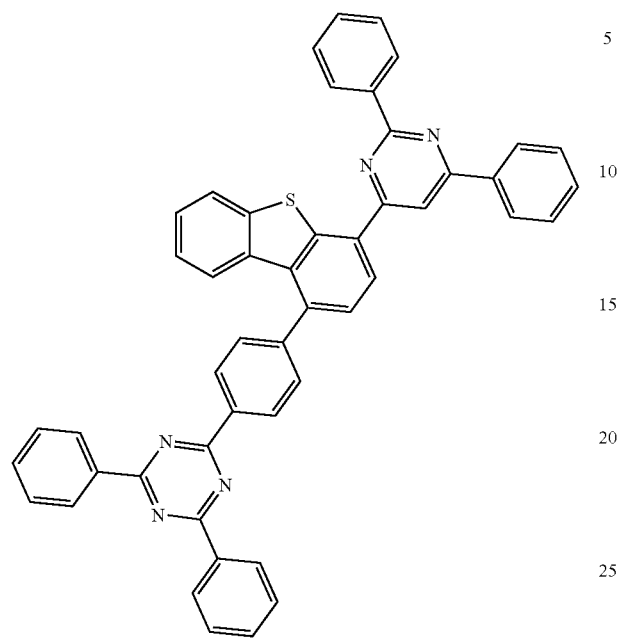
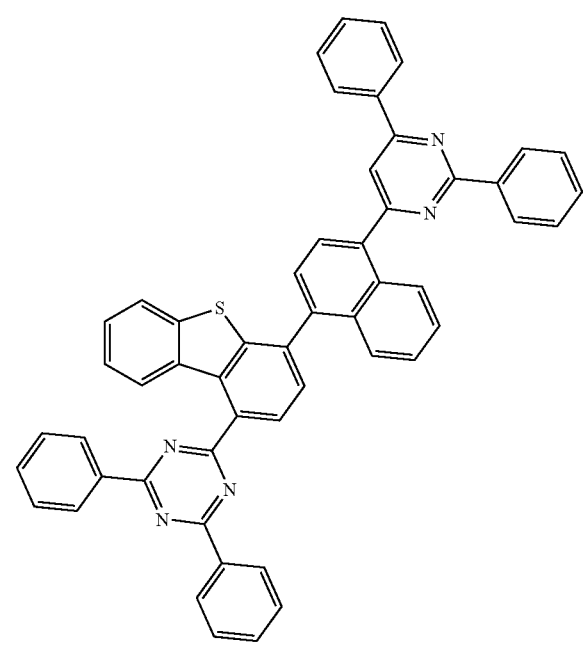
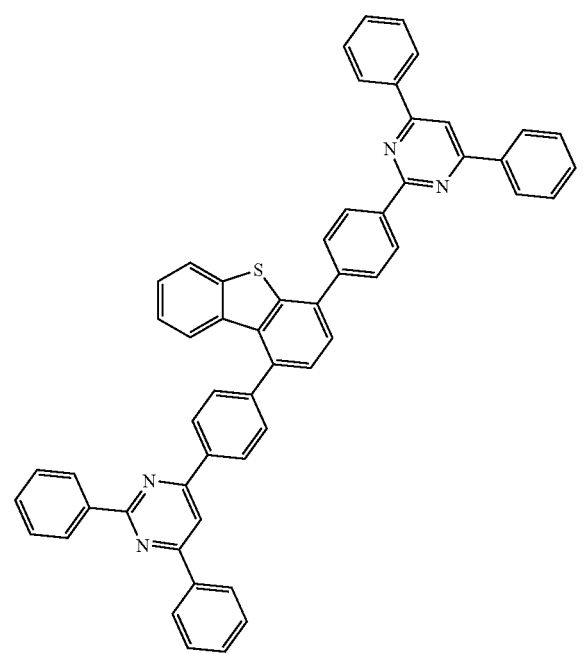

187
-continued
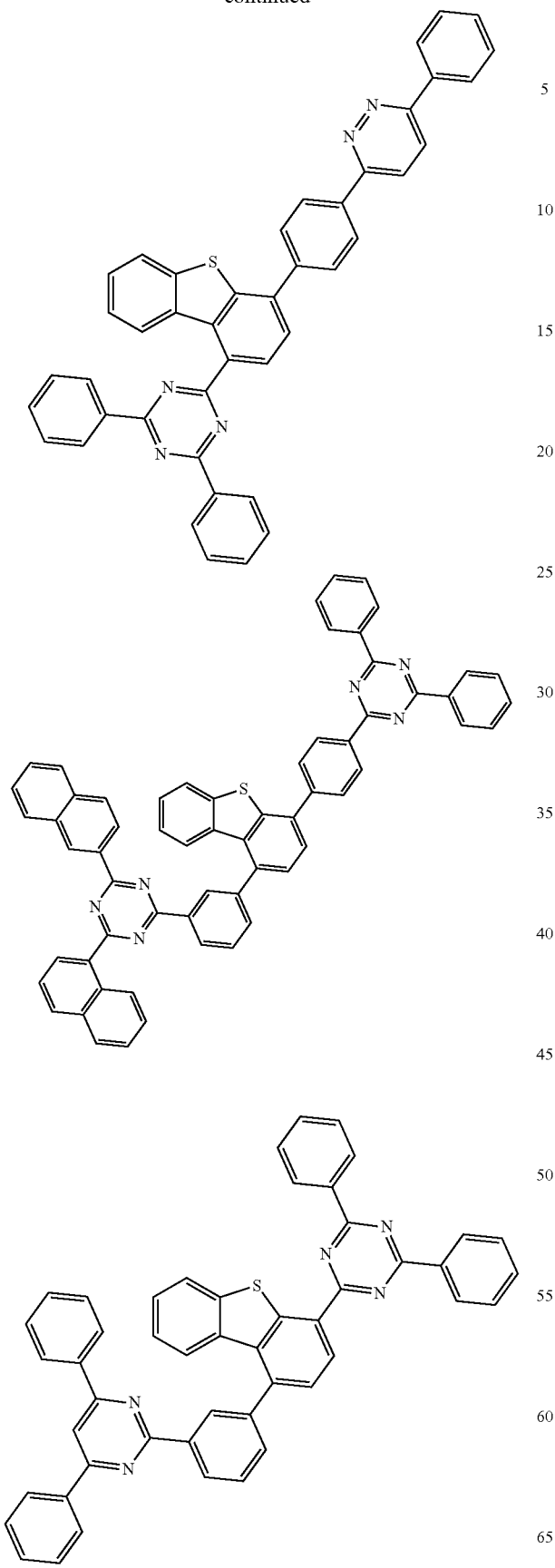
188
-continued
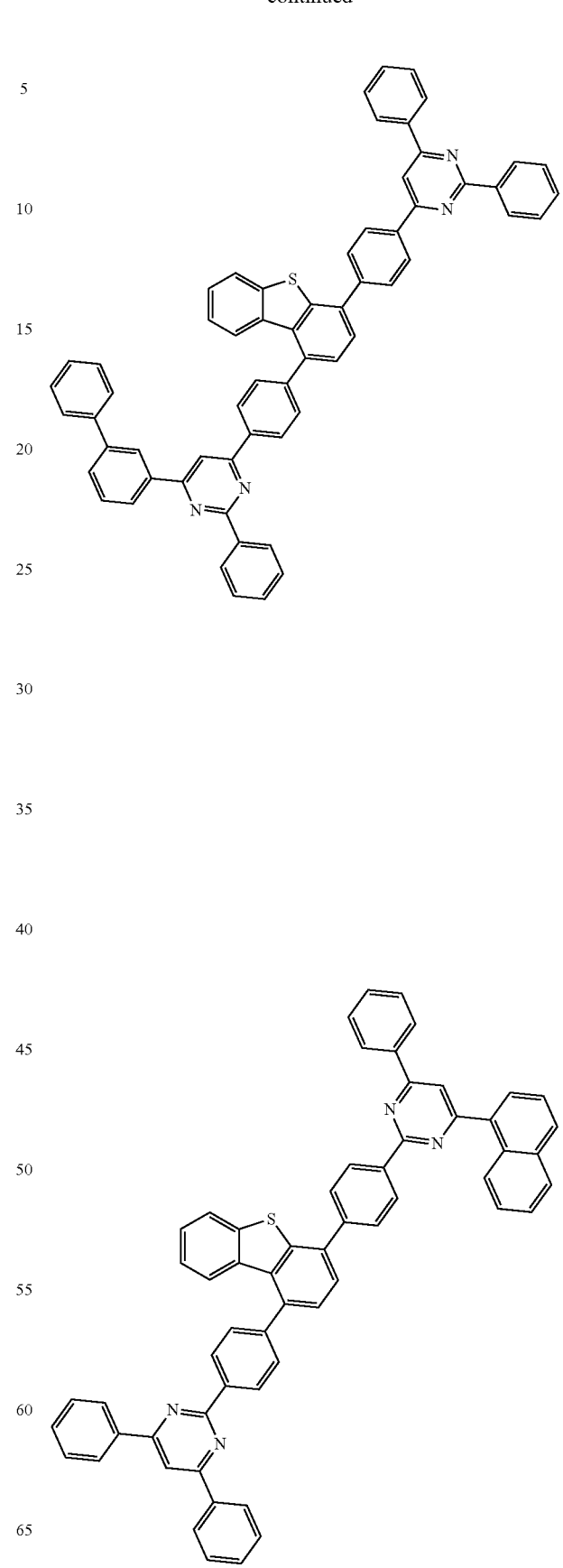

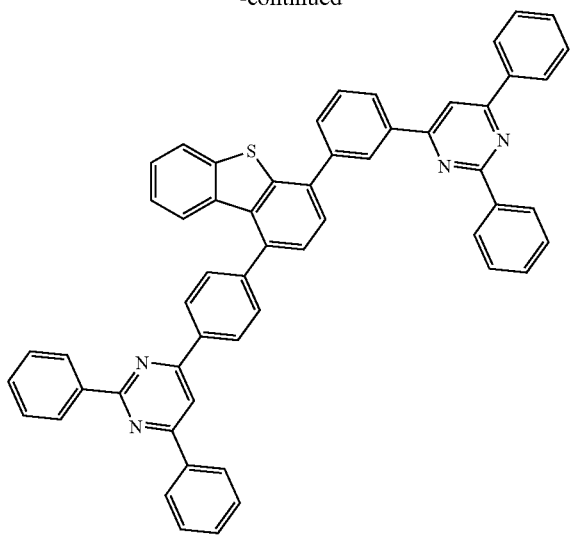
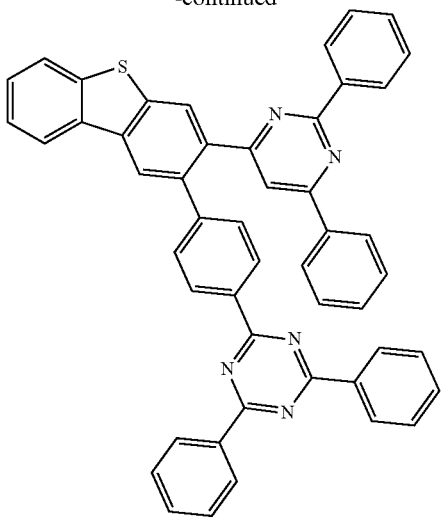
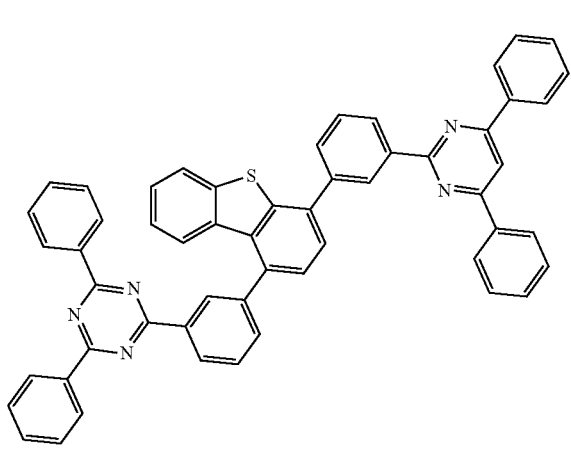
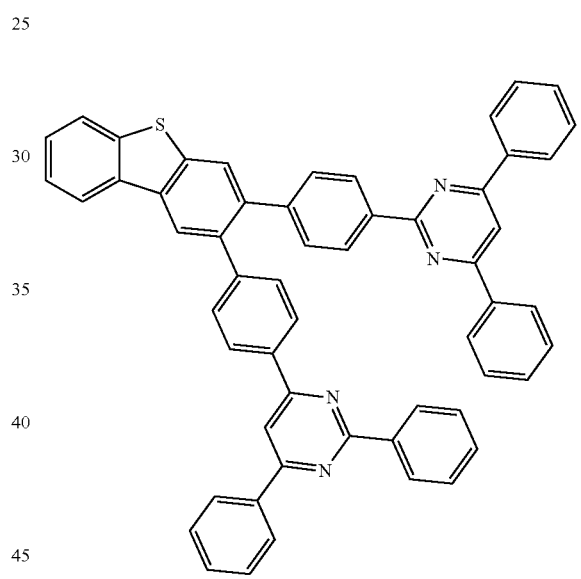
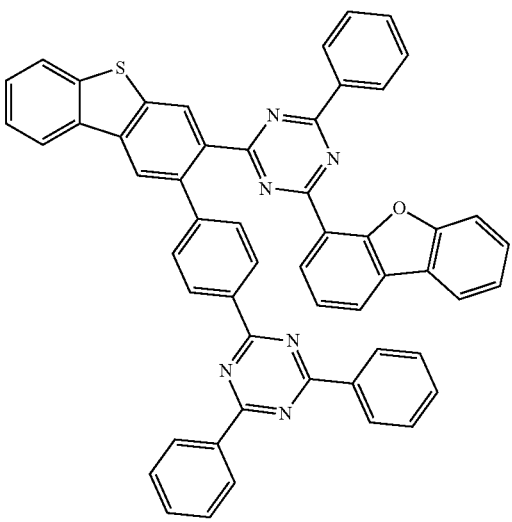
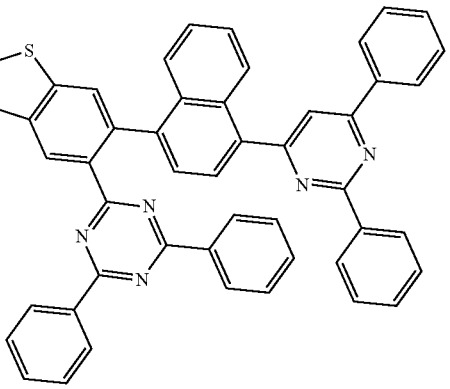

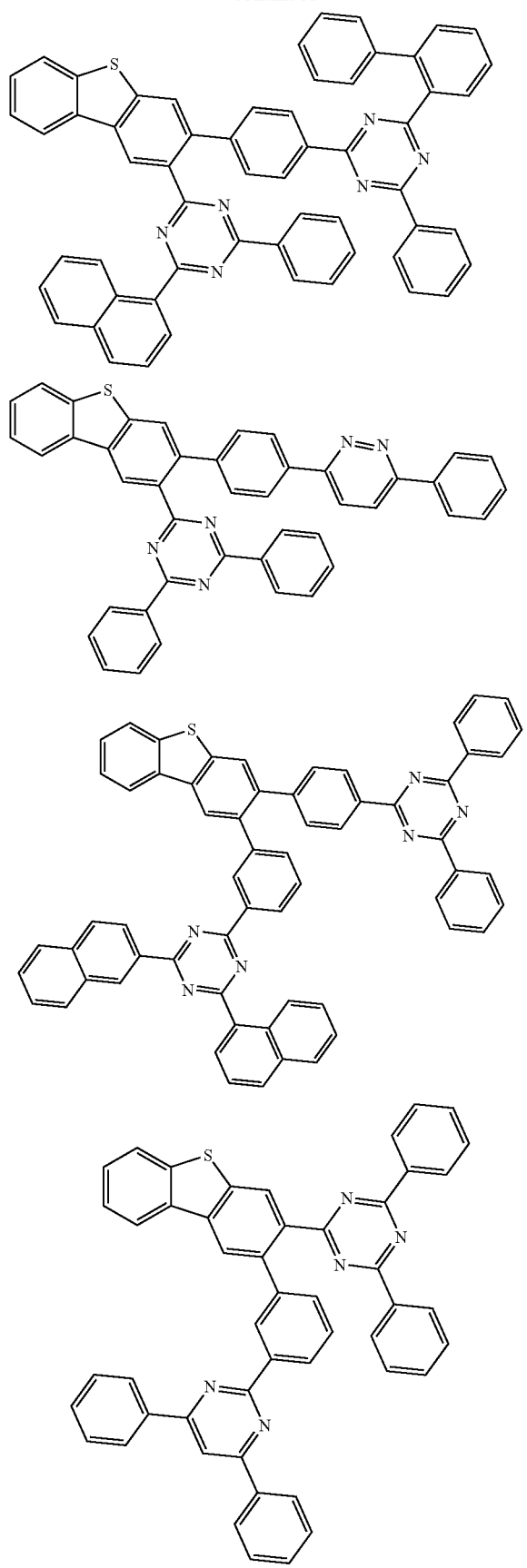
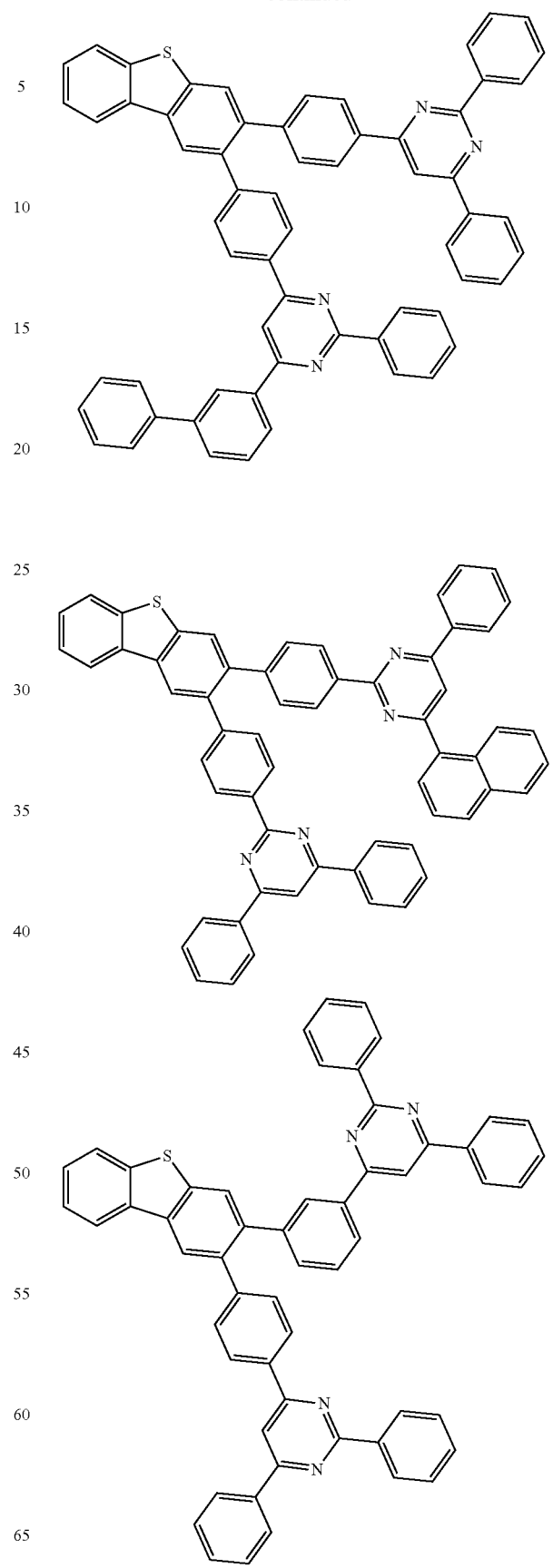

-continued
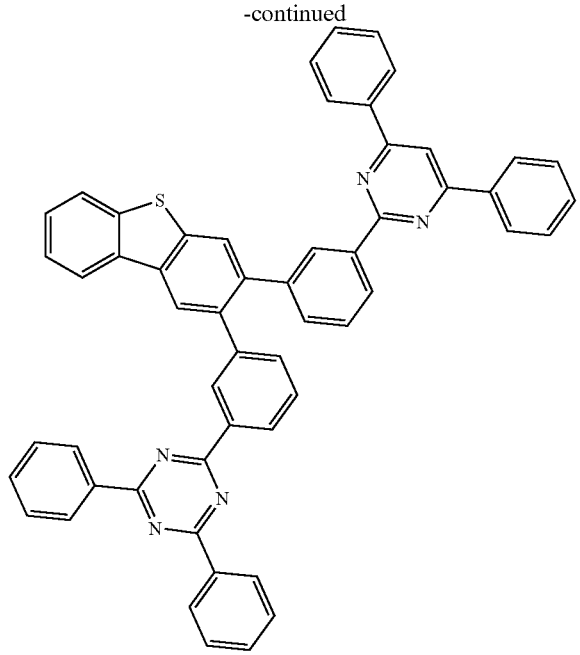
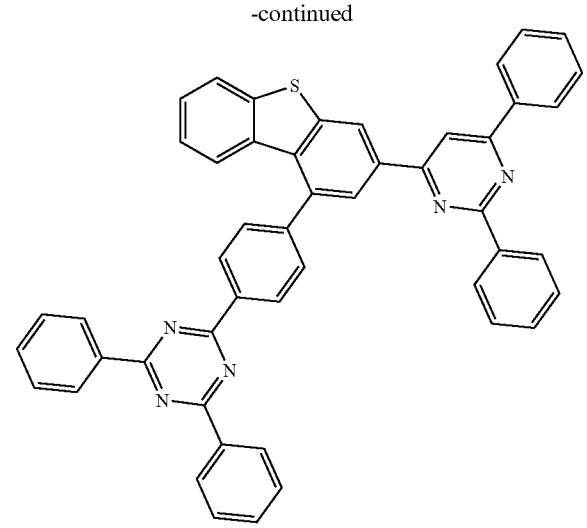
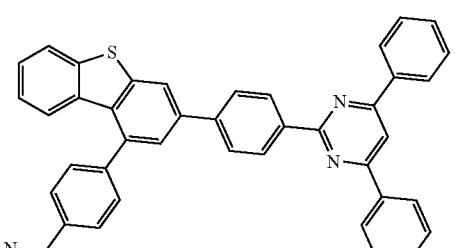
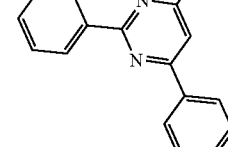
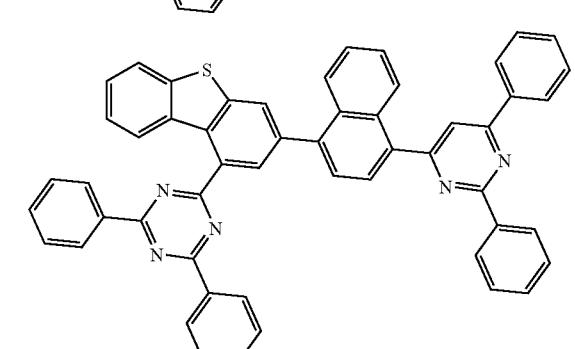
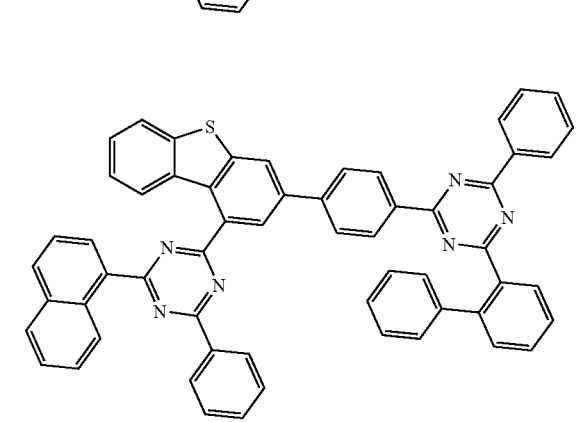

-continued
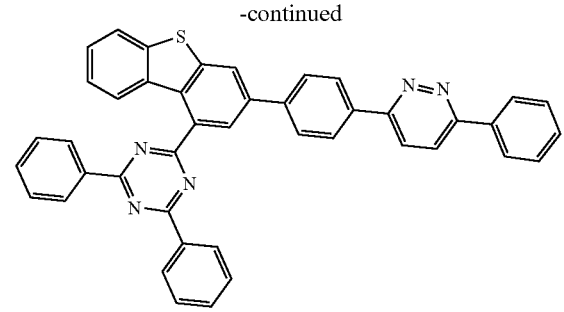
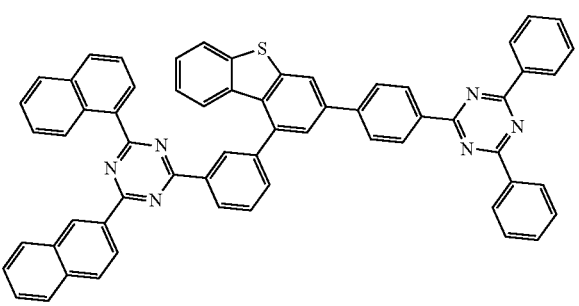
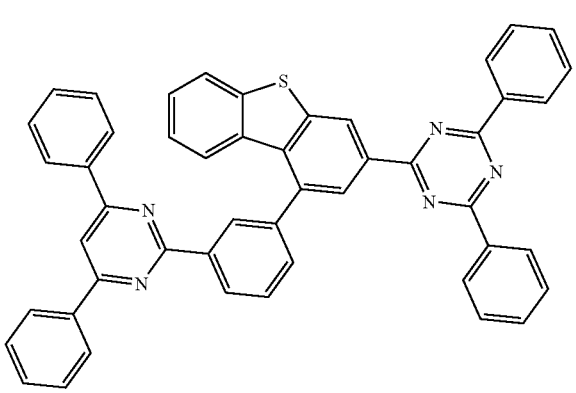
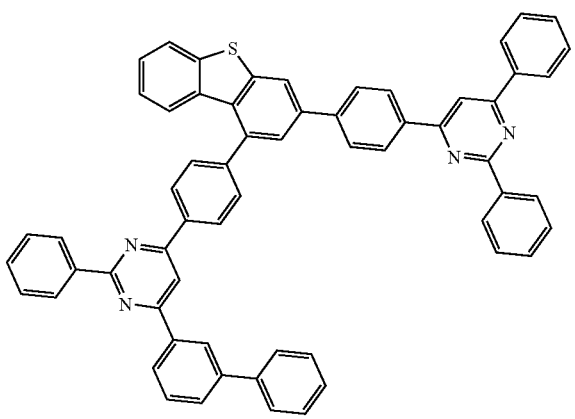
-continued
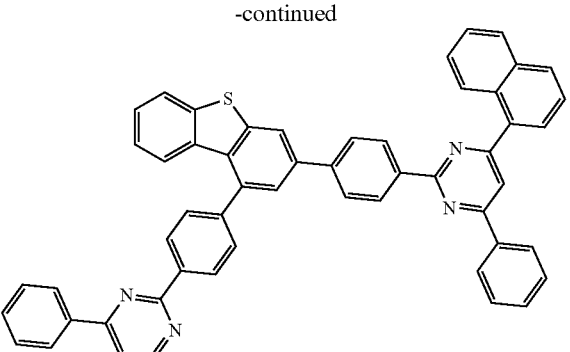
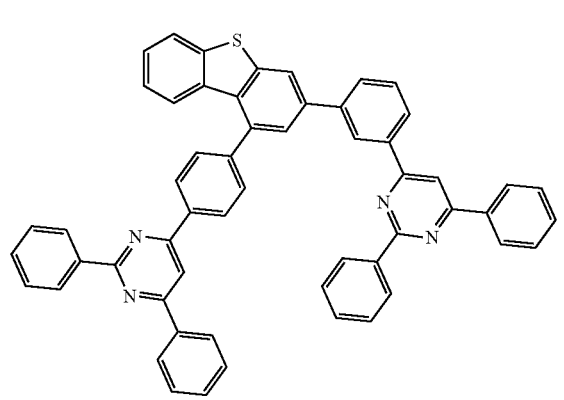
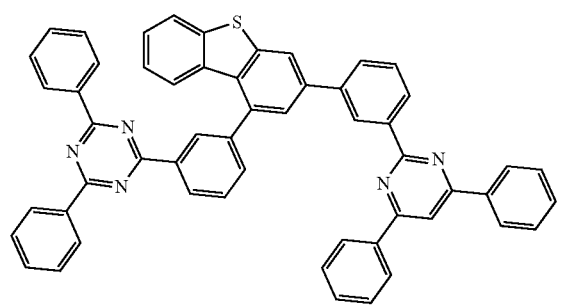
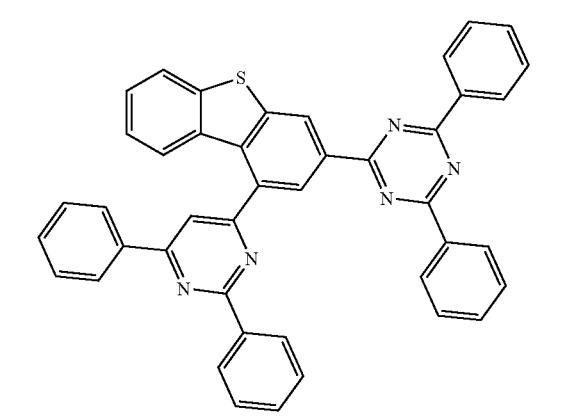

197
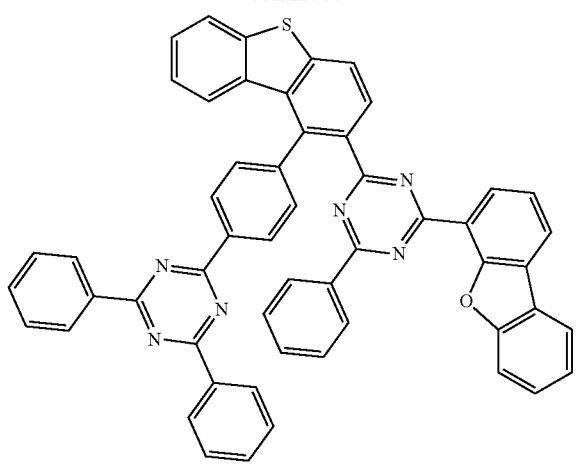
198
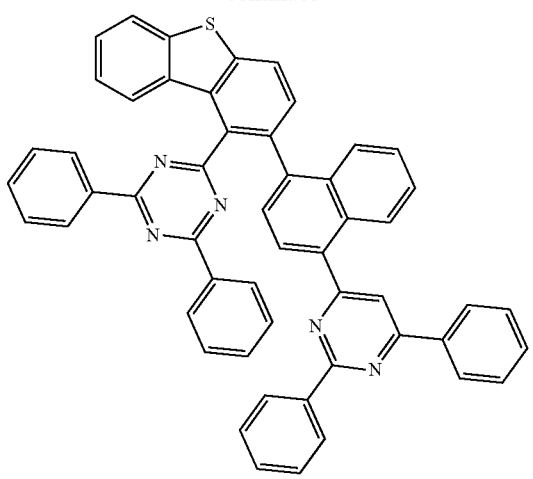
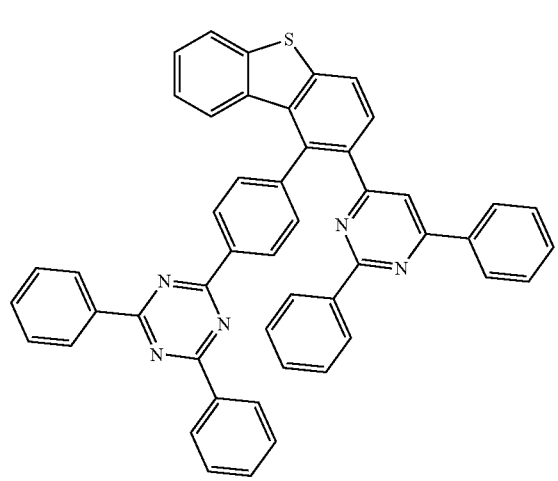
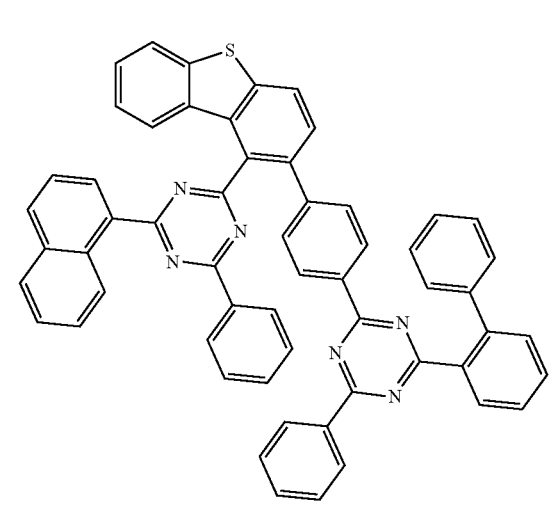
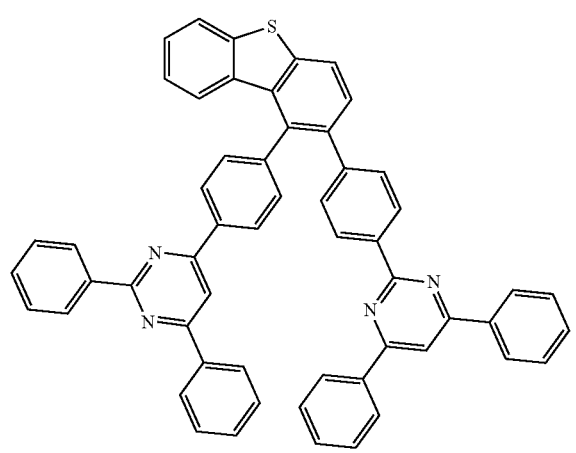
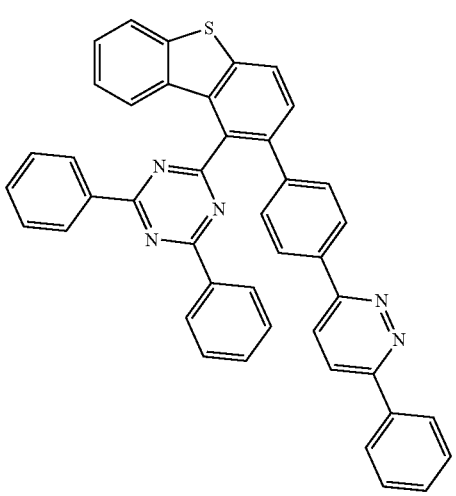

199
-continued
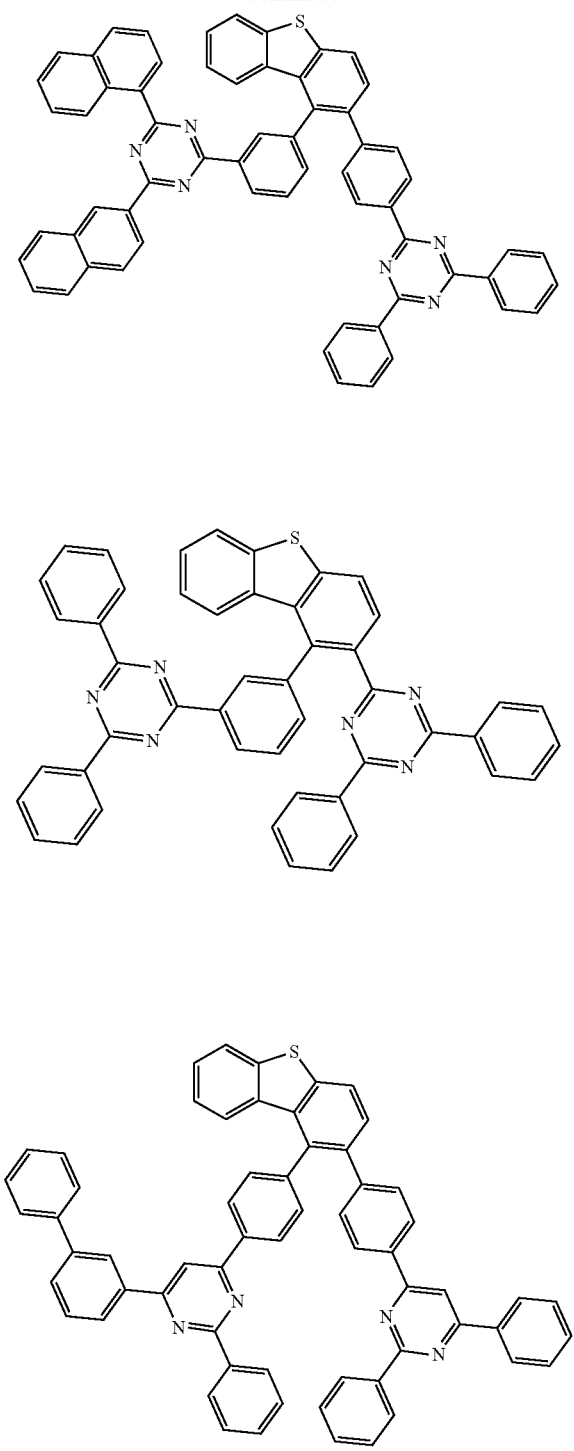
200
-continued
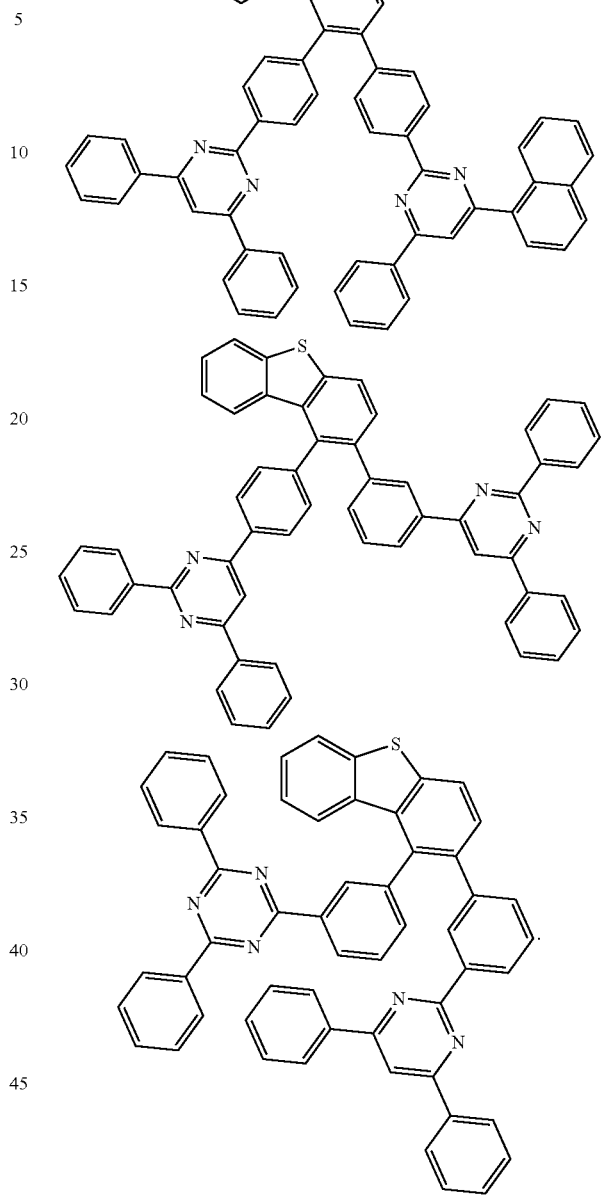
7. An organic light emitting device comprising a first electrode; a second electrode provided to face the first electrode; and at least one layer of organic material layers provided between the first electrode and the second electrode, wherein the at least one layer of the organic material layers includes a compound according to claim 1.
* * * * *